(12) United States Patent
Hunt et al.

(10) Patent No.: US 12,114,994 B2
(45) Date of Patent: *Oct. 15, 2024

(54) SENSOR ENABLED WOUND THERAPY DRESSINGS AND SYSTEMS IMPLEMENTING CYBERSECURITY

(71) Applicant: Smith & Nephew PLC, Watford (GB)

(72) Inventors: Allan Kenneth Frazer Grugeon Hunt, Beverley (GB); Marcus Damian Phillips, Wakefield (GB); Felix Clarence Quintanar, Hull (GB); Damian Lawson Smith, Swanland (GB); Charlotte Urwin, Hull (GB)

(73) Assignee: Smith & Nephew PLC, Watford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/130,606

(22) Filed: Apr. 4, 2023

(65) Prior Publication Data

US 2023/0233140 A1 Jul. 27, 2023

Related U.S. Application Data

(63) Continuation of application No. 16/645,779, filed as application No. PCT/EP2018/074200 on Sep. 7, 2018, now Pat. No. 11,633,147.

(Continued)

(30) Foreign Application Priority Data

Nov. 15, 2017 (GB) ...................... 1718870

(51) Int. Cl.
*A61B 5/00* (2006.01)
*A61F 13/00* (2024.01)
(Continued)

(52) U.S. Cl.
CPC ............ *A61B 5/445* (2013.01); *A61B 5/0013* (2013.01); *A61B 5/002* (2013.01); *A61B 5/0077* (2013.01);
(Continued)

(58) Field of Classification Search
CPC ....... A61B 5/445; A61B 5/0013; A61B 5/002; A61B 5/0077; A61B 5/4836;
(Continued)

(56) References Cited

U.S. PATENT DOCUMENTS 3,896,802 A 7/1975 Williams
4,334,530 A 6/1982 Hassell
(Continued)

FOREIGN PATENT DOCUMENTS

CN 105232229 A 1/2016
CN 105395184 A 3/2016
(Continued)

OTHER PUBLICATIONS

Aubakir B., et al., "Vital Sign Monitoring Utilizing Eulerian Video Magnification and Thermography," 38th Annual International Conference of the IEEE Engineering in Medicine and Biology Society, Aug. 16, 2016, pp. 3527-3530 (4 pages).
(Continued)

*Primary Examiner* — Rene T Towa
(74) *Attorney, Agent, or Firm* — Knobbe, Martens, Olson & Bear, LLP

(57) ABSTRACT

In some embodiments, a wound monitoring and/or therapy apparatus includes a wound dressing configured to be positioned in contact with a wound, the wound dressing comprising one or more sensors configured to obtain measurement data of at least one of the wound or periwound. The apparatus can also include a controller configured to maintain a device clock indicative of a non-real time clock,
(Continued)

receive measurement data obtained by the one or more sensors, and transmit measurement data to a remote computing device according to a security protocol, the security protocol comprising including the device clock associated with the measurement data in the transmission.

18 Claims, 20 Drawing Sheets

Related U.S. Application Data

(60) Provisional application No. 62/586,833, filed on Nov. 15, 2017, provisional application No. 62/556,505, filed on Sep. 11, 2017, provisional application No. 62/556,504, filed on Sep. 10, 2017.

(51) Int. Cl.
*A61F 13/0206* (2024.01)
*A61F 13/05* (2024.01)
*A61F 13/08* (2006.01)

(52) U.S. Cl.
CPC .......... *A61B 5/4836* (2013.01); *A61B 5/6833* (2013.01); *A61F 13/00063* (2013.01); *A61F 13/0206* (2013.01); *A61F 13/05* (2024.01); *A61F 13/08* (2013.01)

(58) Field of Classification Search
CPC ............. A61B 5/6833; A61F 13/00063; A61F 13/0206; A61F 13/05; A61F 13/08; A61F 13/00051
See application file for complete search history.

(56) References Cited

U.S. PATENT DOCUMENTS

| | | | |
|---|---|---|---|
| 5,090,410 A | 2/1992 | Saper et al. |
| 5,253,654 A | 10/1993 | Thomas et al. |
| 5,635,201 A | 6/1997 | Fabo |
| 5,642,096 A | 6/1997 | Leyerer et al. |
| 5,678,448 A | 10/1997 | Fullen et al. |
| 5,690,610 A | 11/1997 | Ito et al. |
| 5,836,990 A | 11/1998 | Li |
| 5,891,049 A | 4/1999 | Cyrus et al. |
| 6,095,992 A | 8/2000 | Augustine |
| 6,178,342 B1 | 1/2001 | Borgos et al. |
| 6,381,482 B1 | 4/2002 | Jayaraman et al. |
| 6,517,484 B1 | 2/2003 | Wilk et al. |
| 6,551,252 B2 | 4/2003 | Sackner et al. |
| 6,731,987 B1 | 5/2004 | McAdams et al. |
| 7,077,832 B2 | 7/2006 | Fleischmann |
| 7,088,591 B2 | 8/2006 | Kishimoto et al. |
| 7,201,063 B2 | 4/2007 | Taylor |
| 7,206,623 B2 | 4/2007 | Blank et al. |
| 7,289,205 B2 | 10/2007 | Yaroslavsky et al. |
| 7,316,652 B2 | 1/2008 | Dalgaard et al. |
| 7,429,255 B2 | 9/2008 | Thompson |
| 7,520,875 B2 | 4/2009 | Bernabei |
| 7,521,292 B2 | 4/2009 | Rogers et al. |
| 7,569,742 B2 | 8/2009 | Haggstrom et al. |
| 7,625,117 B2 | 12/2009 | Haslett et al. |
| 7,687,678 B2 | 3/2010 | Jacobs |
| 7,846,141 B2 | 12/2010 | Weston |
| 7,877,866 B1 | 2/2011 | Greenberg et al. |
| 7,884,258 B2 | 2/2011 | Boehringer et al. |
| 7,904,133 B2 | 3/2011 | Gehman et al. |
| 7,922,676 B2 | 4/2011 | Daskal et al. |
| 7,942,869 B2 | 5/2011 | Houbolt et al. |
| 7,945,302 B2 | 5/2011 | McAdams |
| 8,019,401 B1 | 9/2011 | Smith et al. |
| 8,032,210 B2 | 10/2011 | Finneran et al. |
| 8,060,174 B2 | 11/2011 | Simpson et al. |
| 8,079,247 B2 | 12/2011 | Russell et al. |
| 8,111,165 B2 | 2/2012 | Ortega et al. |
| 8,116,841 B2 | 2/2012 | Bly et al. |
| 8,182,425 B2 | 5/2012 | Stamatas et al. |
| 8,238,996 B2 | 8/2012 | Burnes et al. |
| 8,241,231 B2 | 8/2012 | Bausewein et al. |
| 8,332,053 B1 | 12/2012 | Patterson et al. |
| 8,333,874 B2 | 12/2012 | Currie |
| 8,366,692 B2 | 2/2013 | Weston et al. |
| 8,480,641 B2 | 7/2013 | Jacobs |
| 8,579,872 B2 | 11/2013 | Coulthard et al. |
| 8,644,911 B1 | 2/2014 | Panasyuk et al. |
| 8,663,106 B2 | 3/2014 | Stivoric et al. |
| 8,682,442 B2 | 3/2014 | McAdams |
| 8,783,948 B2 | 7/2014 | Panda et al. |
| 8,788,009 B2 | 7/2014 | Greene et al. |
| 8,800,386 B2 | 8/2014 | Taylor |
| 8,818,478 B2 | 8/2014 | Scheffler et al. |
| 8,848,187 B2 | 9/2014 | Uematsu et al. |
| 8,894,590 B2 | 11/2014 | Lamoise et al. |
| 8,925,392 B2 | 1/2015 | Esposito et al. |
| 8,934,957 B2 | 1/2015 | Dias et al. |
| 8,934,965 B2 | 1/2015 | Rogers et al. |
| 8,943,897 B2 | 2/2015 | Beauvais et al. |
| 8,948,839 B1 | 2/2015 | Longinotti-Buitoni et al. |
| 8,997,588 B2 | 4/2015 | Taylor |
| 9,000,251 B2 | 4/2015 | Murphy et al. |
| 9,042,075 B2 | 5/2015 | Borini et al. |
| 9,192,531 B2 | 11/2015 | Wu |
| 9,220,455 B2 | 12/2015 | Sarrafzadeh et al. |
| 9,226,402 B2 | 12/2015 | Hsu |
| 9,282,897 B2 | 3/2016 | Ross, Jr. et al. |
| 9,314,175 B2 | 4/2016 | Jacofsky et al. |
| 9,320,473 B2 | 4/2016 | Shuler |
| 9,372,123 B2 | 6/2016 | Li et al. |
| 9,378,450 B1 | 6/2016 | Mei et al. |
| 9,386,947 B2 | 7/2016 | Johnson |
| 9,393,354 B2 | 7/2016 | Freedman et al. |
| 9,402,988 B2 | 8/2016 | Buchanan et al. |
| 9,408,573 B2 | 8/2016 | Welch et al. |
| 9,427,179 B2 | 8/2016 | Mestrovic et al. |
| 9,439,599 B2 | 9/2016 | Thompson et al. |
| 9,483,726 B2 | 11/2016 | Mei et al. |
| 9,494,474 B2 | 11/2016 | Servati et al. |
| 9,511,215 B2 | 12/2016 | Skiba |
| 9,516,758 B2 | 12/2016 | Arora et al. |
| 9,526,439 B2 | 12/2016 | Connelly et al. |
| 9,554,484 B2 | 1/2017 | Rogers et al. |
| 9,572,507 B2 | 2/2017 | Moore et al. |
| 9,582,072 B2 | 2/2017 | Connor |
| 9,585,620 B2 | 3/2017 | Paquet et al. |
| 9,587,991 B2 | 3/2017 | Padiy |
| 9,592,007 B2 | 3/2017 | Nuovo et al. |
| 9,603,560 B2 | 3/2017 | Monty et al. |
| 9,610,388 B2 | 4/2017 | Aceto et al. |
| 9,613,911 B2 | 4/2017 | Rogers et al. |
| 9,629,584 B2 | 4/2017 | Macia Barber et al. |
| 9,675,238 B2 | 6/2017 | Iida et al. |
| 9,687,195 B2 | 6/2017 | Sims et al. |
| 9,717,565 B2 | 8/2017 | Blair |
| 9,829,471 B2 | 11/2017 | Hammond et al. |
| 9,907,103 B2 | 2/2018 | Chen et al. |
| 10,004,643 B2 | 6/2018 | Luckemeyer et al. |
| 10,046,096 B2 | 8/2018 | Askem et al. |
| 10,080,524 B1 | 9/2018 | Xi |
| 10,086,117 B2 | 10/2018 | Locke et al. |
| 10,117,705 B2 | 11/2018 | Chernov et al. |
| 10,152,789 B2 | 12/2018 | Carnes et al. |
| 10,182,740 B2 | 1/2019 | Tonar et al. |
| 10,207,031 B2 | 2/2019 | Toth |
| 10,209,213 B2 | 2/2019 | Kang et al. |
| 10,285,620 B2 | 5/2019 | Jung et al. |
| 10,321,862 B2 | 6/2019 | Dalene et al. |
| 10,463,773 B2 | 11/2019 | Haggstrom et al. |
| 10,857,038 B2 | 12/2020 | Zamierowski et al. |
| 11,026,847 B2 | 6/2021 | Piotrowski et al. |
| 11,229,553 B2 | 1/2022 | Chen et al. |
| 11,647,922 B2 | 5/2023 | Scherer |
| 11,850,121 B2 | 12/2023 | Rapp |
| 2002/0016536 A1 | 2/2002 | Benni |

(56) References Cited

U.S. PATENT DOCUMENTS

| | | |
|---|---|---|
| 2002/0135752 A1 | 9/2002 | Sokolov et al. |
| 2003/0033032 A1 | 2/2003 | Lind et al. |
| 2003/0208148 A1 | 11/2003 | Sullivan |
| 2003/0210810 A1 | 11/2003 | Gee et al. |
| 2003/0216630 A1 | 11/2003 | Jersey-Willuhn et al. |
| 2004/0230132 A1 | 11/2004 | Shehada |
| 2005/0088832 A1 | 4/2005 | Su et al. |
| 2005/0240107 A1 | 10/2005 | Alfano et al. |
| 2005/0280531 A1 | 12/2005 | Fadem et al. |
| 2006/0052678 A1 | 3/2006 | Drinan et al. |
| 2006/0058690 A1* | 3/2006 | Bartnik ............... A61B 5/0261 600/507 |
| 2006/0181791 A1 | 8/2006 | Van Beek et al. |
| 2006/0234383 A1 | 10/2006 | Gough |
| 2006/0241495 A1 | 10/2006 | Kurtz |
| 2007/0055209 A1 | 3/2007 | Patel et al. |
| 2007/0173892 A1 | 7/2007 | Fleischer et al. |
| 2007/0191754 A1 | 8/2007 | Aali |
| 2007/0260421 A1 | 11/2007 | Berner, Jr. et al. |
| 2007/0293748 A1 | 12/2007 | Engvall et al. |
| 2008/0081973 A1 | 4/2008 | Hoarau |
| 2008/0140140 A1 | 6/2008 | Grimley et al. |
| 2008/0167535 A1 | 7/2008 | Stivoric et al. |
| 2008/0258717 A1 | 10/2008 | Igney et al. |
| 2008/0287747 A1 | 11/2008 | Mestrovic et al. |
| 2008/0319282 A1 | 12/2008 | Tran |
| 2008/0319283 A1 | 12/2008 | Cotton et al. |
| 2009/0030293 A1 | 1/2009 | Cooper et al. |
| 2009/0149800 A1 | 6/2009 | Durand |
| 2009/0177051 A1 | 7/2009 | Arons et al. |
| 2009/0177110 A1 | 7/2009 | Lyden et al. |
| 2009/0209830 A1 | 8/2009 | Nagle et al. |
| 2009/0234206 A1 | 9/2009 | Gaspard et al. |
| 2009/0245601 A1 | 10/2009 | Cohen et al. |
| 2010/0022990 A1 | 1/2010 | Karpowicz et al. |
| 2010/0025831 A1 | 2/2010 | Yamazaki et al. |
| 2010/0166252 A1 | 7/2010 | Ahmed et al. |
| 2010/0168727 A1 | 7/2010 | Hancock et al. |
| 2010/0305473 A1 | 12/2010 | Yuzhakov |
| 2011/0004088 A1 | 1/2011 | Grossman |
| 2011/0015591 A1 | 1/2011 | Hanson et al. |
| 2011/0054283 A1 | 3/2011 | Shuler |
| 2011/0092958 A1* | 4/2011 | Jacobs ............... A61M 1/95 604/543 |
| 2011/0130697 A1 | 6/2011 | Nagle et al. |
| 2011/0140703 A1 | 6/2011 | Chiao et al. |
| 2011/0190639 A1 | 8/2011 | Peltie et al. |
| 2011/0218757 A1 | 9/2011 | Callsen et al. |
| 2011/0242532 A1 | 10/2011 | McKenna |
| 2011/0245682 A1 | 10/2011 | Robinson et al. |
| 2011/0301441 A1 | 12/2011 | Bandic et al. |
| 2012/0029306 A1 | 2/2012 | Paquet et al. |
| 2012/0029307 A1 | 2/2012 | Paquet et al. |
| 2012/0029410 A1 | 2/2012 | Koenig et al. |
| 2012/0112347 A1 | 5/2012 | Eckhardt et al. |
| 2012/0165717 A1 | 6/2012 | Al Khaburi |
| 2012/0190956 A1 | 7/2012 | Connolly |
| 2012/0190989 A1 | 7/2012 | Kaiser et al. |
| 2012/0265120 A1 | 10/2012 | Beisang, III et al. |
| 2012/0271265 A1 | 10/2012 | Langdon |
| 2012/0277559 A1 | 11/2012 | Kohl-Bareis et al. |
| 2012/0316538 A1 | 12/2012 | Heiser et al. |
| 2012/0330252 A1 | 12/2012 | Stokes et al. |
| 2013/0041235 A1 | 2/2013 | Rogers et al. |
| 2013/0064772 A1 | 3/2013 | Swiss et al. |
| 2013/0121544 A1 | 5/2013 | Sarrafzadeh et al. |
| 2013/0123722 A1 | 5/2013 | Pratt et al. |
| 2013/0151223 A1 | 6/2013 | Zamierowski et al. |
| 2013/0200268 A1 | 8/2013 | Rafferty et al. |
| 2013/0261409 A1 | 10/2013 | Pathak et al. |
| 2013/0262357 A1* | 10/2013 | Amarasingham ...... G16H 50/70 706/21 |
| 2013/0271278 A1* | 10/2013 | Duesterhoft ......... A61B 5/0022 340/539.12 |
| 2013/0274563 A1 | 10/2013 | Duesterhoft et al. |
| 2013/0274629 A1 | 10/2013 | Duesterhoft et al. |
| 2013/0317367 A1 | 11/2013 | Shuler |
| 2014/0012108 A1 | 1/2014 | McPeak |
| 2014/0018637 A1 | 1/2014 | Bennett et al. |
| 2014/0024905 A1 | 1/2014 | Sarrafzadeh et al. |
| 2014/0031663 A1 | 1/2014 | Gallego et al. |
| 2014/0072190 A1 | 3/2014 | Wu et al. |
| 2014/0075658 A1 | 3/2014 | McGuin |
| 2014/0107495 A1 | 4/2014 | Marinelli et al. |
| 2014/0107498 A1 | 4/2014 | Bower et al. |
| 2014/0147611 A1 | 5/2014 | Ackerman, Jr. |
| 2014/0203797 A1 | 7/2014 | Stivoric et al. |
| 2014/0206947 A1 | 7/2014 | Isserow et al. |
| 2014/0232516 A1 | 8/2014 | Stivoric et al. |
| 2014/0235166 A1 | 8/2014 | Molettiere et al. |
| 2014/0243709 A1 | 8/2014 | Gibson et al. |
| 2014/0296749 A1 | 10/2014 | Reid, Jr. et al. |
| 2014/0298927 A1 | 10/2014 | Allin et al. |
| 2014/0298928 A1 | 10/2014 | Duesterhoft et al. |
| 2014/0303463 A1 | 10/2014 | Robinson et al. |
| 2014/0324120 A1 | 10/2014 | Bogie et al. |
| 2014/0340857 A1 | 11/2014 | Hsu et al. |
| 2014/0343478 A1 | 11/2014 | Brennan et al. |
| 2014/0350882 A1 | 11/2014 | Everett et al. |
| 2015/0018792 A1 | 1/2015 | Marsiquet et al. |
| 2015/0025343 A1 | 1/2015 | Gareau et al. |
| 2015/0138330 A1 | 5/2015 | Krishnamoorthi |
| 2015/0141767 A1 | 5/2015 | Rogers et al. |
| 2015/0148760 A1 | 5/2015 | Dodd et al. |
| 2015/0150479 A1 | 6/2015 | Yoshino et al. |
| 2015/0182166 A1 | 7/2015 | Evans et al. |
| 2015/0223716 A1 | 8/2015 | Korkala et al. |
| 2015/0257644 A1 | 9/2015 | Cao |
| 2015/0265191 A1 | 9/2015 | Harding et al. |
| 2015/0292968 A1 | 10/2015 | Vogt et al. |
| 2015/0313476 A1 | 11/2015 | Pisani et al. |
| 2015/0313533 A1 | 11/2015 | Rapp et al. |
| 2015/0327777 A1 | 11/2015 | Kostic et al. |
| 2015/0335254 A1 | 11/2015 | Fastert et al. |
| 2015/0335287 A1 | 11/2015 | Neuman et al. |
| 2015/0335288 A1 | 11/2015 | Toth et al. |
| 2015/0351970 A1 | 12/2015 | Dagger et al. |
| 2015/0359485 A1 | 12/2015 | Berg et al. |
| 2015/0374309 A1 | 12/2015 | Farkas et al. |
| 2016/0015962 A1 | 1/2016 | Shokoueinejad Maragheh et al. |
| 2016/0022223 A1 | 1/2016 | Grundfest et al. |
| 2016/0029900 A1 | 2/2016 | LaPlante et al. |
| 2016/0030132 A1 | 2/2016 | Cheung et al. |
| 2016/0038045 A1 | 2/2016 | Shapiro |
| 2016/0038083 A1 | 2/2016 | Ding et al. |
| 2016/0051147 A1 | 2/2016 | Cohen et al. |
| 2016/0058380 A1 | 3/2016 | Lee et al. |
| 2016/0066854 A1 | 3/2016 | Mei et al. |
| 2016/0069743 A1 | 3/2016 | McQuilkin et al. |
| 2016/0074234 A1 | 3/2016 | Abichandani et al. |
| 2016/0081580 A1 | 3/2016 | Bergelin et al. |
| 2016/0081601 A1 | 3/2016 | Ballam et al. |
| 2016/0100790 A1 | 4/2016 | Cantu et al. |
| 2016/0100987 A1 | 4/2016 | Hartwell et al. |
| 2016/0101282 A1 | 4/2016 | Bergelin et al. |
| 2016/0129469 A1 | 5/2016 | Kulinsky et al. |
| 2016/0143534 A1 | 5/2016 | Hyde et al. |
| 2016/0157779 A1 | 6/2016 | Baxi et al. |
| 2016/0165719 A1 | 6/2016 | Li et al. |
| 2016/0166438 A1 | 6/2016 | Rovaniemi |
| 2016/0213269 A1 | 7/2016 | Lam et al. |
| 2016/0228049 A1 | 8/2016 | Nackaerts et al. |
| 2016/0232807 A1 | 8/2016 | Ghaffari et al. |
| 2016/0242331 A1 | 8/2016 | Park et al. |
| 2016/0249810 A1 | 9/2016 | Darty et al. |
| 2016/0256080 A1 | 9/2016 | Shen et al. |
| 2016/0262672 A1 | 9/2016 | Hammond et al. |
| 2016/0262687 A1 | 9/2016 | Vaidyanathan et al. |
| 2016/0270700 A1 | 9/2016 | Baxi et al. |
| 2016/0287177 A1 | 10/2016 | Huppert et al. |
| 2016/0302729 A1 | 10/2016 | Starr et al. |
| 2016/0310023 A1 | 10/2016 | Chachisvilis et al. |
| 2016/0317057 A1 | 11/2016 | Li et al. |
| 2016/0331263 A1 | 11/2016 | Cailler et al. |

(56) References Cited

U.S. PATENT DOCUMENTS

| | | |
|---|---|---|
| 2016/0331322 A1 | 11/2016 | Son et al. |
| 2016/0338591 A1 | 11/2016 | Lachenbruch et al. |
| 2016/0354001 A1 | 12/2016 | Buckley et al. |
| 2016/0367189 A1 | 12/2016 | Aimone et al. |
| 2016/0367192 A1 | 12/2016 | Iyengar et al. |
| 2016/0367406 A1 | 12/2016 | Barnett |
| 2017/0000407 A1 | 1/2017 | Saxby et al. |
| 2017/0007853 A1 | 1/2017 | Alford et al. |
| 2017/0027498 A1 | 2/2017 | Larson et al. |
| 2017/0079740 A1 | 3/2017 | Hufnagel et al. |
| 2017/0086519 A1 | 3/2017 | Vigano' et al. |
| 2017/0086709 A1 | 3/2017 | Khine et al. |
| 2017/0095208 A1 | 4/2017 | Oberleitner et al. |
| 2017/0146474 A1 | 5/2017 | Bedell et al. |
| 2017/0150905 A1 | 6/2017 | Shen et al. |
| 2017/0156594 A1 | 6/2017 | Stivoric et al. |
| 2017/0156621 A1 | 6/2017 | Bettinger et al. |
| 2017/0156658 A1 | 6/2017 | Maharbiz et al. |
| 2017/0164865 A1 | 6/2017 | Rafferty et al. |
| 2017/0164876 A1 | 6/2017 | Hyde et al. |
| 2017/0172439 A1 | 6/2017 | Zhu et al. |
| 2017/0202711 A1 | 7/2017 | Cernasov et al. |
| 2017/0224271 A1 | 8/2017 | Lachenbruch et al. |
| 2017/0231015 A1 | 8/2017 | Jang et al. |
| 2017/0258972 A1 | 9/2017 | Weston |
| 2017/0319075 A1 | 11/2017 | Homan et al. |
| 2017/0326004 A1 | 11/2017 | Long et al. |
| 2017/0367644 A1 | 12/2017 | Sharman et al. |
| 2018/0008177 A1 | 1/2018 | Shimuta et al. |
| 2018/0055359 A1 | 3/2018 | Shamim et al. |
| 2018/0055697 A1 | 3/2018 | Mihali et al. |
| 2018/0056087 A1 | 3/2018 | Ribeiro et al. |
| 2018/0070880 A1 | 3/2018 | Trembly et al. |
| 2018/0074547 A1 | 3/2018 | Smadi et al. |
| 2018/0116877 A1 | 5/2018 | Ineichen |
| 2018/0132287 A1 | 5/2018 | Cheng et al. |
| 2018/0192514 A1 | 7/2018 | Seo |
| 2018/0200414 A1 | 7/2018 | Askem et al. |
| 2018/0206758 A1 | 7/2018 | Feldkamp et al. |
| 2018/0235484 A1 | 8/2018 | Mozdzierz |
| 2018/0296397 A1 | 10/2018 | Askem et al. |
| 2019/0021911 A1 | 1/2019 | Askem et al. |
| 2019/0060126 A1 | 2/2019 | Ribble et al. |
| 2019/0076298 A1 | 3/2019 | Quintanar et al. |
| 2019/0083025 A1 | 3/2019 | Aung et al. |
| 2019/0133812 A1 | 5/2019 | Seres et al. |
| 2019/0159938 A1 | 5/2019 | Askem et al. |
| 2019/0175098 A1 | 6/2019 | Burns |
| 2019/0192066 A1 | 6/2019 | Schoess et al. |
| 2019/0231939 A1 | 8/2019 | Askem et al. |
| 2019/0290496 A1 | 9/2019 | Brownhill et al. |
| 2019/0374387 A1 | 12/2019 | Ribble et al. |
| 2020/0054218 A1 | 2/2020 | Xi |
| 2020/0078482 A1 | 3/2020 | Yoon et al. |
| 2020/0147407 A1 | 5/2020 | Efremkin |
| 2020/0330258 A1 | 10/2020 | Hansen et al. |
| 2021/0212855 A1 | 7/2021 | Hansen et al. |

FOREIGN PATENT DOCUMENTS

| | | |
|---|---|---|
| CN | 106102322 A | 11/2016 |
| DE | 102012211015 A1 | 1/2014 |
| DE | 102013013013 A1 | 2/2015 |
| EP | 2454990 A2 | 5/2012 |
| EP | 2565630 A1 | 3/2013 |
| EP | 3034054 A1 | 6/2016 |
| EP | 3096258 A1 | 11/2016 |
| EP | 3231478 A1 | 10/2017 |
| EP | 3409190 A1 | 12/2018 |
| EP | 3499510 A1 | 6/2019 |
| EP | 3837520 A1 | 6/2021 |
| GB | 1476894 A | 6/1977 |
| GB | 2316171 A | 2/1998 |
| GB | 2563602 A | 12/2018 |
| JP | 2009225863 A | 10/2009 |
| JP | 2012160851 A | 8/2012 |
| KR | 20120119523 A | 10/2012 |
| KR | 101224629 B1 | 1/2013 |
| KR | 20140024743 A | 3/2014 |
| KR | 20140058041 A | 5/2014 |
| KR | 20160071044 A | 6/2016 |
| KR | 20190105898 A | 9/2019 |
| NL | 1027236 C2 | 4/2006 |
| WO | WO-0021433 A1 | 4/2000 |
| WO | WO-0043046 A2 | 7/2000 |
| WO | WO-03067229 A1 | 8/2003 |
| WO | WO-2006041997 A2 | 4/2006 |
| WO | WO-2007030379 A2 | 3/2007 |
| WO | WO-2008006150 A1 | 1/2008 |
| WO | WO-2008010604 A1 | 1/2008 |
| WO | WO-2009052607 A1 | 4/2009 |
| WO | WO-2009120951 A2 | 10/2009 |
| WO | WO-2009141777 A1 | 11/2009 |
| WO | WO-2010020919 A1 | 2/2010 |
| WO | WO-2010105053 A2 | 9/2010 |
| WO | WO-2011082420 A1 | 7/2011 |
| WO | WO-2011113070 A1 | 9/2011 |
| WO | WO-2011123848 A1 | 10/2011 |
| WO | WO-2012141999 A1 | 10/2012 |
| WO | WO-2013026999 A1 | 2/2013 |
| WO | WO-2013044226 A2 | 3/2013 |
| WO | WO-2013090791 A1 | 6/2013 |
| WO | WO-2013155193 A1 | 10/2013 |
| WO | WO-2013156510 A1 | 10/2013 |
| WO | WO-2014036577 A1 | 3/2014 |
| WO | WO-2014116816 A1 | 7/2014 |
| WO | WO-2014178763 A1 | 11/2014 |
| WO | WO-2014188070 A1 | 11/2014 |
| WO | WO-2015112095 A1 | 7/2015 |
| WO | WO-2015168720 A1 | 11/2015 |
| WO | WO-2016025438 A1 | 2/2016 |
| WO | WO-2016030752 A1 | 3/2016 |
| WO | WO-2016058032 A1 | 4/2016 |
| WO | WO-2016073777 A1 | 5/2016 |
| WO | WO-2016100218 A1 | 6/2016 |
| WO | WO-2016109744 A1 | 7/2016 |
| WO | WO-2016110564 A1 | 7/2016 |
| WO | WO-2016183198 A1 | 11/2016 |
| WO | WO-2016187136 A1 | 11/2016 |
| WO | WO-2016205872 A1 | 12/2016 |
| WO | WO-2016205881 A1 | 12/2016 |
| WO | WO-2017021006 A1 | 2/2017 |
| WO | WO-2017021965 A2 | 2/2017 |
| WO | WO-2017033058 A1 | 3/2017 |
| WO | WO-2017037479 A1 | 3/2017 |
| WO | WO-2017041014 A1 | 3/2017 |
| WO | WO-2017041385 A1 | 3/2017 |
| WO | WO-2017041386 A1 | 3/2017 |
| WO | WO-2017041387 A1 | 3/2017 |
| WO | WO-2017119996 A1 | 7/2017 |
| WO | WO-2017205728 A1 | 11/2017 |
| WO | WO-2017214188 A1 | 12/2017 |
| WO | WO-2018035612 A1 | 3/2018 |
| WO | WO-2018060417 A1 | 4/2018 |
| WO | WO-2018064569 A1 | 4/2018 |
| WO | WO-2018115461 A1 | 6/2018 |
| WO | WO-2018144938 A1 | 8/2018 |
| WO | WO-2018144941 A1 | 8/2018 |
| WO | WO-2018144943 A1 | 8/2018 |
| WO | WO-2018144946 A1 | 8/2018 |
| WO | WO-2018162728 A2 | 9/2018 |
| WO | WO-2018162732 A1 | 9/2018 |
| WO | WO-2018162735 A1 | 9/2018 |
| WO | WO-2018162736 A1 | 9/2018 |
| WO | WO-2018185138 A1 | 10/2018 |
| WO | WO-2018189265 A1 | 10/2018 |
| WO | WO-2018209090 A1 | 11/2018 |
| WO | WO-2018210692 A1 | 11/2018 |
| WO | WO-2018210693 A1 | 11/2018 |
| WO | WO-2018211458 A1 | 11/2018 |
| WO | WO-2018234443 A1 | 12/2018 |
| WO | WO-2019020550 A2 | 1/2019 |
| WO | WO-2019020551 A1 | 1/2019 |
| WO | WO-2019020666 A1 | 1/2019 |

(56) References Cited

FOREIGN PATENT DOCUMENTS

| | | |
|---|---|---|
| WO | WO-2019030384 A2 | 2/2019 |
| WO | WO-2019048624 A1 | 3/2019 |
| WO | WO-2019048626 A1 | 3/2019 |
| WO | WO-2019048638 A1 | 3/2019 |
| WO | WO-2019063481 A1 | 4/2019 |
| WO | WO-2019063488 A2 | 4/2019 |
| WO | WO-2019067264 A1 | 4/2019 |
| WO | WO-2019072531 A1 | 4/2019 |
| WO | WO-2019076967 A2 | 4/2019 |
| WO | WO-2019096828 A1 | 5/2019 |
| WO | WO-2019140441 A2 | 7/2019 |
| WO | WO-2019140444 A1 | 7/2019 |
| WO | WO-2019140448 A1 | 7/2019 |
| WO | WO-2019140449 A1 | 7/2019 |
| WO | WO-2019193141 A1 | 10/2019 |
| WO | WO-2019216883 A1 | 11/2019 |
| WO | WO-2019230183 A1 | 12/2019 |
| WO | WO-2019238180 A1 | 12/2019 |
| WO | WO-2019238181 A1 | 12/2019 |
| WO | WO-2019238182 A1 | 12/2019 |
| WO | WO-2019238195 A1 | 12/2019 |
| WO | WO-2019238196 A1 | 12/2019 |
| WO | WO-2019238197 A1 | 12/2019 |
| WO | WO-2019238198 A1 | 12/2019 |
| WO | WO-2020002416 A1 | 1/2020 |
| WO | WO-2020043806 A1 | 3/2020 |

OTHER PUBLICATIONS

Brief Communication—Letter from the Opponent O2 of Jul. 17, 2023 for European Patent No. 3681452, mailed Jul. 20, 2023, 20 pages.

Brief Communication—Letter from the Opponent of Jun. 9, 2023, for the European Patent No. 3681452, dated Jun. 14, 2023, 9 pages.

Cauwe M., et al., "Technology Development for a Low-Cost, Roll-to-Roll Chip Embedding Solution Based on PET Foils," 18th European Microelectronics and Packaging Conference (EMPC), IEEE, Sep. 12, 2011, 6 pages.

Communication of Further Notices of Opposition Pursuant to Rule 79(2) EPC represented by Ter Meer Steinmeister & Partner for European Patent No. 3681452, mailed on Oct. 19, 2022, 45 pages.

Communication of Further Notices of Opposition Pursuant to Rule 79(2) EPC represented by Cohausz & Florack for European Patent No. 3681452, mailed on Oct. 19, 2022, 36 pages.

Elson J., et al., "Wireless Sensor Networks: A New Regime for Time Synchronization," Computer Communication Review, vol. 33, No. 1, 2002, pp. 149-154.

Farooqui M.F., et al., "Low Cost Inkjet Printed Smart Bandage for Wireless Monitoring of Chronic Wounds," Scientific Reports, vol. 6, Jun. 29, 2016, 14 pages.

Geng Y., et al., "A Hybrid Low Power Biopatch for Body Surface Potential Measurement," IEEE Journal of Biomedical and Health Informatics, vol. 17, No. 3, May 1, 2013, pp. 591-599.

George J., et al., "Reliability of Plastic-Encapsulated Electronic Components in Supersaturated Steam Environments," IEEE Transactions on Components, Packaging and Manufacturing Technology, vol. 5 (10), Oct. 2015, pp. 1423-1431.

Iannetta, Jr. R.A., et al., "Successful Case Histories of Polymer Based Circuitry on Flexible Film Substrates," Electro/94 International Conference Proceedings Combined Volumes, IEEE, XP010149465, May 10-12, 1994, pp. 885-889.

International Search Report and Written Opinion for Application No. PCT/EP2018/074200, mailed on Jan. 11, 2019, 10 pages.

International Appl. No. PCT/EP2018/074200, International Preliminary Report on Patentability mailed Mar. 19, 2020, 8 pages.

Lamport L., "Time, Clocks, and the Ordering of Events in a Distributed System, "Communications of the ACM, vol. 21, No. 7, Jul. 1978, pp. 558-565, DOI: https://doi.org/10.1145/359545.359563.

Little Miss Plasters, kidstravelclub.co.uk., retrieved from http://www.kidstravelclub.co.uk/little-miss-girls-childrens-plasters on Aug. 26, 2016, 2 pages.

Lu B., et al., "A Study of the Autofluorescence of Parylene Materials for µTAS Applications," Lab on Chip, vol. 10 (14), Jul. 2010, pp. 1826-1834.

Mcleod A.J., et al., "Motion Magnification for Endoscopic Surgery," Progress in Biomedical Optics and Imaging, SPIE—International Society for Optical Engineering, Mar. 12, 2014, vol. 9036, 8 pages.

Mehmood N., et al., "Applications Of Modern Sensors And Wireless Technology In Effective Wound Management: Modern Sensors And Wireless Technology," Journal of Biomedical Materials Research Part B, vol. 102, May 1, 2014, XP055739544, pp. 885-895.

Mostafalu P., et al., "Wireless Flexible Smart Bandage For Continuous Monitoring Of Wound Oxygenation," IEEE Transactions on Biomedical Circuits and Systems, vol. 9 (5), Oct. 1, 2015, XP055526132, pp. 670-677 (8 pages).

Narusawa H., "The Corona Discharge Causes Short Destruction that had Bad Influence on a Power Switching Circuit," Adphox Corporation, Jan. 1, 2009, retrieved from http://www.adphox.co.jp/keisokuki/ke-english-corona/CORONA_DISCHARGE_EN.pdf, 12 pages.

Raviglione A., et al., "Real-Time Smart Textile-Based System to Monitor Pressure Offloading of Diabetic Foot Ulcers," Journal of Diabetes Science and Technology, vol. 11 (5), Sep. 2017, pp. 894-898.

Reply of the Patent Proprietor to the Notice of Opposition for European Patent No. EP3681452, mailed Feb. 28, 2023, 64 pages.

Romer K., Time Synchronization in Ad Hoc Networks, Dec. 31, 2001, 9 pages, Retrieved from the Internet: https://www.vs.inf.ethz.ch/publ/papers/mobihoc01-time-sync.pdf.

Rose D.P., et al., "Adhesive RFID Sensor Patch for Monitoring of Sweat Electrolytes," IEEE Transactions on Biomedical Engineering, vol. 62 (6), Jun. 2015, first published on Nov. 11, 2015, pp. 1457-1465.

Siddiqi M., et al., "Securing the Timestamping of Sensor Data from Wearable Healthcare Devices," Bodynets, Sep. 28-30, 2015 Sydney, Australia, Dol: 10.4108/eai.28-9-2015.2261552, 1 page.

Stojmenovic I., "Handbook Of Sensor Networks: Algorithms And Architectures," 2005, https://vdoc.pub/documents/handbook-of-sensor-networks-algorithmsand-architectures-5tn0p3pikip, 553 pages.

Wakita J., et al., "Variations in Optical Absorption and Fluorescence Spectra for Polyimide Thin Films Caused by Structural Isomerism," Journal of Photopolymer Science and Technology, Jan. 1, 2003, 1 page.

Wikipedia: "Logical Clock," version: Oct. 12, 2016, Retrieved from the Internet: https://en.wikipedia.org/w/index.php?title=Logical_clock&oldid=7 43934837, 2 pages.

Wikipedia: "Timestamp," Retrieved from the Internet: https://en.wikipedia.org/wiki/Timestamp , on Dec. 7, 2022, 3 pages.

Willis B., "Conformal Coating Inspection & Coating Faults," Vision Engineering, Jul. 21, 2016, retrieved from http://www.visioneng.com/wp-content/uploads/2017/11/Conformal-Coating-Inspection-and-Defects.21JUL16.pdf, 35 pages.

Willis B., "Guide to Conformal Coating & Cleaning Defects Contents," Mar. 1, 2014, retrieved from http://coatingguide.smartgroup.org/Files%20pdf/Coating%20Defects%20V2%2014March2014.pdf, vol. 1, 31 pages.

Yoneki E., et al., "Ubiquitous Computing: Challenges in Flexible Data Aggregation," EUC 2005, Lecture Notes in Computer Science, LNCS, 2005, vol. 3824, ISBN 978-3-540-30807-2, ISBN 3-540-30807-5, pp. 1189-1200, https://link.springer.com/chapter/10.1007/11596356_117.

Merriam-Webster, Definition of "Add," Retrieved from the Internet: URL: https://www.merriam-webster.com/dictionary/add, last updated on Jun. 23, 2023, 6 pages.

Transmittal of Decision Summons for the Opposition of European Patent No. 3681452, mailed on Dec. 18, 2023, 32 pages.

* cited by examiner

SENSOR ENABLED WOUND THERAPY DRESSINGS AND SYSTEMS IMPLEMENTING CYBERSECURITY

CROSS-REFERENCE TO RELATED APPLICATIONS

The present application is a continuation of U.S. patent application Ser. No. 16/645,779, filed on 9 Mar. 2020, which is a U.S. national stage application of International Patent Application No. PCT/EP2018/074200, filed on Sep. 7, 2018, which claims priority to U.S. Patent Application No. 62/556,504, filed on 10 Sep. 2017, U.S. Patent Application No. 62/556,505, filed on 11 Sep. 2017, U.S. Patent Application No. 62/586,833, filed on 15 Nov. 2017, and U.K. Patent Application No. 1718870.7, filed on 15 Nov. 2017, each of which in incorporated by reference in its entirety.

BACKGROUND

Field

Embodiments of the present disclosure relate to apparatuses, systems, and methods for the treatment of tissues via sensor-enabled monitoring in communication with various therapy regimes.

Description of the Related Art

Nearly all areas of medicine may benefit from improved information regarding the state of the tissue, organ, or system to be treated, particularly if such information is gathered in real-time during treatment. Many types of treatments are still routinely performed without the use of sensor data collection; instead, such treatments rely upon visual inspection by a caregiver or other limited means rather than quantitative sensor data. For example, in the case of wound treatment via dressings and/or negative pressure wound therapy, data collection is generally limited to visual inspection by a caregiver and often the underlying wounded tissue may be obscured by bandages or other visual impediments. Even intact, unwounded skin may have underlying damage that is not visible to the naked eye, such as a compromised vascular or deeper tissue damage that may lead to an ulcer. Similar to wound treatment, during orthopedic treatments requiring the immobilization of a limb with a cast or other encasement, only limited information is gathered on the underlying tissue. In instances of internal tissue repair, such as a bone plate, continued direct sensor-driven data collection is not performed. Further, braces and/or sleeves used to support musculoskeletal function do not monitor the functions of the underlying muscles or the movement of the limbs. Outside of direct treatments, common hospital room items such as beds and blankets could be improved by adding capability to monitor patient parameters.

Therefore, there is a need for improved sensor monitoring, particularly through the use of sensor-enabled substrates which can be incorporated into existing treatment regimes.

SUMMARY

In some embodiments, a wound monitoring and/or therapy apparatus includes a wound dressing configured to be positioned in contact with a wound, the wound dressing including one or more sensors configured to obtain measurement data of at least one of the wound or periwound and a controller configured to maintain a device clock indicative of a non-real time clock, receive measurement data obtained by the one or more sensors, and transmit measurement data to a remote computing device according to a security protocol, the security protocol comprising including the device clock associated with the measurement data in the transmission.

The apparats of the preceding paragraph can include one or more of the following features. The wound dressing can include a substantially flexible wound contact layer supporting the one or more sensors. The security protocol can further include encrypting the measurement data. The security protocol can further include not including in the transmission patient identification information or real time clock information associated with the measurement data. Transmission of the measurement data with the associated device clock data can causes the remote computing device to utilize the device clock data to correlate the measurement data with real time clock data. The controller can be further configured to transmit initial device clock data to the remote computing device during initialization, and transmission of the measurement data with the associated device clock data can cause the remote computing device to determine elapsed time relative to the initial transmission based on comparison of the initial device clock data and device clock data associated with the measurement data. The controller can be configured to maintain the device clock when power is supplied to the controller. The controller can be configured to maintain the device clock by counting up from zero, a random number, or a unique number. In response to a power interruption, the controller can be further configured to reestablish the device clock from a previous device clock value before the power interruption.

In some embodiments, a wound monitoring and/or therapy system includes the apparatus of any of the preceding paragraphs, a communication device configured to be connected to the controller of the apparatus and further configured to periodically receive data from the controller, and a computing device configured to be connected to the communication device, the computing device further configured to receive data from the communication device, the computing device further configured to be connected to another remote computing device configured to receive and aggregate data from the computing device.

The system of the preceding paragraph can include one or more of the following features. The system can further include another computing device configured to obtain one or more images of at least one of the wound or periwound. The computing device can be configured to communicate the one or more images to the another remote computing device. The wound dressing can further include an antenna configured to communicate the measurement data to at least one of the controller or communication device. The system can further include a skin perfusion measurement device configured to measure skin perfusion pressure in a target area of the patient, wherein the computing device is can be further configured to be connected to the perfusion measurement device and receive data from the perfusion measurement device. The communication device can be configured to be connected to the controller using near field communication (NFC) protocol.

In some embodiments, a method of operating a wound dressing configured to be positioned in contact with a wound, the wound dressing including one or more sensors configured to obtain measurement data of at least one of the wound or periwound, the method includes, by a controller configured to be connected to or supported by the wound dressing, maintaining a device clock indicative of a non-real time clock, receiving measurement data obtained by the one or more sensors, and transmitting measurement data to a remote computing device according to a security protocol by including the device clock associated with the measurement data in the transmission.

The method of the preceding paragraph can include one or more of the following features. The security protocol can further include encrypting the measurement data. The security protocol can further comprise not including in the transmission patient identification information or real time clock information associated with the measurement data. Transmission of the measurement data with the associated device clock data can cause the remote computing device to utilize the device clock data to correlate the measurement data with real time clock data. The method can include, by the controller, transmitting initial device clock data to the remote computing device during initialization, wherein transmission of the measurement data with the associated device clock data can cause the remote computing device to determine elapsed time relative to the initial transmission based on comparison of the initial device clock data and device clock data associated with the measurement data. The method can further include maintaining the device clock when power is supplied to the controller. Maintaining the device clock can be performed by counting up from zero, a random number, or a unique number. In response to a power interruption, the method can include reestablishing the device clock from a previous device clock value before the power interruption

BRIEF DESCRIPTION OF THE DRAWINGS

Embodiments of the present disclosure will now be described hereinafter, by way of example only, with reference to the accompanying drawings in which.

DETAILED DESCRIPTION

Figure 1A:
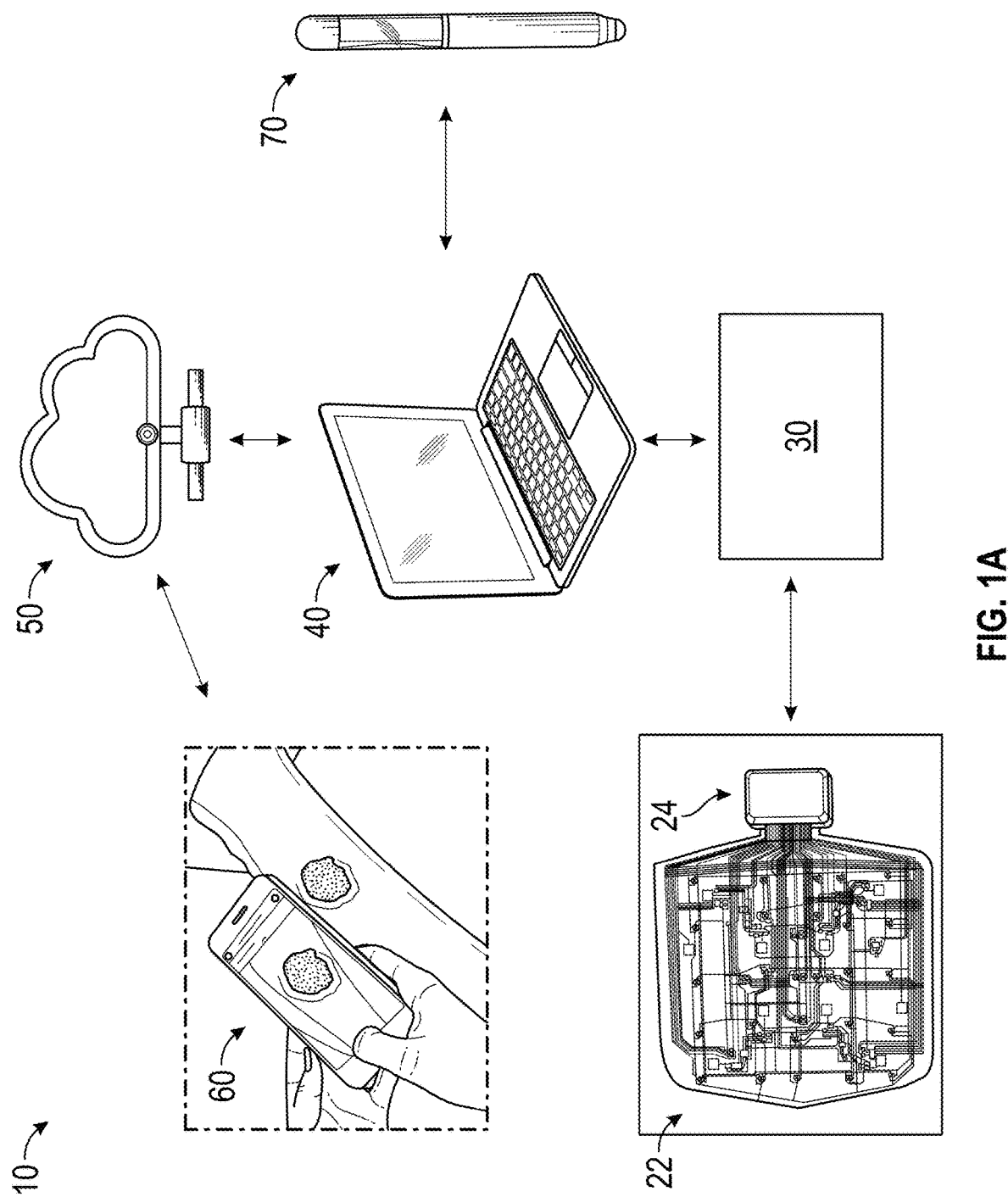
FIG. 1A illustrates a wound monitoring and therapy system according to some embodiments.

Embodiments disclosed herein relate to apparatuses and methods of monitoring and treating biological tissue with sensor-enabled substrates. The embodiments disclosed herein are not limited to treatment or monitoring of a particular type of tissue or injury, instead the sensor-enabled technologies disclosed herein are broadly applicable to any type of therapy that may benefit from sensor-enabled substrates. Some implementations utilize sensors and data collection relied upon by health care providers to make both diagnostic and patient management decisions.

Some embodiments disclosed herein relate to the use of sensors mounted on or embedded within substrates configured to be used in the treatment of both intact and damaged human or animal tissue. Such sensors may collect information about the surrounding tissue and transmit such information to a computing device or a caregiver to be utilized in further treatment. In certain embodiments, such sensors may be attached to the skin anywhere on the body, including areas for monitoring arthritis, temperature, or other areas that may be prone to problems and require monitoring. Sensors disclosed herein may also incorporate markers, such as radiopaque markers, to indicate the presence of the device, for example prior to performing an MRI or other technique.

The sensor embodiments disclosed herein may be used in combination with clothing. Non-limiting examples of clothing for use with embodiments of the sensors disclosed herein include shirts, pants, trousers, dresses, undergarments, outer-garments, gloves, shoes, hats, and other suitable garments. In certain embodiments, the sensor embodiments disclosed herein may be welded into or laminated into/onto the particular garments. The sensor embodiments may be printed directly onto the garment and/or embedded into the fabric. Breathable and printable materials such as microporous membranes may also be suitable.

Sensor embodiments disclosed herein may be incorporated into cushioning or bed padding, such as within a hospital bed, to monitor patient characteristics, such as any characteristic disclosed herein. In certain embodiments, a disposable film containing such sensors could be placed over the hospital bedding and removed/replaced as needed.

In some implementations, the sensor embodiments disclosed herein may incorporate energy harvesting, such that the sensor embodiments are self-sustaining. For example, energy may be harvested from thermal energy sources, kinetic energy sources, chemical gradients, or any suitable energy source.

The sensor embodiments disclosed herein may be utilized in rehabilitation devices and treatments, including sports medicine. For example, the sensor embodiments disclosed herein may be used in braces, sleeves, wraps, supports, and other suitable items. Similarly, the sensor embodiments disclosed herein may be incorporated into sporting equipment, such as helmets, sleeves, and/or pads. For example, such sensor embodiments may be incorporated into a protective helmet to monitor characteristics such as acceleration, which may be useful in concussion diagnosis.

The sensor embodiments disclosed herein may be used in coordination with surgical devices, for example, the NAVIO surgical system by Smith & Nephew Inc. In implementations, the sensor embodiments disclosed herein may be in communication with such surgical devices to guide placement of the surgical devices. In some implementations, the sensor embodiments disclosed herein may monitor blood flow to or away from the potential surgical site or ensure that there is no blood flow to a surgical site. Further surgical data may be collected to aid in the prevention of scarring and monitor areas away from the impacted area.

To further aid in surgical techniques, the sensors disclosed herein may be incorporated into a surgical drape to provide information regarding tissue under the drape that may not be immediately visible to the naked eye. For example, a sensor embedded flexible drape may have sensors positioned advantageously to provide improved area-focused data collection. In certain implementations, the sensor embodiments disclosed herein may be incorporated into the border or interior of a drape to create fencing to limit/control the surgical theater.

Sensor embodiments as disclosed herein may also be utilized for pre-surgical assessment. For example, such sensor embodiments may be used to collect information about a potential surgical site, such as by monitoring skin and the underlying tissues for a possible incision site. For example, perfusion levels or other suitable characteristics may be monitored at the surface of the skin and deeper in the tissue to assess whether an individual patient may be at risk for surgical complications. Sensor embodiments such as those disclosed herein may be used to evaluate the presence of microbial infection and provide an indication for the use of antimicrobials. Further, sensor embodiments disclosed herein may collect further information in deeper tissue, such as identifying pressure ulcer damage and/or the fatty tissue levels.

The sensor embodiments disclosed herein may be utilized in cardiovascular monitoring. For example, such sensor embodiments may be incorporated into a flexible cardiovascular monitor that may be placed against the skin to monitor characteristics of the cardiovascular system and communicate such information to another device and/or a caregiver. For example, such a device may monitor pulse rate, oxygenation of the blood, and/or electrical activity of the heart. Similarly, the sensor embodiments disclosed herein may be utilized for neurophysiological applications, such as monitoring electrical activity of neurons.

The sensor embodiments disclosed herein may be incorporated into implantable devices, such as implantable orthopedic implants, including flexible implants. Such sensor embodiments may be configured to collect information regarding the implant site and transmit this information to an external source. In some embodiments, an internal source may also provide power for such an implant.

The sensor embodiments disclosed herein may also be utilized for monitoring biochemical activity on the surface of the skin or below the surface of the skin, such as lactose buildup in muscle or sweat production on the surface of the skin. In some embodiments, other characteristics may be monitored, such as glucose concentration, urine concentration, tissue pressure, skin temperature, skin surface conductivity, skin surface resistivity, skin hydration, skin maceration, and/or skin ripping.

Sensor embodiments as disclosed herein may be incorporated into Ear, Nose, and Throat (ENT) applications. For example, such sensor embodiments may be utilized to monitor recovery from ENT-related surgery, such as wound monitoring within the sinus passage.

As described in greater detail below, the sensor embodiments disclosed herein may encompass sensor printing technology with encapsulation, such as encapsulation with a polymer film. Such a film may be constructed using any polymer described herein, such as polyurethane. Encapsulation of the sensor embodiments may provide waterproofing of the electronics and protection from local tissue, local fluids, and other sources of potential damage.

In certain embodiments, the sensors disclosed herein may be incorporated into an organ protection layer such as disclosed below. Such a sensor-embedded organ protection layer may both protect the organ of interest and confirm that the organ protection layer is in position and providing protection. Further, a sensor-embedded organ protection layer may be utilized to monitor the underlying organ, such as by monitoring blood flow, oxygenation, and other suitable markers of organ health. In some embodiments, a sensor-enabled organ protection layer may be used to monitor a transplanted organ, such as by monitoring the fat and muscle content of the organ. Further, sensor-enabled organ protection layers may be used to monitor an organ during and after transplant, such as during rehabilitation of the organ.

The sensor embodiments disclosed herein may be incorporated into treatments for wounds (disclosed in greater detail below) or in a variety of other applications. Non-limiting examples of additional applications for the sensor embodiments disclosed herein include: monitoring and treatment of intact skin, cardiovascular applications such as monitoring blood flow, orthopedic applications such as monitoring limb movement and bone repair, neurophysiological applications such as monitoring electrical impulses, and any other tissue, organ, system, or condition that may benefit from improved sensor-enabled monitoring.

Wound Therapy

Some embodiments disclosed herein relate to wound therapy for a human or animal body. Therefore, any reference to a wound herein can refer to a wound on a human or animal body, and any reference to a body herein can refer to a human or animal body. The disclosed technology embodiments may relate to preventing or minimizing damage to physiological tissue or living tissue, or to the treatment of damaged tissue (for example, a wound as described herein) wound with or without reduced pressure, including for example a source of negative pressure and wound dressing components and apparatuses. The apparatuses and components comprising the wound overlay and packing materials or internal layers, if any, are sometimes collectively referred to herein as dressings. In some embodiments, the wound dressing can be provided to be utilized without reduced pressure.

Some embodiments disclosed herein relate to wound therapy for a human or animal body. Therefore, any reference to a wound herein can refer to a wound on a human or animal body, and any reference to a body herein can refer to a human or animal body. The disclosed technology embodiments may relate to preventing or minimizing damage to physiological tissue or living tissue, or to the treatment of damaged tissue (for example, a wound as described herein).

As used herein the expression "wound" may include an injury to living tissue may be caused by a cut, blow, or other impact, typically one in which the skin is cut or broken. A wound may be a chronic or acute injury. Acute wounds occur as a result of surgery or trauma. They move through the stages of healing within a predicted timeframe. Chronic wounds typically begin as acute wounds. The acute wound can become a chronic wound when it does not follow the healing stages resulting in a lengthened recovery. It is believed that the transition from acute to chronic wound can be due to a patient being immuno-compromised.

Chronic wounds may include for example: venous ulcers (such as those that occur in the legs), which account for the majority of chronic wounds and mostly affect the elderly, diabetic ulcers (for example, foot or ankle ulcers), peripheral arterial disease, pressure ulcers, or epidermolysis bullosa (EB).

Examples of other wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Wounds may also include a deep tissue injury. Deep tissue injury is a term proposed by the National Pressure Ulcer Advisory Panel (NPUAP) to describe a unique form of pressure ulcers. These ulcers have been described by clinicians for many years with terms such as purple pressure ulcers, ulcers that are likely to deteriorate and bruises on bony prominences.

Wound may also include tissue at risk of becoming a wound as discussed herein. For example, tissue at risk may include tissue over a bony protuberance (at risk of deep tissue injury/insult) or pre-surgical tissue (for example, knee tissue) that may has the potential to be cut (for example, for joint replacement/surgical alteration/reconstruction).

Some embodiments relate to methods of treating a wound with the technology disclosed herein in conjunction with one or more of the following: advanced footwear, turning a patient, offloading (such as, offloading diabetic foot ulcers), treatment of infection, systemix, antimicrobial, antibiotics, surgery, removal of tissue, affecting blood flow, physiotherapy, exercise, bathing, nutrition, hydration, nerve stimulation, ultrasound, electrostimulation, oxygen therapy, microwave therapy, active agents ozone, antibiotics, antimicrobials, or the like.

Alternatively or additionally, a wound may be treated using topical negative pressure and/or traditional advanced wound care, which is not aided by the using of applied negative pressure (may also be referred to as non-negative pressure therapy).

Advanced wound care may include use of an absorbent dressing, an occlusive dressing, use of an antimicrobial and/or debriding agents in a wound dressing or adjunct, a pad (for example, a cushioning or compressive therapy, such as stockings or bandages), or the like.

In some embodiments, treatment of such wounds can be performed using traditional wound care, wherein a dressing can be applied to the wound to facilitate and promote healing of the wound.

Some embodiments relate to methods of manufacturing a wound dressing comprising providing a wound dressing as disclosed herein.

The wound dressings that may be utilized in conjunction with the disclosed technology include any known dressing in the art. The technology is applicable to negative pressure therapy treatment as well as non-negative pressure therapy treatment.

In some embodiments, a wound dressing comprises one or more absorbent layer(s). The absorbent layer may be a foam or a superabsorbent.

In some embodiments, wound dressings may comprise a dressing layer including a polysaccharide or modified polysaccharide, a polyvinylpyrrolidone, a polyvinyl alcohol, a polyvinyl ether, a polyurethane, a polyacrylate, a polyacrylamide, collagen, or gelatin or mixtures thereof. Dressing layers comprising the polymers listed are known in the art as being useful for forming a wound dressing layer for either negative pressure therapy or non-negative pressure therapy.

In some embodiments, the polymer matrix may be a polysaccharide or modified polysaccharide.

In some embodiments, the polymer matrix may be a cellulose. Cellulose material may include hydrophilically modified cellulose such as methyl cellulose, carboxymethyl cellulose (CMC), carboxymethyl cellulose (CEC), ethyl cellulose, propyl cellulose, hydroxyethyl cellulose, hydroxypropyl cellulose, hydroxypropylmethyl cellulose, carboxyethyl sulphonate cellulose, cellulose alkyl sulphonate, or mixtures thereof.

In certain embodiments, cellulose material may be cellulose alkyl sulphonate. The alkyl moiety of the alkyl sulphonate substituent group may have an alkyl group having 1 to 6 carbon atoms, such as methyl, ethyl, propyl, or butyl. The alkyl moiety may be branched or unbranched, and hence suitable propyl sulphonate substituents may be 1- or 2-methyl-ethylsulphonate. Butyl sulphonate substituents may be 2-ethyl-ethylsulphonate, 2,2-dimethyl-ethylsulphonate, or 1,2-dimethyl-ethylsulphonate. The alkyl sulphonate substituent group may be ethyl sulphonate. The cellulose alkyl sulphonate is described in WO10061225, US2016/114074, US2006/0142560, or U.S. Pat. No. 5,703,225, the disclosures of which are hereby incorporated by reference in their entirety.

Cellulose alkyl sulfonates may have varying degrees of substitution, the chain length of the cellulose backbone structure, and the structure of the alkyl sulfonate substituent. Solubility and absorbency are largely dependent on the degree of substitution: as the degree of substitution is increased, the cellulose alkyl sulfonate becomes increasingly soluble. It follows that, as solubility increases, absorbency increases.

In some embodiments, a wound dressing also comprises a top or cover layer.

The thickness of the wound dressing disclosed herein may be between 1 to 20, or 2 to 10, or 3 to 7 mm.

In some embodiments, the disclosed technology may be used in conjunction with a non-negative pressure dressing. A non-negative pressure wound dressing suitable for providing protection at a wound site may comprise:

an absorbent layer for absorbing wound exudate and an obscuring element for at least partially obscuring a view of wound exudate absorbed by the absorbent layer in use.

The obscuring element may be partially translucent.

The obscuring element may be a masking layer.

The non-negative pressure wound dressing may further comprise a region in or adjacent the obscuring element for allowing viewing of the absorbent layer. For example, the obscuring element layer may be provided over a central region of the absorbent layer and not over a border region of the absorbent layer. In some embodiments, the obscuring element is of hydrophilic material or is coated with a hydrophilic material.

The obscuring element may comprise a three-dimensional knitted spacer fabric. The spacer fabric is known in the art and may include a knitted spacer fabric layer.

The obscuring element may further comprise an indicator for indicating the need to change the dressing.

In some embodiments, the obscuring element is provided as a layer at least partially over the absorbent layer, further from a wound site than the absorbent layer in use.

The non-negative pressure wound dressing may further comprise a plurality of openings in the obscuring element for allowing fluid to move therethrough. The obscuring element may comprise, or may be coated with, a material having size-exclusion properties for selectively permitting or preventing passage of molecules of a predetermined size or weight.

The obscuring element may be configured to at least partially mask light radiation having wavelength of 600 nm and less.

The obscuring element may be configured to reduce light absorption by 50% or more.

The obscuring element may be configured to yield a CIE L* value of 50 or more, and optionally 70 or more. In some embodiments, the obscuring element may be configured to yield a CIE L* value of 70 or more.

In some embodiments, the non-negative pressure wound dressing may further comprise at least one of a wound contact layer, a foam layer, an odor control element, a pressure-resistant layer and a cover layer.

In some embodiments, the cover layer is present, and the cover layer is a translucent film. Typically, the translucent film has a moisture vapour permeability of 500 g/m2/24 hours or more.

The translucent film may be a bacterial barrier.

In some embodiments, the non-negative pressure wound dressing as disclosed herein comprises the wound contact layer and the absorbent layer overlies the wound contact layer. The wound contact layer carries an adhesive portion for forming a substantially fluid tight seal over the wound site.

The non-negative pressure wound dressing as disclosed herein may comprise the obscuring element and the absorbent layer being provided as a single layer.

In some embodiments, the non-negative pressure wound dressing disclosed herein comprises the foam layer, and the obscuring element is of a material comprising components that may be displaced or broken by movement of the obscuring element.

In some embodiments, the non-negative pressure wound dressing comprises an odor control element, and in another embodiment the dressing does not include an odor control element. When present, the odor control element may be dispersed within or adjacent the absorbent layer or the obscuring element. Alternatively, when present the odor control element may be provided as a layer sandwiched between the foam layer and the absorbent layer.

In some embodiments, the disclosed technology for a non-negative pressure wound dressing comprises a method of manufacturing a wound dressing, comprising: providing an absorbent layer for absorbing wound exudate; and providing an obscuring element for at least partially obscuring a view of wound exudate absorbed by the absorbent layer in use.

In some embodiments, the non-negative pressure wound dressing is may be suitable for providing protection at a wound site, comprising: an absorbent layer for absorbing wound exudate; and a shielding layer provided over the absorbent layer, and further from a wound-facing side of the wound dressing than the absorbent layer. The shielding layer may be provided directly over the absorbent layer. In some embodiments, the shielding layer comprises a three-dimensional spacer fabric layer.

The shielding layer increases the area over which a pressure applied to the dressing is transferred by 25% or more or the initial area of application. For example the shielding layer increases the area over which a pressure applied to the dressing is transferred by 50% or more, and optionally by 100% or more, and optionally by 200% or more.

The shielding layer may comprise 2 or more sub-layers, wherein a first sub-layer comprises through holes and a further sub-layer comprises through holes and the through holes of the first sub-layer are offset from the through holes of the further sub-layer.

The non-negative pressure wound dressing as disclosed herein may further comprise a permeable cover layer for allowing the transmission of gas and vapour therethrough, the cover layer provided over the shielding layer, wherein through holes of the cover layer are offset from through holes of the shielding layer.

The non-negative pressure wound dressing may be suitable for treatment of pressure ulcers.

A more detailed description of the non-negative pressure dressing disclosed hereinabove is provided in WO2013007973, the entirety of which is hereby incorporated by reference.

In some embodiments, the non-negative pressure wound dressing may be a multi-layered wound dressing comprising: a fibrous absorbent layer for absorbing exudate from a wound site; and a support layer configured to reduce shrinkage of at least a portion of the wound dressing.

In some embodiments, the multi-layered wound dressing disclosed herein, further comprises a liquid impermeable film layer, wherein the support layer is located between the absorbent layer and the film layer.

The support layer disclosed herein may comprise a net. The net may comprise a geometric structure having a plurality of substantially geometric apertures extending therethrough. The geometric structure may for example comprise a plurality of bosses substantially evenly spaced and joined by polymer strands to form the substantially geometric apertures between the polymer strands.

The net may be formed from high density polyethylene.

The apertures may have an area from 0.005 to 0.32 mm2.

The support layer may have a tensile strength from 0.05 to 0.06 Nm.

The support layer may have a thickness of from 50 to 150 µm.

In some embodiments, the support layer is located directly adjacent the absorbent layer. Typically, the support layer is bonded to fibers in a top surface of the absorbent layer. The support layer may further comprise a bonding layer, wherein the support layer is heat laminated to the fibers in the absorbent layer via the bonding layer. The bonding layer may comprise a low melting point adhesive such as ethylene-vinyl acetate adhesive.

In some embodiments, the multi-layered wound dressing disclosed herein further comprises an adhesive layer attaching the film layer to the support layer.

In some embodiments, the multi-layered wound dressing disclosed herein further comprises a wound contact layer located adjacent the absorbent layer for positioning adjacent a wound. The multi-layered wound dressing may further comprise a fluid transport layer between the wound contact layer and the absorbent layer for transporting exudate away from a wound into the absorbent layer.

A more detailed description of the multi-layered wound dressing disclosed hereinabove is provided in GB patent application filed on 28 Oct. 2016 with application number GB1618298.2, the entirety of which is hereby incorporated by reference.

In some embodiments, the disclosed technology may be incorporated in a wound dressing comprising a vertically lapped material comprising: a first layer of an absorbing layer of material, and a second layer of material, wherein the first layer being constructed from at least one layer of non-woven textile fibers, the non-woven textile fibers being folded into a plurality of folds to form a pleated structure. In some embodiments, the wound dressing further comprises a second layer of material that is temporarily or permanently connected to the first layer of material.

Typically the vertically lapped material has been slitted.

In some embodiments, the first layer has a pleated structure having a depth determined by the depth of pleats or by the slitting width. The first layer of material may be a moldable, lightweight, fiber-based material, blend of material or composition layer.

The first layer of material may comprise one or more of manufactured fibers from synthetic, natural or inorganic polymers, natural fibers of a cellulosic, proteinaceous or mineral source.

The wound dressing may comprise two or more layers of the absorbing layer of material vertically lapped material stacked one on top of the other, wherein the two or more layers have the same or different densities or composition.

The wound dressing may in some embodiments comprise only one layer of the absorbing layer of material vertically lapped material.

The absorbing layer of material is a blend of natural or synthetic, organic or inorganic fibers, and binder fibers, or bicomponent fibers typically PET with a low melt temperature PET coating to soften at specified temperatures and to act as a bonding agent in the overall blend.

In some embodiments, the absorbing layer of material may be a blend of 5 to 95% thermoplastic polymer, and 5 to 95 wt % of a cellulose or derivative thereof.

In some embodiments, the wound dressing disclosed herein has a second layer comprises a foam or a dressing fixative.

The foam may be a polyurethane foam. The polyurethane foam may have an open or closed pore structure.

The dressing fixative may include bandages, tape, gauze, or backing layer.

In some embodiments, the wound dressing as disclosed herein comprises the absorbing layer of material connected directly to a second layer by lamination or by an adhesive, and the second layer is connected to a dressing fixative layer. The adhesive may be an acrylic adhesive, or a silicone adhesive.

In some embodiments, the wound dressing as disclosed herein further comprises layer of a superabsorbent fiber, or a viscose fiber or a polyester fiber.

In some embodiments, the wound dressing as disclosed herein further comprises a backing layer. The backing layer may be a transparent or opaque film. Typically the backing layer comprises a polyurethane film (typically a transparent polyurethane film).

A more detailed description of the multi-layered wound dressing disclosed hereinabove is provided in GB patent applications filed on 12 Dec. 2016 with application number GB1621057.7; and 22 Jun. 2017 with application number GB1709987.0, the entirety of each of which is hereby incorporated by reference.

In some embodiments, the non-negative pressure wound dressing may comprise an absorbent component for a wound dressing, the component comprising a wound contacting layer comprising gel forming fibers bound to a foam layer, wherein the foam layer is bound directly to the wound contact layer by an adhesive, polymer based melt layer, by flame lamination or by ultrasound.

The absorbent component may be in a sheet form.

The wound contacting layer may comprise a layer of woven or non-woven or knitted gel forming fibers.

The foam layer may be an open cell foam, or closed cell foam, typically an open cell foam. The foam layer is a hydrophilic foam.

The wound dressing may comprise the component that forms an island in direct contact with the wound surrounded by periphery of adhesive that adheres the dressing to the wound. The adhesive may be a silicone or acrylic adhesive, typically a silicone adhesive.

The wound dressing may be covered by a film layer on the surface of the dressing furthest from the wound.

A more detailed description of the wound dressing of this type hereinabove is provided in EP2498829, the entirety of which is hereby incorporated by reference.

In some embodiments, the non-negative pressure wound dressing may comprise a multi layered wound dressing for use on wounds producing high levels of exudate, characterized in that the dressing comprising: a transmission layer having an MVTR of at least 300 gm2/24 hours, an absorbent core comprising gel forming fibers capable of absorbing and retaining exudate, a wound contacting layer comprising gel forming fibers which transmits exudate to the absorbent core and a keying layer positioned on the absorbent core, the absorbent core and wound contacting layer limiting the lateral spread of exudate in the dressing to the region of the wound.

The wound dressing may be capable of handling at least 6 g (or 8 g and 15 g) of fluid per 10 cm2 of dressing in 24 hours.

The wound dressing may comprise gel forming fibers that are chemically modified cellulosic fibers in the form of a fabric. The fibers may include carboxymethylated cellulose fibers, typically sodium carboxymethylcellulose fiber.

The wound dressing may comprise a wound contact layer with a lateral wicking rate from 5 mm per minute to 40 mm per minute. The wound contact layer may have a fiber density between 25 gm2 and 55 gm2, such as 35 gm2.

The absorbent core may have an absorbency of exudate of at least 10 g/g, and typically a rate of lateral wicking of less the 20 mm per minute.

The absorbent core may have a blend in the range of up to 25% cellulosic fibers by weight and 75% to 100% gel forming fibers by weight.

Alternatively, the absorbent core may have a blend in the range of up to 50% cellulosic fibers by weight and 50% to 100% gel forming fibers by weight. For example the blend is in the range of 50% cellulosic fibers by weight and 50% gel forming fibers by weight.

The fiber density in the absorbent core may be between 150 gm2 and 250 gm2, or about 200 gm2.

The wound dressing when wet may have shrinkage that is less than 25% or less than 15% of its original size/dimension.

The wound dressing may comprise a transmission layer and the layer is a foam. The transmission layer may be a polyurethane foam laminated to a polyurethane film.

The wound dressing may comprise one or more layers selected from the group comprising a soluble medicated film layer; an odor-absorbing layer; a spreading layer and an additional adhesive layer.

The wound dressing may be 2 mm and 4 mm thick.

The wound dressing may be characterized in that the keying layer bonds the absorbent core to a neighboring layer. In some embodiments, the keying layer may be positioned on either the wound facing side of the absorbent core or the non-wound facing side of the absorbent core. In some embodiments, the keying layer is positioned between the absorbent core and the wound contact layer. The keying layer is a polyamide web.

A more detailed description of the wound dressing of this type hereinabove is provided in EP1718257, the entirety of which is hereby incorporated by reference.

In some embodiments, the non-negative pressure wound dressing may be a compression bandage. Compression bandages are known for use in the treatment of oedema and other venous and lymphatic disorders, e.g., of the lower limbs.

A compression bandage systems typically employ multiple layers including a padding layer between the skin and the compression layer or layers. The compression bandage may be useful for wounds such as handling venous leg ulcers.

The compression bandage in some embodiments may comprise a bandage system comprising an inner skin facing layer and an elastic outer layer, the inner layer comprising a first ply of foam and a second ply of an absorbent nonwoven web, the inner layer and outer layer being sufficiently elongated so as to be capable of being wound about a patient's limb. A compression bandage of this type is disclosed in WO99/58090, the entirety of which is hereby incorporated by reference.

In some embodiments, the compression bandage system comprises: a) an inner skin facing, elongated, elastic bandage comprising: (i) an elongated, elastic substrate, and (ii) an elongated layer of foam, said foam layer being affixed to a face of said substrate and extending 33% or more across said face of substrate in transverse direction and 67% or more across said face of substrate in longitudinal direction; and b) an outer, elongated, self-adhering elastic bandage; said bandage having a compressive force when extended; wherein, in use, said foam layer of the inner bandage faces the skin and the outer bandage overlies the inner bandage. A compression bandage of this type is disclosed in WO2006/110527, the entirety of which is hereby incorporated by reference.

In some embodiments other compression bandage systems such as those disclosed in U.S. Pat. No. 6,759,566 and US 2002/0099318, the entirety of each of which is hereby incorporated by reference.

Negative Pressure Wound Dressing

In some embodiments, treatment of such wounds can be performed using negative pressure wound therapy, wherein a reduced or negative pressure can be applied to the wound to facilitate and promote healing of the wound. It will also be appreciated that the wound dressing and methods as disclosed herein may be applied to other parts of the body, and are not necessarily limited to treatment of wounds.

It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

Negative pressure therapy can be used for the treatment of open or chronic wounds that are too large to spontaneously close or otherwise fail to heal by means of applying negative pressure to the site of the wound. Topical negative pressure (TNP) therapy or negative pressure wound therapy (NPWT) involves placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines or bacteria.

Some of the dressings used in NPWT can include many different types of materials and layers, for example, gauze, pads, foam pads or multi-layer wound dressings. One example of a multi-layer wound dressing is the PICO dressing, available from Smith & Nephew, includes a wound contact layer and a superabsorbent layer beneath a backing layer to provide a canister-less system for treating a wound with NPWT. The wound dressing may be sealed to a suction port providing connection to a length of tubing, which may be used to pump fluid out of the dressing or to transmit negative pressure from a pump to the wound dressing. Additionally, RENASYS-F, RENASYS-G, RENASYS-AB, and RENASYS-F/AB, available from Smith & Nephew, are additional examples of NPWT wound dressings and systems. Another example of a multi-layer wound dressing is the ALLEVYN Life dressing, available from Smith & Nephew, which includes a moist wound environment dressing that is used to treat the wound without the use of negative pressure.

As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (such as, −40 mmHg is less than −60 mmHg). Negative pressure that is "more" or "greater" than −X mmHg corresponds to pressure that is further from atmospheric pressure (such as, −80 mmHg is more than −60 mmHg). In some embodiments, local ambient atmospheric pressure is used as a reference point, and such local atmospheric pressure may not necessarily be, for example, 760 mmHg.

The negative pressure range for some embodiments of the present disclosure can be approximately −80 mmHg, or between about −20 mmHg and −200 mmHg. Note that these pressures are relative to normal ambient atmospheric pressure, which can be 760 mmHg. Thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus.

In some embodiments of wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, or in synchronization with one or more patient physiological indices (such as, heartbeat). Examples of such applications where additional disclosure relating to the preceding may be found include U.S. Pat. No. 8,235,955, titled "Wound treatment apparatus and method," issued on Aug. 7, 2012; and U.S. Pat. No. 7,753,894, titled "Wound cleansing apparatus with stress," issued Jul. 13, 2010. The disclosures of both of these patents are hereby incorporated by reference in their entirety.

Embodiments of the wound dressings, wound dressing components, wound treatment apparatuses and methods described herein may also be used in combination or in addition to those described in International Application No. PCT/IB2013/001469, filed May 22, 2013, published as WO 2013/175306 A2 on Nov. 28, 2013, titled "APPARATUSES AND METHODS FOR NEGATIVE PRESSURE WOUND THERAPY," U.S. patent application Ser. No. 14/418,908, filed Jan. 30, 2015, published as US 2015/0190286 A1 on Jul. 9, 2015, titled "WOUND DRESSING AND METHOD OF TREATMENT," the disclosures of which are hereby incorporated by reference in their entireties. Embodiments of the wound dressings, wound dressing components, wound treatment apparatuses and methods described herein may also be used in combination or in addition to those described in U.S. patent application Ser. No. 13/092,042, filed Apr. 21, 2011, published as US2011/0282309, titled "WOUND DRESSING AND METHOD OF USE," and U.S. patent application Ser. No. 14/715,527, filed May 18, 2015, published as US2016/0339158 A1 on Nov. 24, 2016, titled "FLUIDIC CONNECTOR FOR NEGATIVE PRESSURE WOUND THERAPY," the disclosure of each of which is hereby incorporated by reference in its entirety, including further details relating to embodiments of wound dressings, the wound dressing components and principles, and the materials used for the wound dressings.

Additionally, some embodiments related to TNP wound treatment comprising a wound dressing in combination with a pump or associated electronics described herein may also be used in combination or in addition to those described in International Application PCT/EP2016/059329 filed Apr. 26, 2016, published as WO 2016/174048 on Nov. 3, 2016, entitled "REDUCED PRESSURE APPARATUS AND METHODS," the disclosure of which is hereby incorporated by reference in its entirety.

Sensor Enabled Wound Monitoring and Therapy System

FIG. 1A illustrates a wound monitoring and therapy system 10 according to some embodiments. The system includes a sensor enabled wound dressing 22 connected to a controller 24. As is described herein, the dressing 22 can be placed on or in a wound of a patient and can utilize various sensors embedded or otherwise placed in the dressing 22 to collect measurement data from one or more of the wound or areas surrounding the wound, such as the periwound (which can include intact skin). The controller 24 can receive, store, and process data collected by the dressing 22. To facilitate communication, the dressing 22 can include one or more communication modules, such as one or more antennas as described herein. In some cases, the controller 24 can transmit one or more of commands and data to the dressing 22.

In some embodiments, wound dressing 22 can be disposable and controller 24 can be reusable. In some embodiments, wound dressing 22 can be reusable. In some embodiments, wound dressing 22 can be re-sterilized or otherwise sanitized or disinfected. In some embodiments, controller 24 can be disposable. In some embodiments, wound dressing 22 and controller 24 can be permanently connected and the combined wound dressing and control box be disposable, or reusable or re-sterilized or otherwise sanitized or disinfected. The controller 24 can be positioned on the wound dressing 22. The controller 24 can be spatially separated from the wound dressing 22, such as by a cable or another wired or wireless electrical connection. The controller 24 can include a power source (such as a battery), one or more processors, one or more data storage elements, and a communication device. In some embodiments, the controller 24 can include one or more sensors, such as a temperature sensor or optical sensor to gather information on patient or environmental conditions located away from the wound dressing 22. In some embodiments, the one or more sensors of the controller 24 can include an accelerometer, motion sensor or gyroscope.

In some embodiments, the wound dressing 22 can include one or more indicators to communicate information to a user. The indicators can be visual, audible, haptic, or tactile. Communicated information can include measurement data, wound status, or the like.

The controller 24 can communicate data to a communication device 30 as requested, periodically, or the like. Communication can be performed over a wired or wireless interface, such as via near field communication (NFC), RFID, or the like when the communication device is placed in communication range. For example, communication range can be close proximity, such as within approximately 3 cm or less or more, to the controller 24. Communication device 30 can be placed in communication range by a clinician, such as during initialization and at the end of treatment. The controller 24 can respond with data to a command from the communication device 30 requesting data. Communication can be performed via transfer of hardware or data storage, such as one or more memory storage devices (for example, SD card). In some cases, communication can be performed non-electronically, such as visually, audibly, or tactilely, and one or more of the controller 24 or communication device 30 can provide an interface for such non-electronic communication of data.

The communication device 30 can be connected via a wired or wireless interface to a computing device 40, such as a personal computer, tablet, smartphone, or the like. For example, wired USB protocol can be used for communication of data between devices 30 and 40. As another example, communication of data can be performed via transfer of hardware or data storage, such as one or more memory storage devices (for example, SD card). In some cases, communication of data can be performed non-electronically, such as visually, audibly, or tactilely, and one or more of the communication device 30 or computing device 40 can provide an interface for such non-electronic communication of data.

Computing device 40 can further process data collected by the dressing 22. For example, the computing device 40 can aggregate data collected from the dressing 22 and perfusion determination device 70, which is configured to determine skin perfusion pressure and communicate data to the computing device 40 via a wired or wireless interface. For example, wired USB protocol can be used for communication between devices 70 and 40.

Computing device 40 can be configured to communicate via a wired or wireless interface with a remote computing device 50 that stores and processes medical data. In some embodiments, remote computing device 50 can be a cloud computing device, which includes one or more of remote storage, server, processing device, or any means of information storage. For example, remote computing device 50 can process and store medical data according with one or more applicable security and privacy standards, such as Health Insurance Portability & Accountability Act (HIPPA), European Union's Directive on Data Protection, or the like. Remote computing device 50 can make data provided by one or more of the computing device 40 or the mobile device 60 available for remote accessing and viewing, such as on a mobile device 60. In certain implementations, additional data can be added for storage on the remote computing device 50. For example, additional data can be added by the mobile device 60 via a dedicated app, web browser interface, or the like. The remote computing device 50 can process the data from one or more of the wound dressing 22, perfusion determination device 70, or the mobile device and assess or determine treatment plan, such as suggest or adjust one or more treatment therapies.

As described herein, mobile device 60 can take one or more images of a patient's wound. Such data can be transmitted via wired or wireless interface to the remote computing device 50. Although a smartphone is illustrated, mobile device 60 can be any suitable computing device that includes imaging functionality, such as a camera. Mobile device 60 can also collect additional data, such as data input by a healthcare provider in response to a questionnaire.

Various components illustrated in FIG. 1A are described in more detail in other portions of the present disclosure.

Figure 1B:
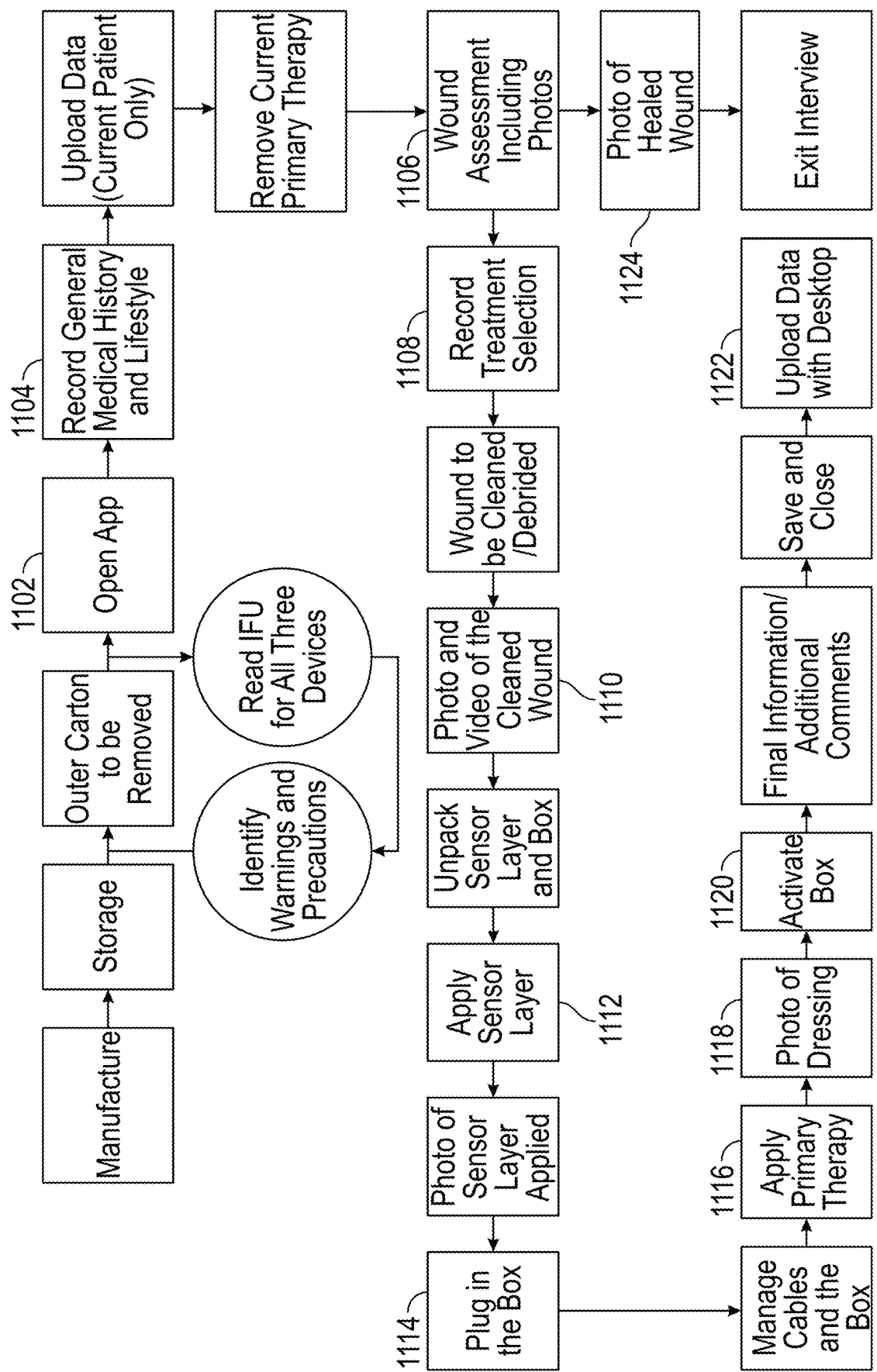
FIG. 1B illustrate the use of a wound monitoring and therapy system according to some embodiments.

FIG. 1B illustrates the use of a wound monitoring and therapy system, such as the system 10, according to some embodiments. As is illustrated, in blocks 1102 and 1104, a user (such as, healthcare provider (HCP)), can provide information regarding patient's medical history and lifestyle. Such information can be provided via the mobile device 60 for storage on the remote computing device 50 as described herein (such as, via an app). In block 1106, assessment of the wound can be performed. For example, images of the wound can be taken by the mobile device 60 and uploaded to the remote computing device 50 as described herein. Alternatively or additionally, skin perfusion pressure can be measured by the device 70 and uploaded to the remote computing device 50 as described herein.

In block 1108, treatment decision of the user can be recorded. For example, one or more treatment therapies can be selected, such as negative pressure wound therapy. In block 1110, additional images of the clean and, if applicable, debrided wound can be taken and uploaded to the remote computing device. In block 1112, wound dressing 22 can be placed in or on wound of the patient. In block 1114, controller 24 can be connected to the wound dressing 22, in cases where the wound dressing and controller are separate. The wound dressing can be initialized as described herein. In block 1116, one or more selected therapies can be applied. In block 1118, images of the wound covered by the wound dressing 22 can be taken and uploaded. In block 1120, measurement data from the wound dressing 22 can be collected and stored, as described herein. This step can be performed as many times as suitable while the wound dressing 22 is applied to the patient. Upon completion of therapy, in block 1122, measurement data can be uploaded to the remote computing device 50 as described herein. In block 1124, images of healed wound can be taken.

In some embodiments, one or more images of the wound can be processed using Eulerian magnification techniques described in U.S. Provisional Patent Application Nos. 62/506,524, titled NEGATIVE PRESSURE WOUND THERAPY SYSTEM USING EULERIAN VIDEO MAGNIFICATION, filed on 15 May 2017 and 62/506,551, titled WOUND ANALYSIS DEVICE AND METHOD, filed on 15 May 2017, each of which is incorporated by reference in its entirety. Eulerian magnification techniques can be implemented by any of the components of the system 10, such as the mobile device 60 or remote computing device 50.

Sensor Enabled Wound Dressing

Figure 1C:
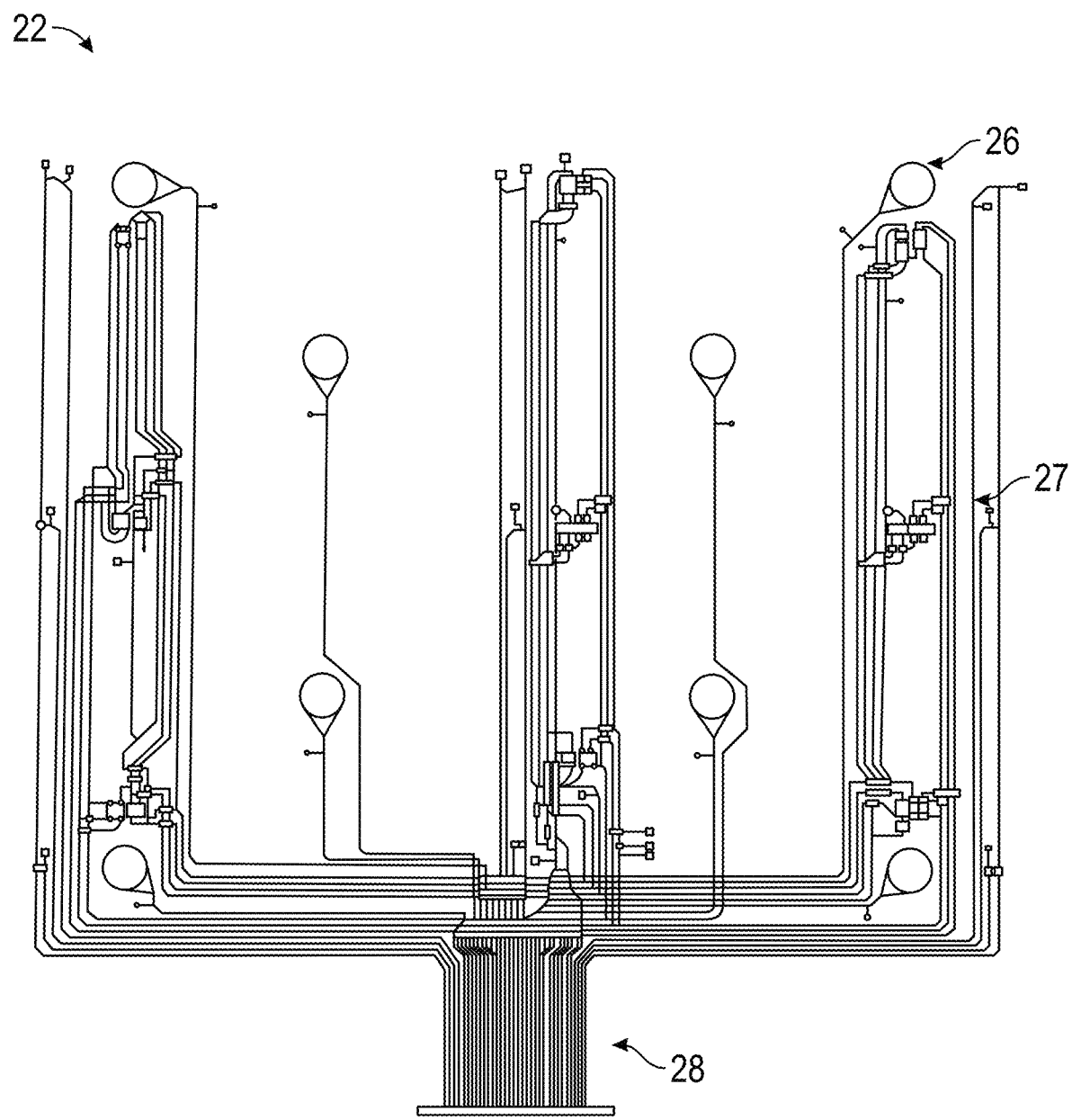
FIGS. 1C-1H illustrate sensor enabled wound dressings according to some embodiments.

FIG. 1C illustrates sensor enabled wound dressing 22 according to some embodiments. As described herein, the wound dressing 22 can include a substantially flexible wound contact layer, which can include one or more features of any of the wound contact layers described herein. The wound dressing 22 can include any of the wound dressing layers described herein. The entire wound dressing 22 can be substantially flexible. As is illustrated, one or more sensors 26 connected by one or more electrical connections or tracks 27 are positioned on or embedded in the wound dressing 22. For example, the one or more sensors and connections can be positioned on the wound contact layer. Also illustrated is a connector 28 for connecting to wound dressing 22 to the controller 24. The connector 28 includes one or more electrical connections or tracks. In some implementations, borders or edges of the wound contact layer can be smoothed by cuts, have smooth contours, include fibers, and/or the like to improve patient comfort.

In some implementations, borders or edges of the wound contact layer can be smoothed by cuts, have smooth contours, include fibers, and/or the like to improve patient comfort.

In some embodiments, the dressing can include one or more antennas for wireless communication. For example, one or more antennas can be printed as one or more connections or traces on the wound contact layer. The one or more antennas can be used to communicate measurement data collected by the one or more sensors without the controller 24. The one or more antennas can additionally be used to receive power wirelessly from a power source. In certain cases, the one or more antenna traces can be positioned on a substantially non-stretchable material (as described herein) such that the resonant frequencies of the one or more antennas remain fixed when the wound dressing 22 is placed under stress when in use on a patient. Fixing the one or more resonant frequencies can be advantageous for certain communication protocols, such as RFID.

In some embodiments, one or more sensors of the wound dressing 22 or any other wound dressing disclosed herein can measure one or more of impedance, capacitance, electrical sensing, temperature, pH, pressure (such as, by using a strain gauge), elasticity of tissue (such as, by using an ultrasound sensor, piezoelectric transducer, or the like, blood flow (such as, by measuring the Doppler effect), color, or light. One or more sensors can be electronic or non-electronic. Examples of non-electronic sensors include sensors that change color as a function of pH or when stretched, strained, or otherwise subjected to pressure. Measurements of such sensors can be obtained through visual monitoring, which can be performed automatically, such as by using a camera or by using one or more optical sensors.

Figure 1D:
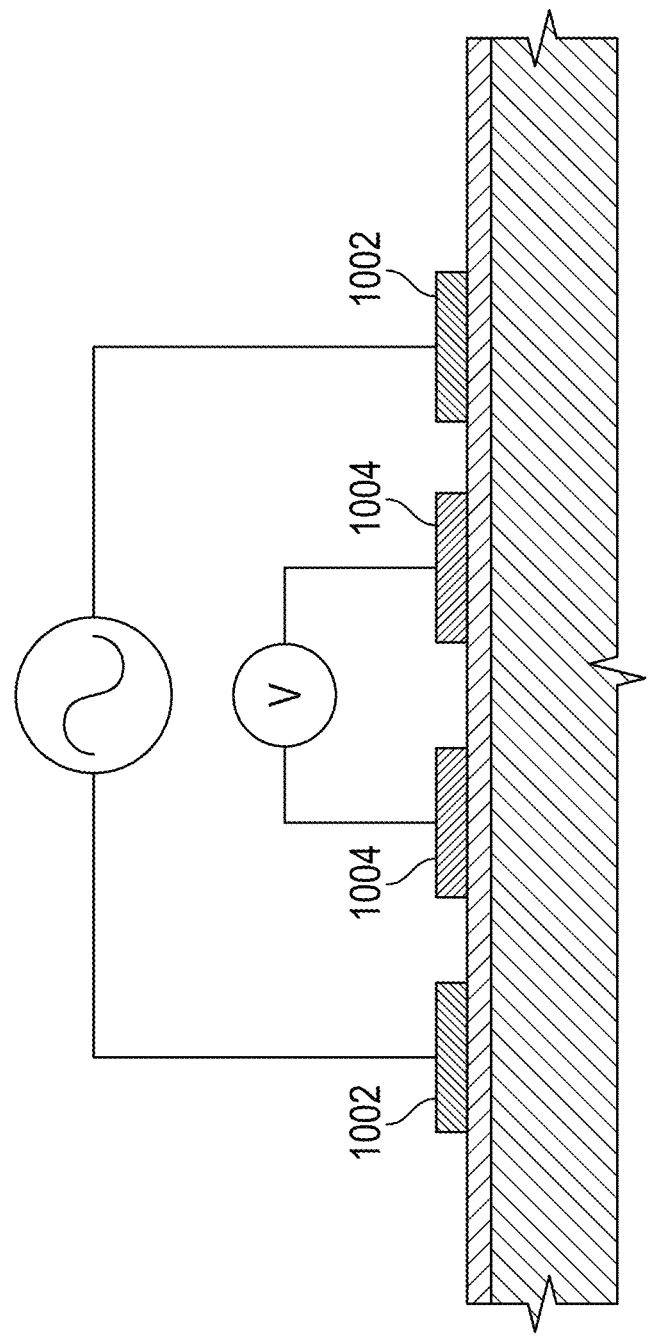
Figure 1E:
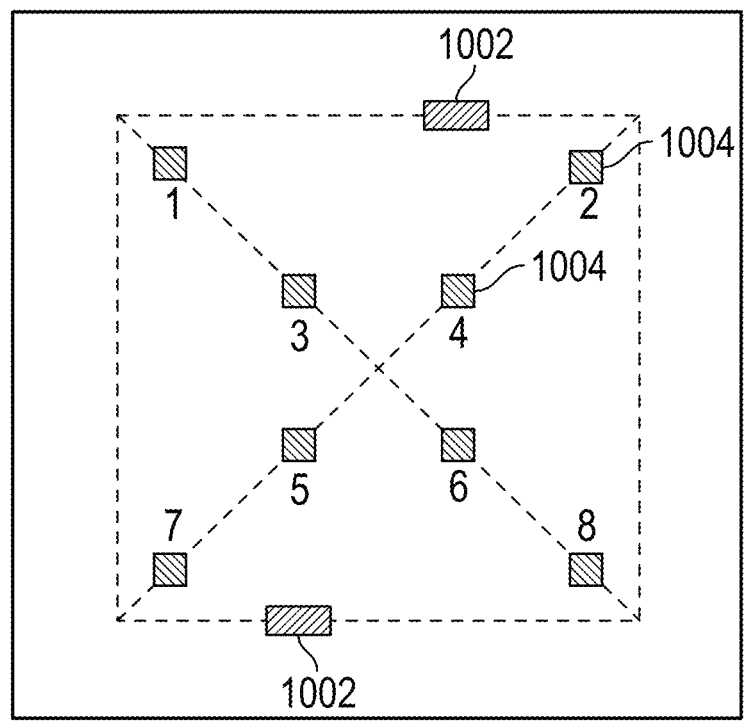

In certain implementations, impedance measurements can be made utilizing a 4-point probe measurement as shown in FIG. 1D. A drive signal, such as AC drive signal, can be generated across drive pads 1002 and the voltage measurement can be made across separate measurement pads 1004. The pads can be positioned as illustrated in FIG. 1E. Eight measurement pads 1004 can be laid out as the corners of two concentric squares. The outer square can have approximately 80 mm side or any other suitable dimension. The inner square can have approximately 30 mm side or any other suitable dimension.

In some implementations, a complex voltage measurement can be taken as follows:

TABLE 1

Impedance measurement Between pads

| | |
|---|---|
| 1 | 2 |
| 1 | 3 |
| 1 | 7 |
| 2 | 4 |
| 2 | 8 |
| 3 | 4 |
| 3 | 5 |
| 3 | 6 |
| 4 | 5 |
| 4 | 6 |
| 5 | 6 |
| 5 | 7 |
| 6 | 8 |
| 7 | 8 |

Complex voltage measurement can identify the maximum and minimum voltages and the phase angle (or time) behind the drive signal. Additional details of impedance measurement are described in one or more of U.S. Provisional Patent Application No. 62/536,774, titled "Skewing Pads for Impedance Measurement," filed on 25 Jul. 2017, or International Patent Application No. PCT/EP2018/069886, titled "Skewing Pads for Impedance Measurement," filed on 23 Jul. 2018, each of which is incorporated by reference in its entirety.

In some embodiments, impedance measurement is based on an AC measurement. An excitation signal can be coupled to the tissue capacitively through a sensor or pad with insulating coating. A second similar electrode can be placed some distance away and connected to ground. By applying an excitation signal, an AC current flows through the tissue between the pads.

Second pair(s) of electrodes can be placed between the excitation electrodes, and can be used to sense voltage. These two electrodes can each be connected to one or more high impedance amplifiers, whose outputs can be fed to a differential amplifier. By measuring this output voltage, and dividing by the excitation current, the impedance between the measurement electrodes can be measured.

Figure 1F:
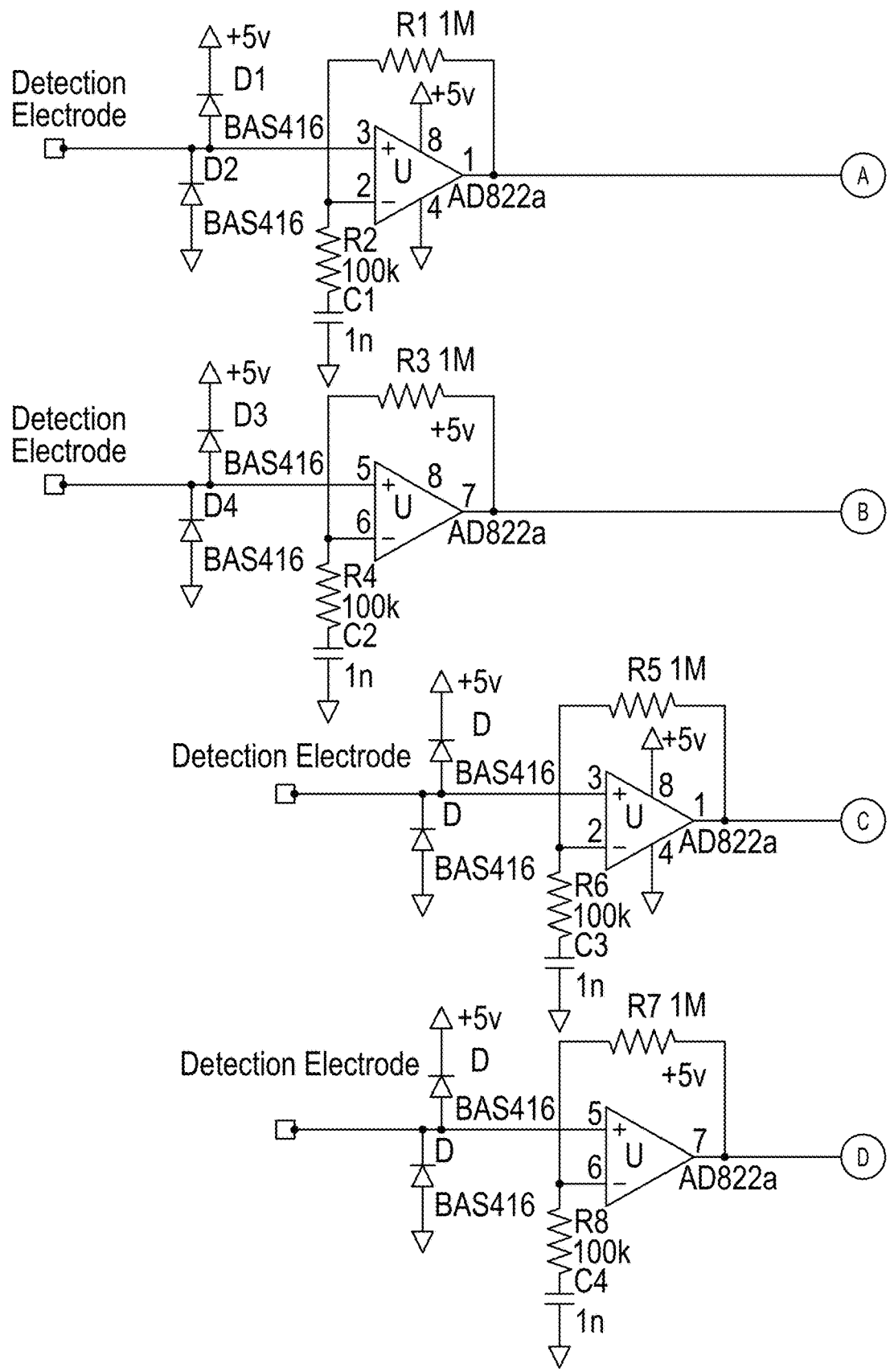
Figure 1F:
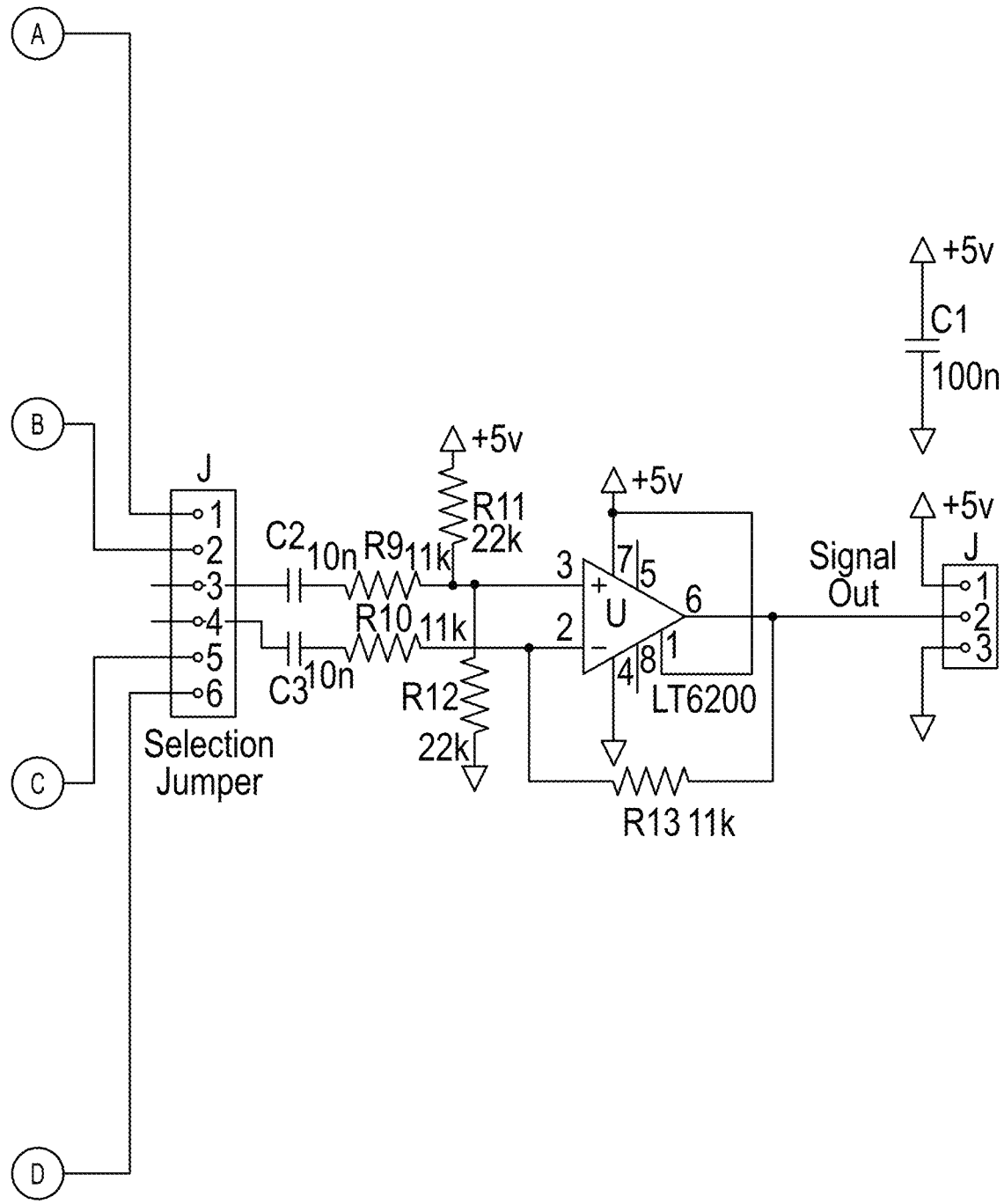

As is illustrated in FIG. 1F, voltage and current can be detected using a pair of lock-in amplifiers. As the measured impedance may be relatively high, particularly at the electrode to tissue junction, it may be advantageous that the measurement electrode amplifiers have high input impedance. First stage amplifiers can be chosen to have high input impedance. These can be configured as non-inverting amplifiers in order to take advantage of this high input impedance. The low-frequency gain can be rolled down using capacitors C1, C2, C3 and C4, as is illustrated in FIG. 1F.

In some cases, for single supply operation, the non-inverting input may need to be biased at mid-rail. The biasing may also need to provide a DC path for the input bias current of the op-amp. While this could be done using a resistive divider at the non-inverting input, it may lead to the following:

1. The bias network lowers the input impedance unless resistors of the order of the op-amp input impedance are used (and resistors of this value are impractically large).

2. Large bias resistors contribute a large thermal noise component which swamps the input noise voltage of the op-amp, reducing the overall signal-to-noise ratio.

In some embodiments, instead of using resistors, the input bias is achieved using a pair of reverse biased diodes D1, D2, D3, and D4 as illustrated in FIG. 1F. The reverse biased diode presents a very high impedance (determined by the reverse leakage), without the high thermal noise contribution. Diode with a very low reverse leakage can be chosen. The reverse leakage also provides the DC path for the op-amp bias current.

Figure 1G:
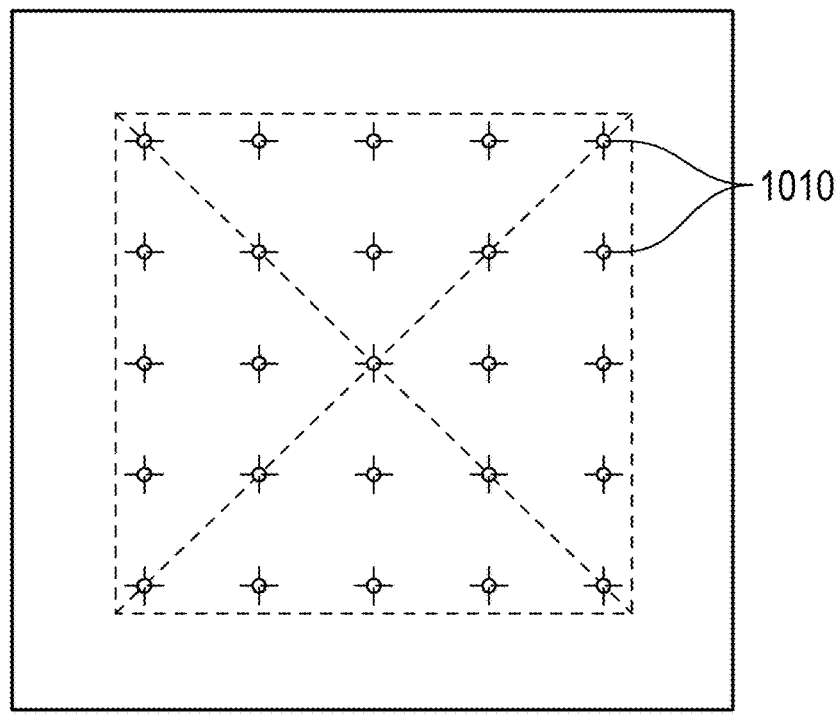

In some embodiments, one or more temperature sensors provide a map of the wound. As is illustrated in FIG. 1G, an array of 25 (or more or less) temperature sensors 1010 in a 5-by-5 grid can be used. The temperature sensors can be positioned equidistant with respect to each other.

Figure 1H:
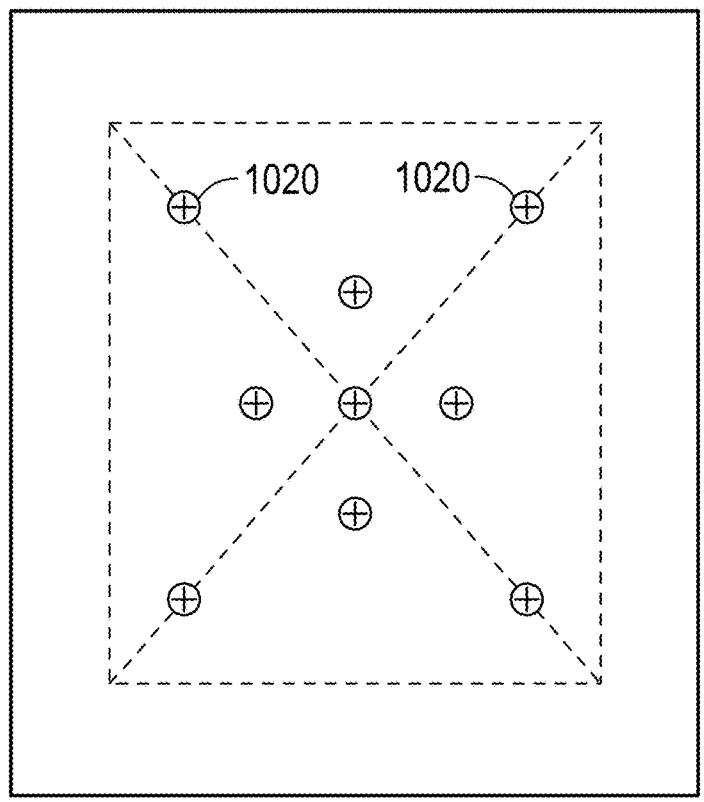

In some embodiments, optical sensors (for example, color sensors, red, green, and blue (RGB) sensors, red, green, blue, and clear (RGBC) sensors, or red, green, blue, and white (RGBW) sensors) can be included in the wound dressing 22 for obtaining one or more optical measurements. Optical sensors can be located in various positions throughout the wound dressing. In some embodiments, RGB sensors can be used for optical measurements. As is illustrated in FIG. 1H, RGB sensors 1020 can incorporate one sensor at the center of the measurement area, four at a mid-distance from the center (such as, approximately 20 mm from the center) and four around the outer edges (such as, approximately 35 mm from the center). Each of the nine RGB sensors can incorporate one sensor one and one white LED.

Any distance, signal value, or the like described in the foregoing is provided for illustrative purposes. In some embodiments, other suitable distances, signal value, or the like can be utilized depending on the size of the measurement area, particular measurements of interest, or the like.

Cybersecurity

A wound monitoring and therapy system 10 may incorporate one or more cybersecurity techniques. For example, the communication device 30 may allow the system 10 to transmit data via a wired or wireless communications network, such as a NFC or cellular network. For instance, NFC can be used for communication with the controller 24 and cellular network can be used for communication with the remote computing device 50. The communications network can provide access to the Internet.

In some embodiments, the system 10 may implement various cybersecurity measures. In certain implementations, when the dressing 22 is connected to the controller 24 (such as, plugged into the controller 24), the controller can initialize. This may include the controller 24 performing one or more of the following:

Powering on. For example, continuous power to the controller 24 and the wound dressing 22 can be established (such as, via a latching circuit).

Generating a device clock. For example, device clock time can start from zero, random number, a unique number, such as a hardware identification number, or the like at initiation and will count up whenever the controller 24 is under power. If power is interrupted, the count may be re-established from the previous clock time before power interruption. In some embodiments, device clock is not a real-time clock, but is an arbitrary value.

Performing a power-on self-test (POST) and other testing. In some implementations, POST can determine whether one or more sensors on the dressing 22 are functioning within proper ranges. For example, functioning of one or more temperature sensors, oxygen sensors, pH sensors, optical sensors, or any additional sensor discussed herein can be tested. Testing may include comparing the results of the sensor test(s) to threshold value(s) or range(s). If it is determined that one or more sensors measurements fall outside threshold value(s) or range(s), indication or alert can be generated. Alert can be visual, audio, tactile, or the like. In some embodiments, the alert may indicate which sensor is experiencing an error state. If the one or more sensors of the dressing 22 passes the POST, one or more of sensor data or device clock time can be recorded. In some instances, one or more components of the system 10 may indicate to the user that sensors are functioning within proper ranges. POST may be performed every time the dressing 22 is connected or re-connected to the controller 24, periodically when the dressing 22 is connected to the controller 24, or the like.

In some embodiments, proper memory capability can be verified as part of initialization. For example, one or more components of the system 10 (such as the computing device 40 or the controller 24) may determine if sufficient memory is remaining upon connection of the dressing 22 to the controller 24 or upon communication of data to the communication device 30. The controller 24 or computing device 40, in some instances, may compare the current remaining memory of the controller 24, communication device 30, or computing device 40 to one or more thresholds. If the current remaining memory of one or more components of the system 10 is below the one or more thresholds, low memory alert can be generated.

In certain implementations, proper capacity of a power source can be verified as part of initialization. This can be performed similarly to the memory testing described herein and a low power alert can be generated. As described herein, a sensor enabled wound dressing 22 connected to a controller 24 may be placed on or in a wound and can collect measurement data from the wound. At least one of the dressing 22 or controller 24 can store the collected measurement data or transmit the measurement data to a computing device 40, via a communication device 30. The dressing 22 or controller 24 may be configured to interact, via a wired or wireless interface, with the communications device 30 to transmit the collected measurement data. The communication device 30 may be connected to a computing device 40 (described herein).

In some embodiments, to facilitate security and patient confidentiality, communication between the controller 24 and the communication device 30 can be one-way communication of data to the communication device 30. As described herein, such communication can be performed wirelessly, such as via NFC when the communication device 30 is placed in communication range of the controller 24.

In some embodiments, communication between the controller 24 and the communication device 30 includes transmission of the device clock time along with data measured by the wound dressing 22 to the communication device 30. For security and patient confidentiality, in certain implementations, device clock time may not reflect real time clock. In addition, information identifying the patient may not be stored on the wound dressing 22, controller 24, or the communication device 30. While the controller 24 may store a unique identification number (such as, hardware identification number), this information alone may not be sufficient to identify the patient as the controller 24 may be used with multiple patients. Without real time clock, measurement data collected by the wound dressing 22 may, at a minimum, remain anonymous and confidential even if the system is hacked.

In some embodiments, real time clock may be known by one or more of the computing device 40 or remote computing device 50. For example, in response to measurement data and device clock time being transmitted from the communication device 30 to the computing device 40, the computing device 40 can correlate device clock time with real time based on the received device clock time and real time clock time. For example, the computing device 40 can, during initialization, receive time of the device clock. During subsequent transmission of measurement data along with device clock time, remote computing device can determine elapsed time relative to the initial transmission based on comparison of the initial time of the device clock and currently received time of the device clock associated with the measurement data. For example, the computing device 40 can subtract the initial time of the device clock from the currently received time of the device clock to determine the elapsed time.

Computing device 40 can be a secure system, such as a medical grade computing device. Computing device 40 can store the data temporarily for transmission to the remote computing device 50, which may correlate the data with patient identification to associate the data to a particular patient. After successfully transmitting the data to the remote computing device 50, computing device 40 can delete the data from storage. As described herein, remote computing device 50 can be a secure system. Remote computing device 50 may store measurement data associated with the particular patient along with real time of when one or more measurements were taken. Patient identification and other related data, such as patient photo(s), patient data, clinician identification, or the like, can be provided to the remote computing device 50 by the mobile device 60. Communication between the mobile device 60 and the remote computing device 50 can be secure, such as encrypted. In some instances, an app or another program is provided on the mobile device 60 for communicating with the remote computing device 50.

In certain cases, the controller 24 can transmit most recently measured data to the computing device 40. The controller 24 can additionally transmit its unique identification number, such as the hardware identification number. Additional data, such as checksum, error correction, or the like can be transmitted.

In some implementations, the controller 24 transmits most recently measured data after initialization. If such initial transmission is successful, the computing device 40 can indicate to the controller 24 that additional measurement data can be collected by the wound dressing 22 as applicable. If the initial transmission is not successful, wound dressing 22 may not be permitted to log additional measurements until communication with the computing device 40 has been successfully established. In some cases, inability to successfully complete the initial transmission may be associated with the system being hacked. If the initial transmission is successful, in some embodiments, all measurement data since previous transmission can be uploaded by the controller 24 to the communication device 30 at a suitable time, such as when the communication device is placed in communication range of the controller 24. Such transmission can be performed after end of treatment.

In some implementations, data transmitted between various components of the system can be encrypted. For example, measurement data stored by the controller 24 can be encrypted.

The dressing 22 or the controller 24 may be disconnected from the communications device 30. One or more components of the system 10, in some embodiments, may alert a user once the dressing 22 or the controller are disconnected. For example, the dressing 22, controller 24, communication device 30, or computing device 40 may provide an alert that one or more components of the system 10 are disconnected. In some instances, the computing device 40 can record a real time clock time when the dressing 22 or controller 24 are disconnected.

As described herein, measurement data recorded from the dressing 22 may be recorded and stored in one or more components of the system 10, such as the controller 24. The data may be stored in accordance with a security protocol, which may safeguard patient privacy and confidentiality. In some embodiments, the recorded measurement data will not include any patient identifying information. The security protocol may include correlating the recorded measurement data with an arbitrary value. In some instances, the arbitrary value may include a device clock time from a non-real time clock indicating the time at which measurement data was obtained. The measurement data may be transferred via the communications device 30 to the computing device 40. In some embodiments, the communication device 30 may only permit one-way communication between the controller 24 and the computing device 40. Alternatively, the communication device 30 may permit the transfer of information to and from the controller 24 and the computing device 40. The measurement data transferred to the computing device 40 may be encrypted, as described herein. In some instances, the recorded measurement data may only be correlated with patient-identifying information once the recorded measurement data is transferred to a secure computing device, such as the remote computing device 50.

In some embodiments, data taken by the perfusion determination device 70 is communicated to the computing device 40 similarly without patient identifying information and real time clock information. Computing device 40 can similarly process the data as described herein.

Measuring Skin Perfusion Pressure

In some embodiments, a perfusion determination device, such as the device 70, includes one or more of the following features. The device can include a sensor module comprising a first sensor in the form of a force sensor for sensing a force transmitted through the sensor module to a measurement or target area, such as the patient's arm or leg and a second sensor in the form of an optical sensor for sensing a parameter which corresponds to the amount of blood perfusion in the skin tissue of the target area underneath the sensor module. In certain implementations, the optical sensor can be a pulse sensor, but other suitable sensors may be used such as a reflective pulse oximeter sensor or the like. The force sensor can be a thin-film micro-force sensor with a diameter of 15 mm and a force range of 45N. The force sensor can also comprise associated read-out electronics. The force sensor can be disposed on an upper portion of the optical sensor, and the optical sensor can be arranged such that it faces away from the force sensor towards the target area. Force and optical sensors can be connected electrically, such as by using one or more wires.

In some implementations, in use, the sensor module can be placed against the target area of a patient so that a lower portion of a housing of the sensor module, which can be open or transparent, is adjacent the target area of skin tissue. The lower portion of the housing may be in contact with the target area. The skin perfusion pressure determination device can then be secured to the measurement area.

Outputs from the force sensor and the optical sensor can be monitored and, if applicable, displayed or otherwise provided to a user.

Figure 6:
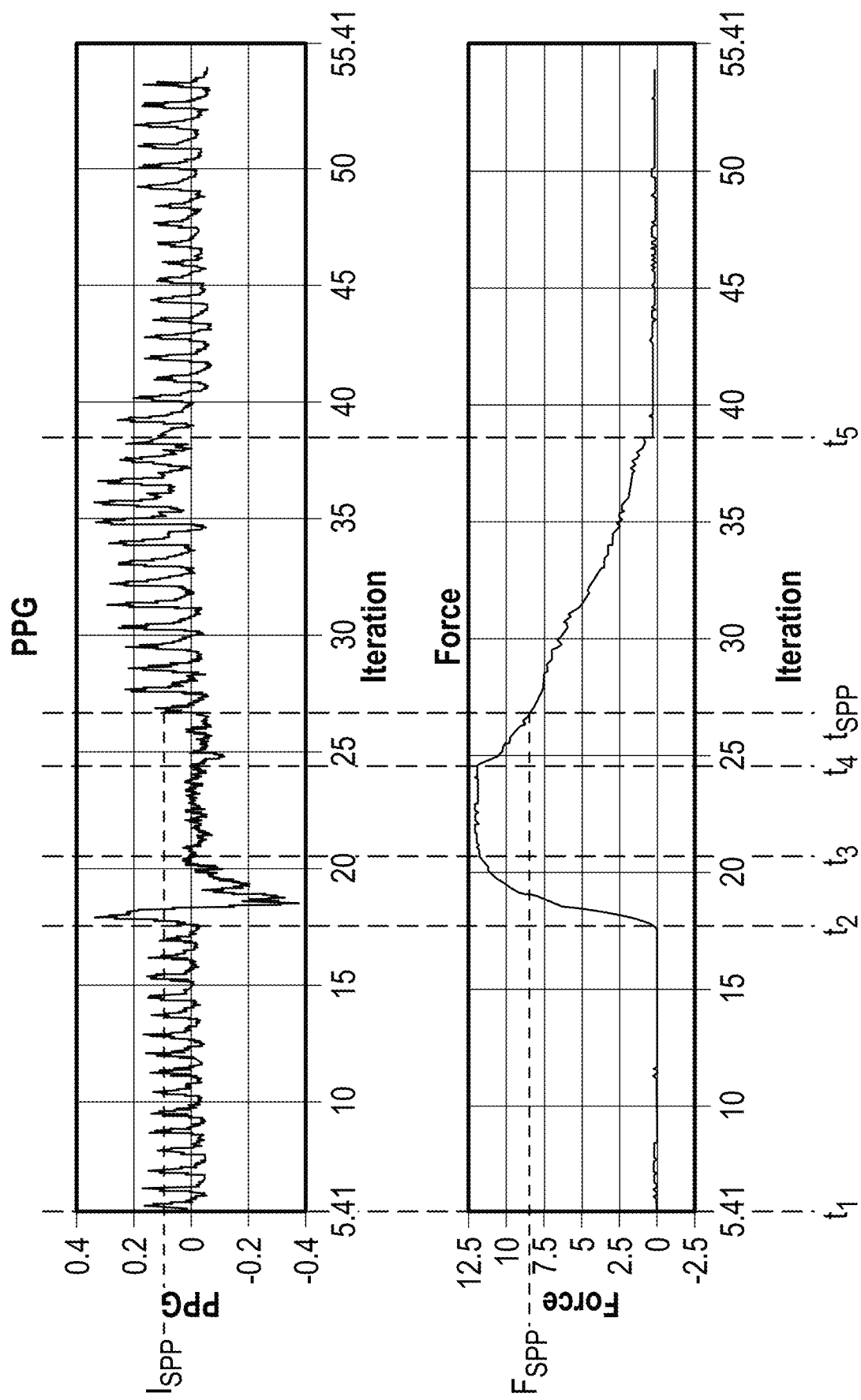
FIG. 6 illustrates skin perfusion pressure determination according to some embodiments.

As is illustrated in FIG. 6, the upper trace is a photoplethysmogram (PPG) which provides an indication of the amount of light emitted by the optical sensor that is absorbed by the skin tissue at the target area (i.e. the trace is inversely proportional to the amount of light reflected by the skin tissue at the target area and received by a photodiode). Therefore, a relatively large amount of blood in the skin tissue, which absorbs a relatively large amount of light emitted by the optical sensor, produces a relatively high output trace value, and vice versa. Of course, the trace could be inverted such that the amount of light reflected by the skin tissue is plotted in which case, a large amount of blood within the skin tissue would produce a relatively low output trace value.

The upper trace will typically have a pulsatile component and a non-pulsatile component. The pulsatile component represents light absorbed by pulsatile arterial blood whereas the non-pulsatile component represents light absorbed by non-pulsatile arterial blood, venous blood and skin tissue. The pulsatile component arises due to the change in blood volume caused by the pressure pulse of the cardiac cycle pushing blood through the blood vessels and capillaries and is therefore associated with blood flow. The pulsatile component can therefore be monitored to obtain an indication of the amount of blood perfusion in the underlying tissue.

The amount of light absorbed by the skin tissue initially once the skin perfusion pressure determination device has been secured to the target area is shown between times $t_1$ and $t_2$ of the upper trace in FIG. 6. Each peak represents a pulse of arterial blood through the skin tissue at the target area.

Time $t_2$ is the time at which a skin perfusion pressure measurement is commenced.

In some embodiments, in use, a user, such as healthcare provider, presses the sensor module against the target area to occlude the blood vessels within the tissue below the target area. The amount of force is increased until the pulsatile component of the trace drops below a predetermined level or ceases to be evident, as shown at time $t_3$. Once the trace drops below the predetermined level, the user continues to hold the sensor module against the target area to ensure that the pulsatile arterial blood flow has ceased in the tissue at the target area, as shown between times $t_3$ and $t_4$. In the example shown, there remains a non-zero noise component of the trace which fluctuates at a level below the predetermined level. At time $t_4$, the user begins to reduce the force applied to the sensor module slowly until time $t_5$ at which time the sensor module has been released completely and pulsatile arterial blood flow in the tissue at the target area is completely restored.

The force exerted by the user on the tissue at the target area via the sensor module is recorded by the lower trace. As can be seen from the lower trace, no force is recorded between times $t_1$ and $t_2$. The force increases relatively rapidly between times $t_2$ and $t_3$ as the user presses the sensor module against the target area of the patient and then plateaus while the user holds the sensor module against the target area between times $t_3$ and $t_4$. As the user begins to slowly release the sensor module at time $t_4$, the applied force reduces steadily back to zero at time $t_5$ and pulsatile arterial blood flow returns to the skin tissue.

Pulsatile arterial blood flow returns when the blood pressure is sufficient to overcome the occlusion pressure on the blood vessels within the tissue which is applied by the user pressing on the sensor module. The return of blood flow is represented by a return of the pulsatile component in the upper trace, as shown at time $t_{SPP}$. Different criteria can be used to determine the return of pulsatile arterial blood flow. For example, return of blood flow could be determined by the return of the value of the upper trace to a predetermined threshold $I_{SPP}$ value such as a value greater than a maximum expected noise value. Alternatively, the threshold value $I_{SPP}$ may be a value that is determined based on the pulse amplitude observed before a force is applied to occlude the blood vessels (i.e. the pulse amplitude between times $t_1$ and $t_2$). In one example, a threshold value $I_{SPP}$ may be used which is a predetermined percentage of the pulse amplitude observed before a force is applied to occlude the blood vessels. Other algorithms may be used to determine return of the pulsatile component of the trace.

The magnitude of the force $F_{SPP}$ of the lower trace at time $t_{SPP}$ is then recorded. The recorded force $F_{SPP}$ can subsequently be used to determine a skin perfusion pressure. This may be done by calculation, look-up tables or based on a pre-calibration of the force sensor. For example, if the contact area of the portion of the sensor module pressed against the skin tissue is known, the pressure applied to the skin tissue can be calculated. In this instance, the target area corresponds to the contact area of the sensor module.

In some embodiments, the contact area of the sensor module can be circular and planar. In some embodiments, the contact area of the sensor module can be circular and convex, and the resulting domed structure can be symmetric or asymmetric. The structure can be of a single side, such as the contact area that would be made onto skin by a dome or it can include of multiple faces, such as a convex polyhedron (which can be similar to the structures seen with geodesic domes, footballs, skeletal formula of buckminsterfullerene). In some embodiments, ridged or scalloped domes and structures can be used. In some embodiments, a mixture of the above may be employed, such as a flat window for optical measurements in the centre of the contact area, which can be surrounded by a convex domed surface. The internal radius of the dome can be designed to allow even loading of force, and thus pressure, across the area of skin that is under assessment. In some embodiments, the contact area of the sensor module is circular and has a diameter of 10 mm and therefore a surface area of approximately 80 mm². The larger the contact area, the greater the force required to stop blood flow. The smaller the contact area, the greater the fluctuations in pressure caused by fluctuations in the force applied so that, for very small contact areas it becomes difficult for a user to release the applied force in a controlled manner in order to determine the force at which blood flow returns. A very small contact area can also make it difficult for an accurate reading to be taken by the blood perfusion sensor. The contact area of the sensor module may therefore be between 1 mm² and 1000 mm², for example between 10 mm² and 400 mm².

A benefit of the arrangement is that contemporaneous measurements of the pressure exerted by the sensor module on the target area and the amount of blood perfusion are made at the target area. The measurements can be taken and recorded simultaneously to produce an accurate and reliable measurement of blood perfusion pressure at a desired location on a patient's body.

Measurement of skin perfusion pressure may be performed as a single measurement or determined from trends evident from repeated measurements over time. Such measurements may be used to aid the prediction of wound healing.

Additional details regarding measurement of skin perfusion pressure are described in International Application No. PCT/EP2018/055940, filed on 9 Mar. 2018, which is incorporated by reference in its entirety.

Negative Pressure Wound Therapy System

Figure 2A:
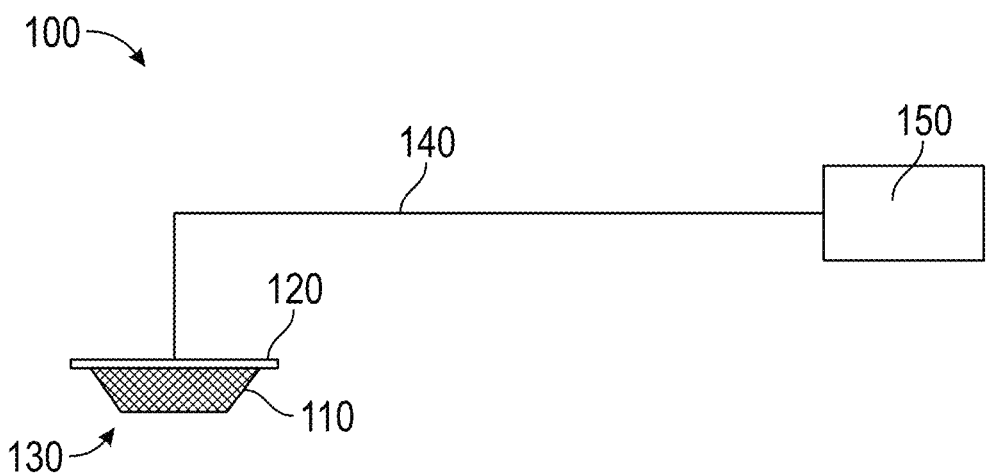
FIG. 2A illustrates a negative pressure wound treatment system according to some embodiments.

FIG. 2A illustrates an embodiment of a negative or reduced pressure wound treatment (or TNP) system 100 comprising a wound filler 130 placed inside a wound cavity 110, the wound cavity sealed by a wound cover 120. The wound filler 130 in combination with the wound cover 120 can be referred to as a wound dressing. The wound dressing may include one or more sensors as described herein. A single or multi lumen tube or conduit 140 is connected the wound cover 120 with a pump assembly 150 configured to supply reduced pressure. The wound cover 120 can be in fluidic communication with the wound cavity 110. In any of the system embodiments disclosed herein, as in the embodiment illustrated in FIG. 2A, the pump assembly can be a canisterless pump assembly (meaning that exudate is collected in the wound dressing or is transferred via tube 140 for collection to another location). However, any of the pump assembly embodiments disclosed herein can be configured to include or support a canister. Additionally, in any of the system embodiments disclosed herein, any of the pump assembly embodiments can be mounted to or supported by the dressing, or adjacent to the dressing.

The wound filler 130 can be any suitable type, such as hydrophilic or hydrophobic foam, gauze, inflatable bag, and so on. The wound filler 130 can be conformable to the wound cavity 110 such that it substantially fills the cavity. The wound cover 120 can provide a substantially fluid impermeable seal over the wound cavity 110. The wound cover 120 can have a top side and a bottom side, and the bottom side adhesively (or in any other suitable manner) seals with wound cavity 110. The conduit 140 or lumen or any other conduit or lumen disclosed herein can be formed from polyurethane, PVC, nylon, polyethylene, silicone, or any other suitable material.

Some embodiments of the wound cover 120 can have a port (not shown) configured to receive an end of the conduit 140. For example, the port can be Renays Soft Port available from Smith & Nephew. In other embodiments, the conduit 140 can otherwise pass through or under the wound cover 120 to supply reduced pressure to the wound cavity 110 so as to maintain a desired level of reduced pressure in the wound cavity. The conduit 140 can be any suitable article configured to provide at least a substantially sealed fluid flow pathway between the pump assembly 150 and the wound cover 120, so as to supply the reduced pressure provided by the pump assembly 150 to wound cavity 110.

The wound cover 120 and the wound filler 130 can be provided as a single article or an integrated single unit. In some embodiments, no wound filler is provided and the wound cover by itself may be considered the wound dressing. The wound dressing may then be connected, via the conduit 140, to a source of negative pressure, such as the pump assembly 150. The pump assembly 150 can be miniaturized and portable, although larger conventional pumps such can also be used.

The wound cover 120 can be located over a wound site to be treated. The wound cover 120 can form a substantially sealed cavity or enclosure over the wound site. In some embodiments, the wound cover 120 can be configured to have a film having a high water vapour permeability to enable the evaporation of surplus fluid, and can have a superabsorbing material contained therein to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. The components of the TNP system described herein can be particularly suited for incisional wounds that exude a small amount of wound exudate.

Some embodiments of the system are designed to operate without the use of an exudate canister. Some embodiments can be configured to support an exudate canister. In some embodiments, configuring the pump assembly 150 and tubing 140 so that the tubing 140 can be quickly and easily removed from the pump assembly 150 can facilitate or improve the process of dressing or pump changes, if necessary. Any of the pump embodiments disclosed herein can be configured to have any suitable connection between the tubing and the pump.

The pump assembly 150 can be configured to deliver negative pressure of approximately −80 mmHg, or between about −20 mmHg and 200 mmHg in some implementations. Note that these pressures are relative to normal ambient atmospheric pressure thus, −200 mmHg would be about 560 mmHg in practical terms. The pressure range can be between about −40 mmHg and −150 mmHg. Alternatively a pressure range of up to −75 mmHg, up to −80 mmHg or over −80 mmHg can be used. Also a pressure range of below −75 mmHg can be used. Alternatively a pressure range of over approximately −100 mmHg, or even 150 mmHg, can be supplied by the pump assembly 150.

In operation, the wound filler 130 is inserted into the wound cavity 110 and wound cover 120 is placed so as to seal the wound cavity 110. The pump assembly 150 provides a source of a negative pressure to the wound cover 120, which is transmitted to the wound cavity 110 via the wound filler 130. Fluid (such as, wound exudate) is drawn through the conduit 140, and can be stored in a canister. In some embodiments, fluid is absorbed by the wound filler 130 or one or more absorbent layers (not shown).

Wound dressings that may be utilized with the pump assembly and other embodiments of the present application include Renasys-F, Renasys-G, Renasys Aft and Pico Dressings available from Smith & Nephew. Further description of such wound dressings and other components of a negative pressure wound therapy system that may be used with the pump assembly and other embodiments of the present application are found in U.S. Patent Publication Nos. 2011/0213287, 2011/0282309, 2012/0116334, 2012/0136325, and 2013/0110058, which are incorporated by reference in their entirety. In other embodiments, other suitable wound dressings can be utilized.

Wound Dressing Overview

Figure 2B:
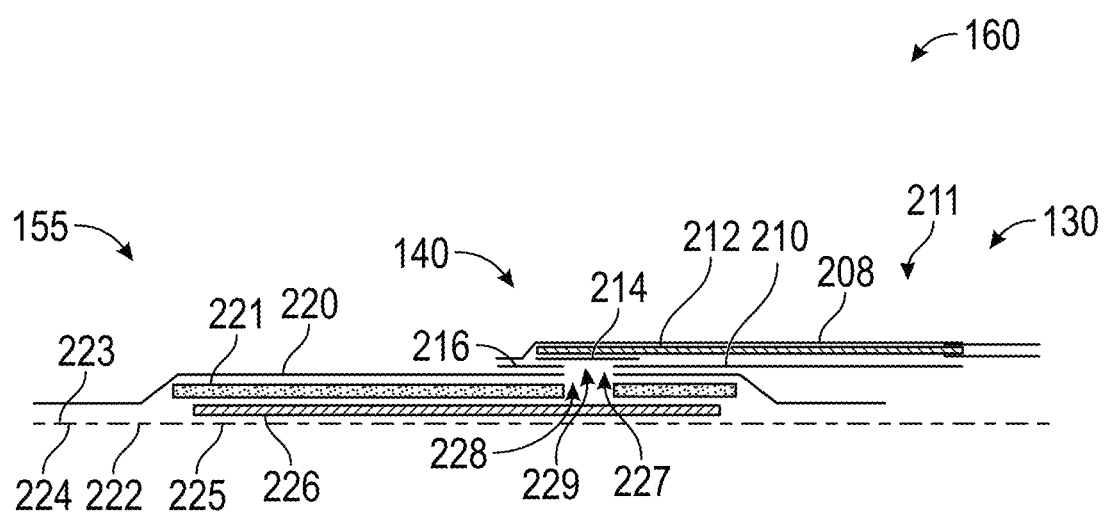
FIG. 2B illustrates a wound dressing according to some embodiments.

FIG. 2B illustrates a cross-section through a wound dressing 155 according to some embodiments. FIG. 2B also illustrates a fluidic connector 160 according to some embodiments. The wound dressing 155 can be similar to the wound dressing described in International Patent Publication WO2013175306 A2, which is incorporated by reference in its entirety. Alternatively, the wound dressing 155 can be any wound dressing embodiment disclosed herein or any combination of features of any number of wound dressing embodiments disclosed herein, can be located over a wound site to be treated. The wound dressing 155 may be placed as to form a sealed cavity over the wound, such as the wound cavity 110. In some embodiments, the wound dressing 155 includes a top or cover layer, or backing layer 220 attached to an optional wound contact layer 222, both of which are described in greater detail below. These two layers 220, 222 can be joined or sealed together so as to define an interior space or chamber. This interior space or chamber may comprise additional structures that may be adapted to distribute or transmit negative pressure, store wound exudate and other fluids removed from the wound, and other functions which will be explained in greater detail below. Examples of such structures, described below, include a transmission layer 226 and an absorbent layer 221.

As used herein the upper layer, top layer, or layer above refers to a layer furthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound.

The wound contact layer 222 can be a polyurethane layer or polyethylene layer or other flexible layer which is perforated, for example via a hot pin process, laser ablation process, ultrasound process or in some other way or otherwise made permeable to liquid and gas. The wound contact layer 222 has a lower surface 224 (for example, facing the wound) and an upper surface 223 (for example, facing away from the wound). The perforations 225 can comprise through holes in the wound contact layer 222 which enable fluid to flow through the layer 222. The wound contact layer 222 helps prevent tissue ingrowth into the other material of the wound dressing. In some embodiments, the perforations are small enough to meet this requirement while still allowing fluid to flow therethrough. For example, perforations formed as slits or holes having a size ranging from 0.025 mm to 1.2 mm are considered small enough to help prevent tissue ingrowth into the wound dressing while allowing wound exudate to flow into the dressing. In some configurations, the wound contact layer 222 may help maintain the integrity of the entire dressing 155 while also creating an air tight seal around the absorbent pad in order to maintain negative pressure at the wound. In some embodiments, the wound contact layer is configured to allow unidirectional or substantially one-way or unidirectional flow of fluid through the wound contact layer when negative pressure is applied to the wound. For example, the wound contact layer can permit fluid to flow away from the wound through the wound contact layer, but not allow fluid to flow back toward the wound. In certain case, the perforations in the wound contact layer are configured to permit such one-way or unidirectional flow of fluid through the wound contact layer.

Some embodiments of the wound contact layer 222 may also act as a carrier for an optional lower and upper adhesive layer (not shown). For example, a lower pressure sensitive adhesive may be provided on the lower surface 224 of the wound dressing 155 whilst an upper pressure sensitive adhesive layer may be provided on the upper surface 223 of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized may be helpful to adhere the wound dressing 155 to the skin around a wound site. In some embodiments, the wound contact layer may comprise perforated polyurethane film. The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers may be perforated together.

A layer 226 of porous material can be located above the wound contact layer 222. This porous layer, or transmission layer, 226 allows transmission of fluid including liquid and gas away from a wound site into upper layers of the wound dressing. In particular, the transmission layer 226 can ensure that an open air channel can be maintained to communicate negative pressure over the wound area even when the absorbent layer has absorbed substantial amounts of exudates. The layer 226 can remain open under the typical pressures that will be applied during negative pressure wound therapy as described above, so that the whole wound site sees an equalized negative pressure. The layer 226 may be formed of a material having a three dimensional structure. For example, a knitted or woven spacer fabric (for example Baltex 7970 weft knitted polyester) or a non-woven fabric could be used.

In some embodiments, the transmission layer 226 comprises a 3D polyester spacer fabric layer including a top layer (that is to say, a layer distal from the wound-bed in use) which is a 84/144 textured polyester, and a bottom layer (that is to say, a layer which lies proximate to the wound bed in use) which is a 10 denier flat polyester and a third layer formed sandwiched between these two layers which is a region defined by a knitted polyester viscose, cellulose or the like monofilament fiber. Other materials and other linear mass densities of fiber could of course be used.

Whilst reference is made throughout this disclosure to a monofilament fiber it will be appreciated that a multistrand alternative could of course be utilized. The top spacer fabric thus has more filaments in a yarn used to form it than the number of filaments making up the yarn used to form the bottom spacer fabric layer.

This differential between filament counts in the spaced apart layers helps control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. In use, this differential tends to draw liquid away from the wound bed and into a central region of the dressing where the absorbent layer 221 helps lock the liquid away or itself wicks the liquid onwards towards the cover layer where it can be transpired.

In some embodiments, to improve the liquid flow across the transmission layer 226 (that is to say perpendicular to the channel region formed between the top and bottom spacer layers, the 3D fabric may be treated with a dry cleaning agent (such as, but not limited to, Perchloro Ethylene) to help remove any manufacturing products such as mineral oils, fats or waxes used previously which might interfere with the hydrophilic capabilities of the transmission layer. An additional manufacturing step can subsequently be carried out in which the 3D spacer fabric is washed in a hydrophilic agent (such as, but not limited to, Feran Ice 30 g/l available from the Rudolph Group). This process step helps ensure that the surface tension on the materials is so low that liquid such as water can enter the fabric as soon as it contacts the 3D knit fabric. This also aids in controlling the flow of the liquid insult component of any exudates.

A layer 221 of absorbent material can be provided above the transmission layer 226. The absorbent material, which comprise a foam or non-woven natural or synthetic material, and which may optionally comprise a super-absorbent material, forms a reservoir for fluid, particularly liquid, removed from the wound site. In some embodiments, the layer 221 may also aid in drawing fluids towards the backing layer 220.

The material of the absorbent layer 221 may also prevent liquid collected in the wound dressing 155 from flowing freely within the dressing, and can act so as to contain any liquid collected within the dressing. The absorbent layer 221 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 221 may typically be manufactured from ALLEVYN™ foam, Freudenberg 114-224-4 or Chem-Posite™ 11C-450. In some embodiments, the absorbent layer 221 may comprise a composite comprising superabsorbent powder, fibrous material such as cellulose, and bonding fibers. In a some embodiments, the composite is an airlaid, thermally-bonded composite.

In some embodiments, the absorbent layer 221 is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. The wicking action also assists in bringing liquid into contact with the upper cover layer to aid increase transpiration rates of the dressing.

An aperture, hole, or orifice 227 can be provided in the backing layer 220 to allow a negative pressure to be applied to the dressing 155. In some embodiments, the fluidic connector 160 is attached or sealed to the top of the backing layer 220 over the orifice 227 made into the dressing 155, and communicates negative pressure through the orifice 227. A length of tubing may be coupled at a first end to the fluidic connector 160 and at a second end to a pump unit (not shown) to allow fluids to be pumped out of the dressing. Where the fluidic connector is adhered to the top layer of the wound dressing, a length of tubing may be coupled at a first end of the fluidic connector such that the tubing, or conduit, extends away from the fluidic connector parallel or substantially to the top surface of the dressing. The fluidic connector 160 may be adhered and sealed to the backing layer 220 using an adhesive such as an acrylic, cyanoacrylate, epoxy, UV curable or hot melt adhesive. The fluidic connector 160 may be formed from a soft polymer, for example a polyethylene, a polyvinyl chloride, a silicone or polyurethane having a hardness of 30 to 90 on the Shore A scale. In some embodiments, the fluidic connector 160 may be made from a soft or conformable material.

In some embodiments, the absorbent layer 221 includes at least one through hole 228 located so as to underlie the fluidic connector 160. The through hole 228 may in some embodiments be the same size as the opening 227 in the backing layer, or may be bigger or smaller. As illustrated in FIG. 2B a single through hole can be used to produce an opening underlying the fluidic connector 160. It will be appreciated that multiple openings could alternatively be utilized. Additionally should more than one port be utilized according to certain embodiments of the present disclosure one or multiple openings may be made in the absorbent layer and the obscuring layer in registration with each respective fluidic connector. Although not essential to certain embodiments of the present disclosure the use of through holes in the super-absorbent layer may provide a fluid flow pathway which remains unblocked in particular when the absorbent layer is near saturation.

The aperture or through-hole 228 can be provided in the absorbent layer 221 beneath the orifice 227 such that the orifice is connected directly to the transmission layer 226 as illustrated in FIG. 2B. This allows the negative pressure applied to the fluidic connector 160 to be communicated to the transmission layer 226 without passing through the absorbent layer 221. This ensures that the negative pressure applied to the wound site is not inhibited by the absorbent layer as it absorbs wound exudates. In other embodiments, no aperture may be provided in the absorbent layer 221, or alternatively a plurality of apertures underlying the orifice 227 may be provided. In further alternative embodiments, additional layers such as another transmission layer or an obscuring layer such as described in International Patent Publication WO2014020440, the entirety of which is hereby incorporated by reference, may be provided over the absorbent layer 221 and beneath the backing layer 220.

The backing layer 220 is can be gas impermeable, but moisture vapor permeable, and can extend across the width of the wound dressing 155. The backing layer 220, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the backing layer 220 and a wound site where a negative pressure can be established. The backing layer 220 can be sealed to the wound contact layer 222 in a border region around the circumference of the dressing, ensuring that no air is drawn in through the border area, for example via adhesive or welding techniques. The backing layer 220 protects the wound from external bacterial contamination (bacterial barrier) and allows liquid from wound exudates to be transferred through the layer and evaporated from the film outer surface. The backing layer 220 can include two layers; a polyurethane film and an adhesive pattern spread onto the film. The polyurethane film can be moisture vapor permeable and may be manufactured from a material that has an increased water transmission rate when wet. In some embodiments the moisture vapor permeability of the backing layer increases when the backing layer becomes wet. The moisture vapor permeability of the wet backing layer may be up to about ten times more than the moisture vapor permeability of the dry backing layer.

The absorbent layer 221 may be of a greater area than the transmission layer 226, such that the absorbent layer overlaps the edges of the transmission layer 226, thereby ensuring that the transmission layer does not contact the backing layer 220. This provides an outer channel of the absorbent layer 221 that is in direct contact with the wound contact layer 222, which aids more rapid absorption of exudates to the absorbent layer. Furthermore, this outer channel ensures that no liquid is able to pool around the circumference of the wound cavity, which may otherwise seep through the seal around the perimeter of the dressing leading to the formation of leaks. As illustrated in FIG. 2B, the absorbent layer 221 may define a smaller perimeter than that of the backing layer 220, such that a boundary or border region is defined between the edge of the absorbent layer 221 and the edge of the backing layer 220.

As shown in FIG. 2B, one embodiment of the wound dressing 155 comprises an aperture 228 in the absorbent layer 221 situated underneath the fluidic connector 160. In use, for example when negative pressure is applied to the dressing 155, a wound facing portion of the fluidic connector may thus come into contact with the transmission layer 226, which can thus aid in transmitting negative pressure to the wound site even when the absorbent layer 221 is filled with wound fluids. Some embodiments may have the backing layer 220 be at least partly adhered to the transmission layer 226. In some embodiments, the aperture 228 is at least 1-2 mm larger than the diameter of the wound facing portion of the fluidic connector 11, or the orifice 227.

For example, in embodiments with a single fluidic connector 160 and through hole, it may be preferable for the fluidic connector 160 and through hole to be located in an off-center position. Such a location may permit the dressing 155 to be positioned onto a patient such that the fluidic connector 160 is raised in relation to the remainder of the dressing 155. So positioned, the fluidic connector 160 and the filter 214 may be less likely to come into contact with wound fluids that could prematurely occlude the filter 214 so as to impair the transmission of negative pressure to the wound site.

Turning now to the fluidic connector 160, some embodiments include a sealing surface 216, a bridge 211 with a proximal end (closer to the negative pressure source) and a distal end 140, and a filter 214. The sealing surface 216 can form the applicator that is sealed to the top surface of the wound dressing. In some embodiments a bottom layer of the fluidic connector 160 may comprise the sealing surface 216. The fluidic connector 160 may further comprise an upper surface vertically spaced from the sealing surface 216, which in some embodiments is defined by a separate upper layer of the fluidic connector. In other embodiments the upper surface and the lower surface may be formed from the same piece of material. In some embodiments the sealing surface 216 may comprise at least one aperture 229 therein to communicate with the wound dressing. In some embodiments the filter 214 may be positioned across the opening 229 in the sealing surface, and may span the entire opening 229. The sealing surface 216 may be configured for sealing the fluidic connector to the cover layer of the wound dressing, and may comprise an adhesive or weld. In some embodiments, the sealing surface 216 may be placed over an orifice in the cover layer with optional spacer elements 215 configured to create a gap between the filter 214 and the transmission layer 226. In other embodiments, the sealing surface 216 may be positioned over an orifice in the cover layer and an aperture in the absorbent layer 220, permitting the fluidic connector 160 to provide air flow through the transmission layer 226. In some embodiments, the bridge 211 may comprise a first fluid passage 212 in communication with a source of negative pressure, the first fluid passage 212 comprising a porous material, such as a 3D knitted material, which may be the same or different than the porous layer 226 described previously. The bridge 211 can be encapsulated by at least one flexible film layer 208, 210 having a proximal and distal end and configured to surround the first fluid passage 212, the distal end of the flexible film being connected the sealing surface 216. The filter 214 is configured to substantially prevent wound exudate from entering the bridge, and spacer elements 215 are configured to prevent the fluidic connector from contacting the transmission layer 226. These elements will be described in greater detail below.

Some embodiments may further comprise an optional second fluid passage positioned above the first fluid passage 212. For example, some embodiments may provide for an air leak may be disposed at the proximal end of the top layer that is configured to provide an air path into the first fluid passage 212 and dressing 155 similar to the suction adapter as described in U.S. Pat. No. 8,801,685, which is incorporated by reference herein in its entirety.

In some embodiment, the fluid passage 212 is constructed from a compliant material that is flexible and that also permits fluid to pass through it if the spacer is kinked or folded over. Suitable materials for the fluid passage 212 include without limitation foams, including open-cell foams such as polyethylene or polyurethane foam, meshes, 3D knitted fabrics, non-woven materials, and fluid channels. In some embodiments, the fluid passage 212 may be constructed from materials similar to those described above in relation to the transmission layer 226. Advantageously, such materials used in the fluid passage 212 not only permit greater patient comfort, but may also provide greater kink resistance, such that the fluid passage 212 is still able to transfer fluid from the wound toward the source of negative pressure while being kinked or bent.

In some embodiments, the fluid passage 212 may be comprised of a wicking fabric, for example a knitted or woven spacer fabric (such as a knitted polyester 3D fabric, Baltex 7970®, or Gehring 879®) or a nonwoven fabric. These materials selected can be suited to channeling wound exudate away from the wound and for transmitting negative pressure or vented air to the wound site, and may also confer a degree of kinking or occlusion resistance to the fluid passage 212. In some embodiments, the wicking fabric may have a three-dimensional structure, which in some cases may aid in wicking fluid or transmitting negative pressure. In certain embodiments, including wicking fabrics, these materials remain open and capable of communicating negative pressure to a wound area under the typical pressures used in negative pressure therapy, for example between −40 to −150 mmHg. In some embodiments, the wicking fabric may comprise several layers of material stacked or layered over each other, which may in some cases be useful in preventing the fluid passage 212 from collapsing under the application of negative pressure. In other embodiments, the wicking fabric used in the fluid passage 212 may be between 1.5 mm and 6 mm; more preferably, the wicking fabric may be between 3 mm and 6 mm thick, and may be comprised of either one or several individual layers of wicking fabric. In other embodiments, the fluid passage 212 may be between 1.2-3 mm thick, and preferably thicker than 1.5 mm. Some embodiments, for example a suction adapter used with a dressing which retains liquid such as wound exudate, may employ hydrophobic layers in the fluid passage 212, and only gases may travel through the fluid passage 212. Additionally, and as described previously, the materials used in the system can be conformable and soft, which may help to avoid pressure ulcers and other complications which may result from a wound treatment system being pressed against the skin of a patient.

In some embodiments, the filter element 214 is impermeable to liquids, but permeable to gases, and is provided to act as a liquid barrier and to ensure that no liquids are able to escape from the wound dressing 155. The filter element 214 may also function as a bacterial barrier. Typically the pore size is 0.2 µm. Suitable materials for the filter material of the filter element 214 include 0.2 micron Gore™ expanded PTFE from the MMT range, PALL Versapore™ 200R, and Donaldson™ TX6628. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. The filter element can be attached or sealed to the port or the cover film over the orifice. For example, the filter element 214 may be molded into the fluidic connector 160, or may be adhered to one or both of the top of the cover layer and bottom of the suction adapter 160 using an adhesive such as, but not limited to, a UV cured adhesive.

It will be understood that other types of material could be used for the filter element 214. More generally a microporous membrane can be used which is a thin, flat sheet of polymeric material, this contains billions of microscopic pores. Depending upon the membrane chosen these pores can range in size from 0.01 to more than 10 micrometers. Microporous membranes are available in both hydrophilic (water filtering) and hydrophobic (water repellent) forms. In some embodiments, filter element 214 comprises a support layer and an acrylic co-polymer membrane formed on the support layer. In some embodiments, the wound dressing 155 according to certain embodiments uses microporous hydrophobic membranes (MHMs). Numerous polymers may be employed to form MHMs. For example, the MHMs may be formed from one or more of PTFE, polypropylene, PVDF and acrylic copolymer. All of these optional polymers can be treated in order to obtain specific surface characteristics that can be both hydrophobic and oleophobic. As such these will repel liquids with low surface tensions such as multi-vitamin infusions, lipids, surfactants, oils and organic solvents.

MHMs block liquids whilst allowing air to flow through the membranes. They are also highly efficient air filters eliminating potentially infectious aerosols and particles. A single piece of MHM is well known as an option to replace mechanical valves or vents. Incorporation of MHMs can thus reduce product assembly costs improving profits and costs/benefit ratio to a patient.

The filter element 214 may also include an odor absorbent material, for example activated charcoal, carbon fiber cloth or Vitec Carbotec-RT Q2003073 foam, or the like. For example, an odor absorbent material may form a layer of the filter element 214 or may be sandwiched between microporous hydrophobic membranes within the filter element. The filter element 214 thus enables gas to be exhausted through the orifice. Liquid, particulates and pathogens however are contained in the dressing.

The wound dressing 155 may comprise spacer elements 215 in conjunction with the fluidic connector 160 and the filter 214. With the addition of such spacer elements 215 the fluidic connector 160 and filter 214 may be supported out of direct contact with the absorbent layer 220 or the transmission layer 226. The absorbent layer 220 may also act as an additional spacer element to keep the filter 214 from contacting the transmission layer 226. Accordingly, with such a configuration contact of the filter 214 with the transmission layer 226 and wound fluids during use may thus be minimized.

Similar to the embodiments of wound dressings described herein, some wound dressings comprise a perforated wound contact layer, which can include silicone adhesive on the wound- or skin-contact face and/or acrylic adhesive on the reverse. The wound contact layer can be perforated to match any pattern suitable of a particular wound. Above this bordered layer sits a transmission layer or a 3D spacer fabric pad. Above the transmission layer, sits an absorbent layer. The absorbent layer can include a superabsorbent non-woven (NW) pad. The absorbent layer can over-border the transmission layer by approximately 5 mm at the perimeter. The absorbent layer can have an aperture or through-hole toward one end. The aperture can be about 10 mm in diameter. Over the transmission layer and absorbent layer lies a backing layer. The backing layer can be a high moisture vapor transmission rate (MVTR) film, pattern coated with acrylic adhesive. The high MVTR film and wound contact layer encapsulate the transmission layer and absorbent layer, creating a perimeter border of approximately 20 mm. The backing layer can have a 10 mm aperture that overlies the aperture in the absorbent layer. Above the hole can be bonded a fluidic connector that comprises a liquid-impermeable, gas-permeable semi-permeable membrane (SPM) or filter that overlies the aforementioned apertures.

Wound Dressing with Sensors

As described herein, a wound dressing that incorporates a number of sensors can be utilized in order to monitor characteristics of a wound as it heals. Collecting data from the wounds that heal well, and from those that do not, can provide useful insights towards identifying measurands to indicate one or more of whether a wound is on a healing or non-healing trajectory, provide wound status, clinical feedback, or the like. Any of the disclosed wound dressings, such as wound dressing 22 can include one or more of the following features or any other features disclosed herein.

Figure 3:
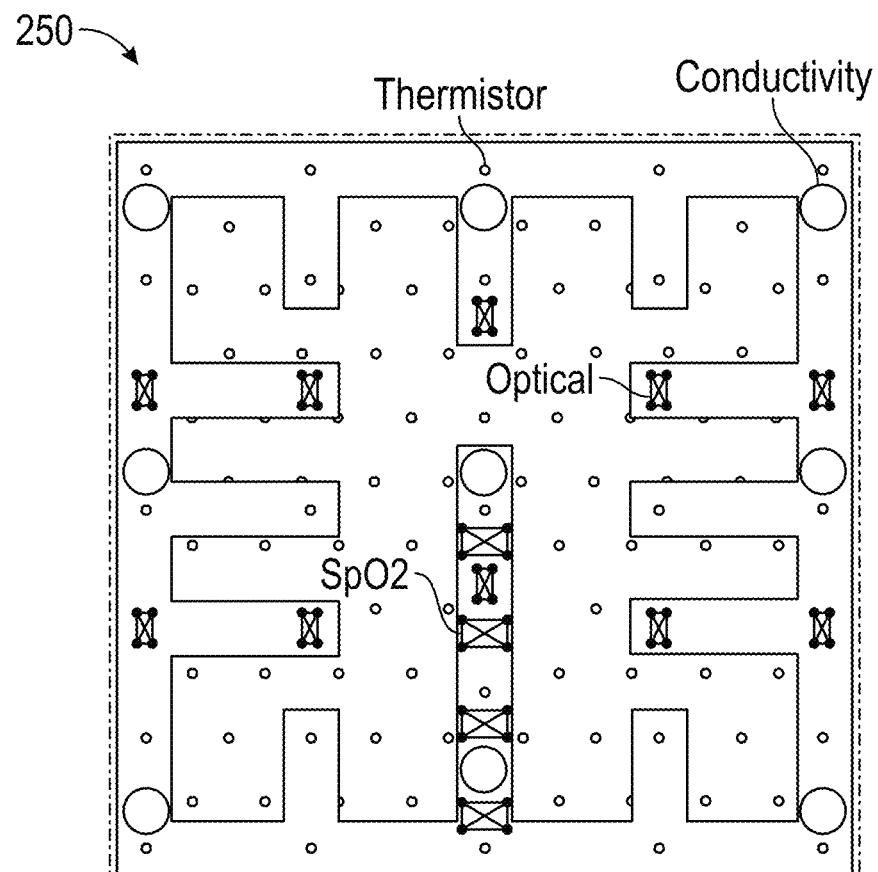
FIG. 3 illustrates a sensor array illustrating the sensor placement incorporated into a wound dressing according to some embodiments.
Figure 4A:
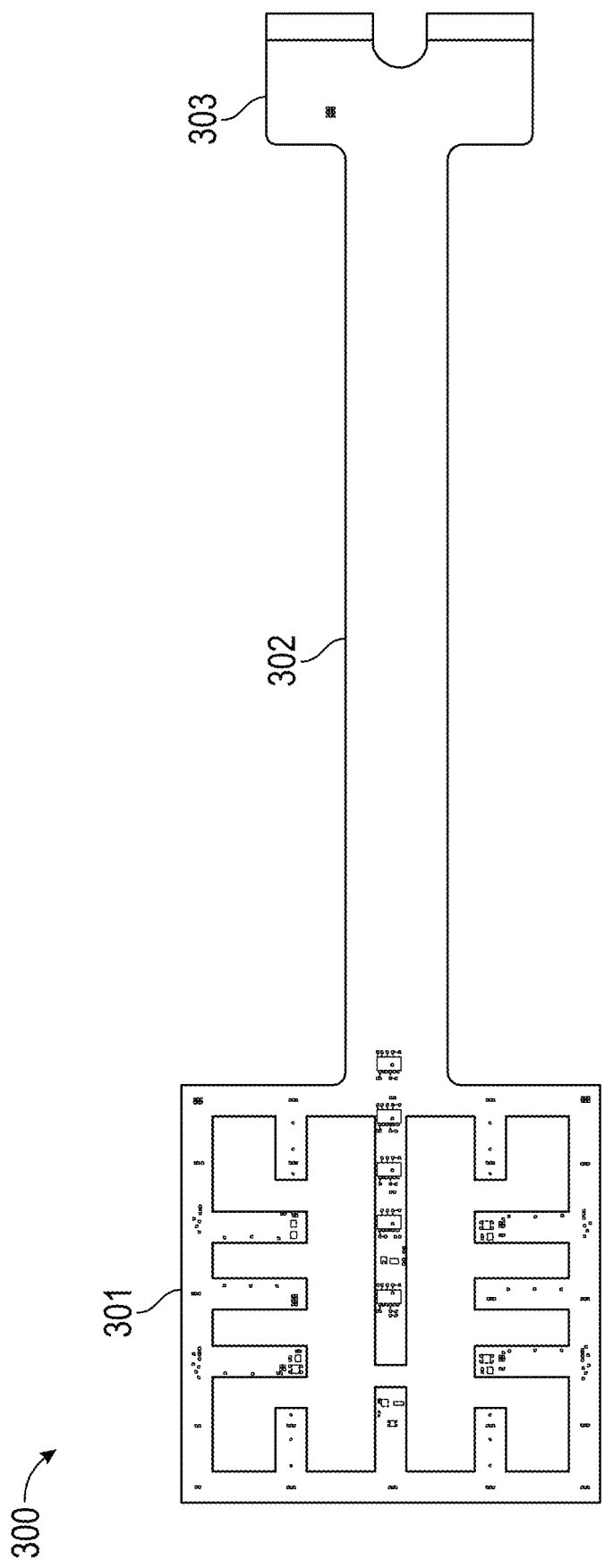
FIG. 4A illustrates a flexible sensor array including a sensor array portion, a tail portion and a connector pad end portion according to some embodiments.

In some implementations, a number of sensor technologies can be used in wound dressings or one or more components forming part of an overall wound dressing apparatus. For example, as illustrated in FIGS. 3 and 4D, which depict wound dressings 250 and 320 with sensor arrays according to some embodiments, one or more sensors can be incorporated onto or into a wound contact layer, which may be a perforated wound contact layer as shown in FIG. 4D. The wound contact layer in FIGS. 3 and 4D is illustrated as having a square shape, but it will be appreciated that the wound contact layer may have other shapes such as rectangular, circular, oval, etc. In some embodiments, the sensor integrated wound contact layer can be provided as an individual material layer that is placed over the wound area and then covered by a wound dressing apparatus or components of a wound dressing apparatus, such as gauze, foam or other wound packing material, a superabsorbent layer, a drape, a fully integrated dressing like the Pico or Allevyn Life dressing, etc. In other embodiments, the sensor integrated wound contact layer may be part of a single unit dressing such as described herein.

The sensor-integrated wound contact layer can be placed in contact with the wound and will allow fluid to pass through the contact layer while causing little to no damage to the tissue in the wound. The sensor-integrated wound contact layer can be made of a flexible material such as silicone and can incorporate antimicrobials or other therapeutic agents known in the art. In some embodiments, the sensor-integrated wound contact layer can incorporate adhesives that adhere to wet or dry tissue. In some embodiments, the sensors or sensor array can be incorporated into or encapsulated within other components of the wound dressing such as the absorbent layer or spacer layer described above.

As shown in FIGS. 3 and 4D, five sensors can be used, including, for instance, sensors for temperature (such as, 25 thermistor sensors, in a 5×5 array, ~20 mm pitch), oxygen saturation or SpO2 (such as, 4 or 5 SpO2 sensors, in a single line from the center of the wound contact layer to the edge thereof, 10 mm pitch), tissue color (such as, 10 optical sensors, in 2×5 array, ~20 mm pitch; not all 5 sensors in each row of the array need be aligned), pH (such as, by measuring colour of a pH sensitive pad, optionally using the same optical sensors as for tissue colour), and conductivity (such as, 9 conductivity contacts, in a 3×3 array, ~40 mm pitch). As shown in FIG. 4A, the SpO2 sensors can be arranged in a single line from the center of or near the center of the wound contact layer to the edge of the wound contact layer. The line of SpO2 sensors can allow the sensor to take measurements in the middle of the wound, at the edge or the wound, or on intact skin to measure changes between the various regions. In some embodiments, the wound contact layer or sensor array can be larger than the size of the wound to cover the entire surface area of the wound as well as the surrounding intact skin. The larger size of the wound contact layer and/or sensor array and the multiple sensors can provide more information about the wound area than if the sensor was only placed in the center of the wound or in only one area at a time.

The sensors can be incorporated onto flexible circuit boards formed of flexible polymers including polyamide, polyimide (PI), polyester, polyethylene naphthalate (PEN), polyetherimide (PEI), along with various fluropolymers (FEP) and copolymers, or any material known in the art. The sensor array can be incorporated into a two-layer flexible circuit. In some embodiments, the circuit board can be a multi-layer flexible circuit board. In some embodiments, these flexible circuits can be incorporated into any layer of the wound dressing. In some embodiments, a flexible circuit can be incorporated into a wound contact layer. For example, the flexible circuit can be incorporated into a wound contact layer similar to the wound contact layer described with reference to FIG. 2B. The wound contact layer can have cutouts or slits that allow for one or more sensors to protrude out of the lower surface of the wound contact layer and contact the wound area directly.

In some embodiments, the sensor-integrated wound contact layer can include a first and second wound contact layer with the flexible circuit board sandwiched between the two layers of wound contact layer material. The first wound contact layer has a lower surface intended to be in contact with the wound and an upper surface intended to be in contact with flexible circuit board. The second wound contact layer has a lower surface intended to be in contact with the flexible circuit board and an upper surface intended to be in contact with a wound dressings or one or more components forming part of an overall wound dressing apparatus. The upper surface of the first wound contact layer and the lower surface of the second wound contact layer can be adhered together with the flexible circuit board sandwiched between the two layers.

In some embodiments, the one or more sensors of the flexible circuit board can be fully encapsulated or covered by the wound contact layers to prevent contact with moisture or fluid in the wound. In some embodiments, the first wound contact layer can have cutouts or slits that allow for one or more sensors to protrude out of the lower surface and contact the wound area directly. For example, the one or more SpO2 sensors as shown in FIG. 4D are shown protruding out the bottom surface of the wound contact layer. In some embodiments, the SpO2 sensors can be mounted directly on a lower surface of the first wound contact layer. Some or all of the sensors and electrical or electronic components may be potted or encapsulated (for example, rendered waterproof or liquid-proof) with a polymer, for example, silicone or epoxy based polymers. The encapsulation with a polymer can prevent ingress of fluid and leaching of chemicals from the components. In some embodiments, the wound contact layer material can seal the components from water ingress and leaching of chemicals.

In some embodiments, gathering and processing information related to the wound can utilize three components, including a sensor array, a control or processing module, and software. These components are described in more detail herein.

FIG. 4A illustrates a flexible sensor array circuit board 300 that includes a sensor array portion 301, a tail portion 302, and a connector pad end portion 303 according to some embodiments. The sensor array portion 301 can include the sensors and associated circuitry. The sensor array circuit board 300 can include a long tail portion 302 extending from the sensor array portion 301. The connector pad end portion 303 can be enabled to connect to a control module or other processing unit to receive the data from the sensor array circuit. The long tail portion 302 can allow the control module to be placed distant from the wound, such as for example in a more convenient location away from the wound.

Figure 4B:
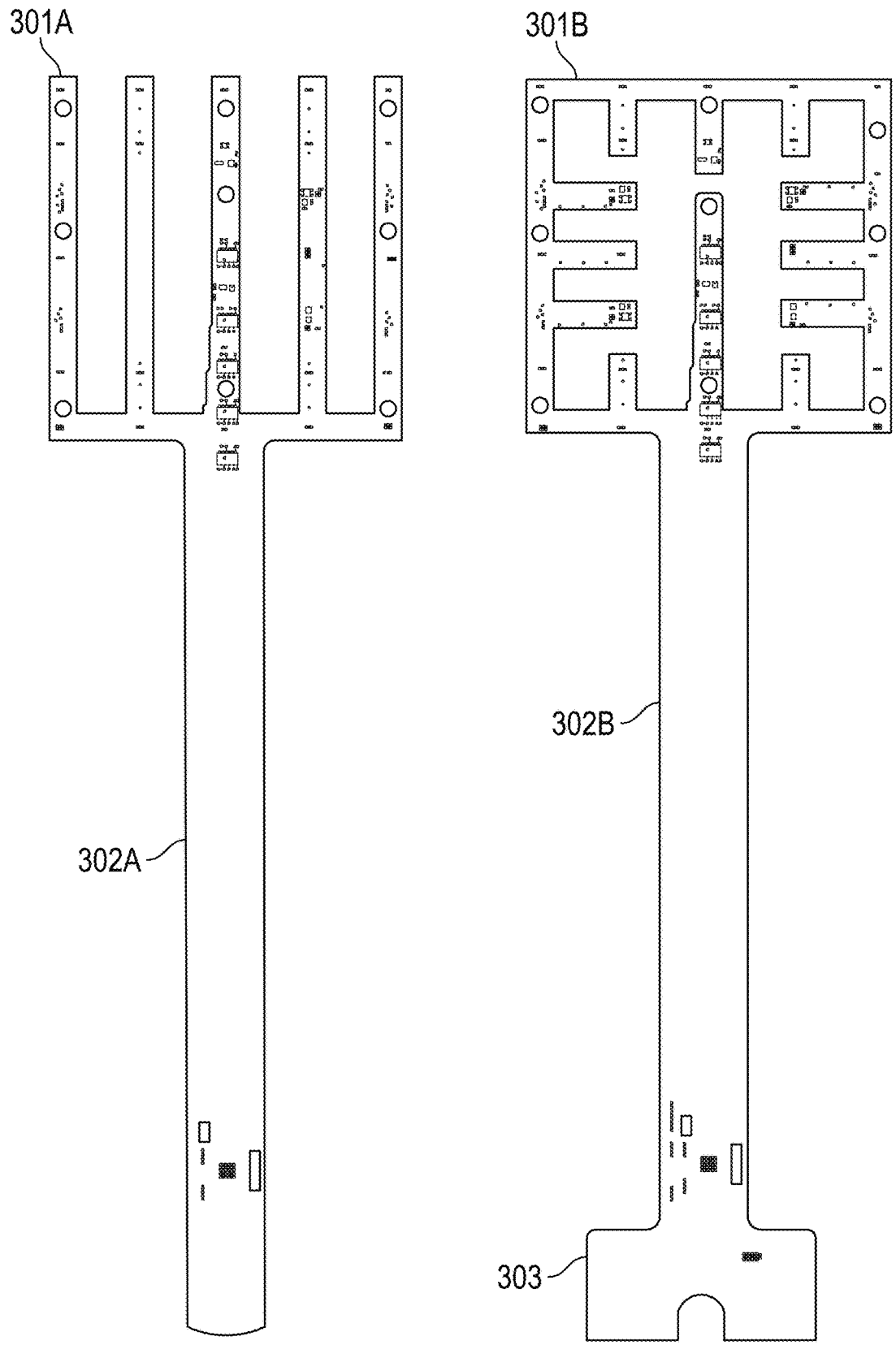
FIG. 4B illustrates flexible circuit boards with different sensor array geometries according to some embodiments.
Figure 4B:
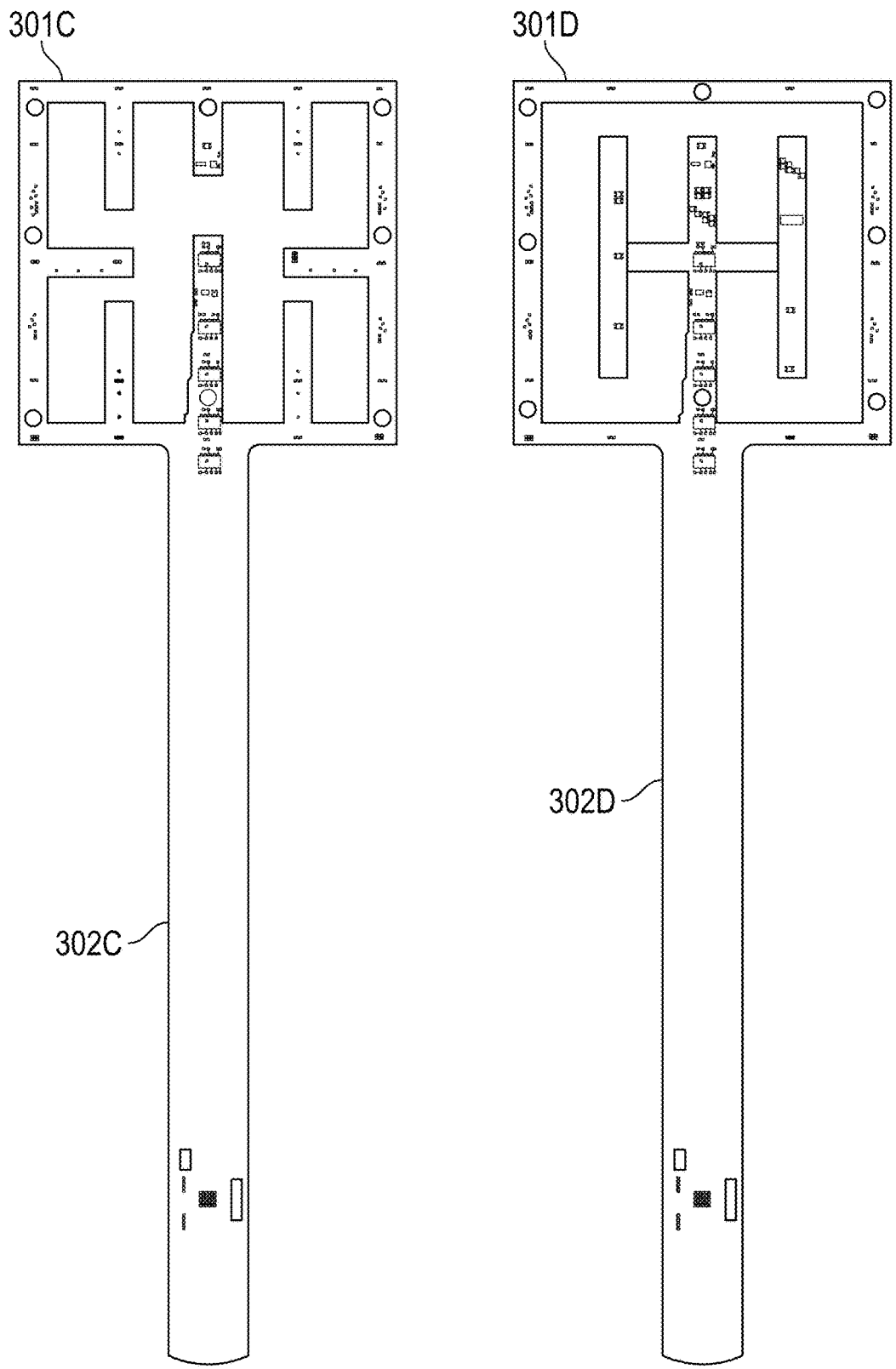

FIG. 4B illustrates embodiments of the flexible circuit boards with four different sensor array geometries 301A, 301B, 301C, and 301D according to some embodiments. The illustrated embodiments include tail portions 302A, 302B. 302C, and 302D. In some embodiments, flexible circuit boards include a short portion or no tail portion. In some embodiments, four different sensor array geometries shown can be implemented in flexible circuits. While FIG. 4B show four different sensor array formats and configurations, the design 301B and 302B also includes the connector pads end portion 303 configured to provide electrical or electronic connection between the sponsor array 301B and a control module. One or more of the designs in 301A, 301C, or 301D can also include a connector pads end portion, such as the portion 303, to allow flexible circuit boards 301A, 301C, or 301D to communicate with a control module or other processing unit. In some embodiments, the sensor array communicates with the control module wirelessly and the tail portion may be omitted.

Figure 4C:
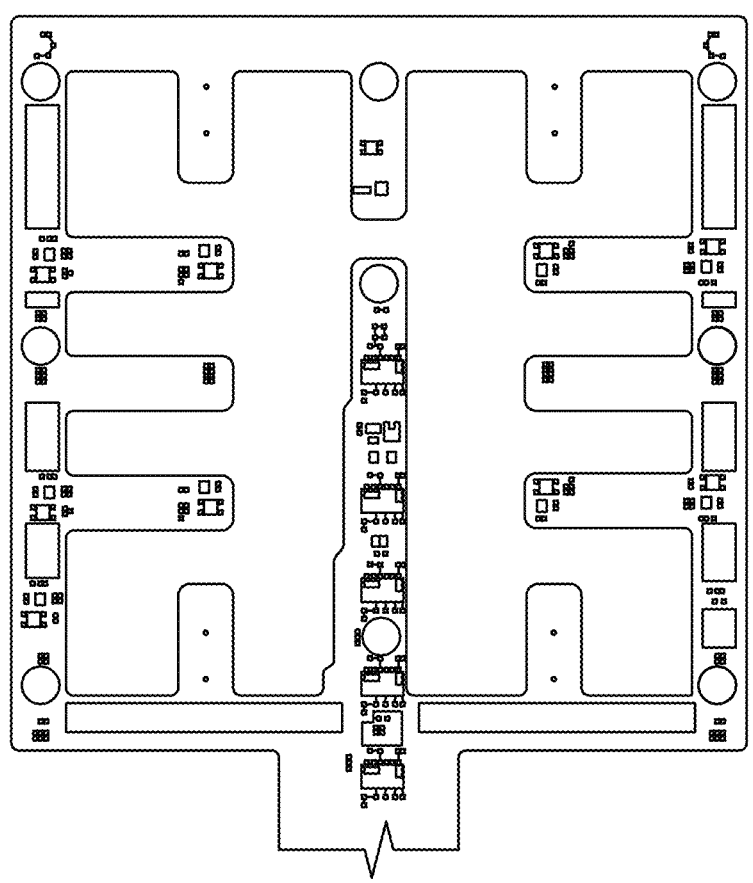
FIG. 4C illustrates the sensor array portion 301B of a sensor array shown in FIG. 4B.
Figure 4D:
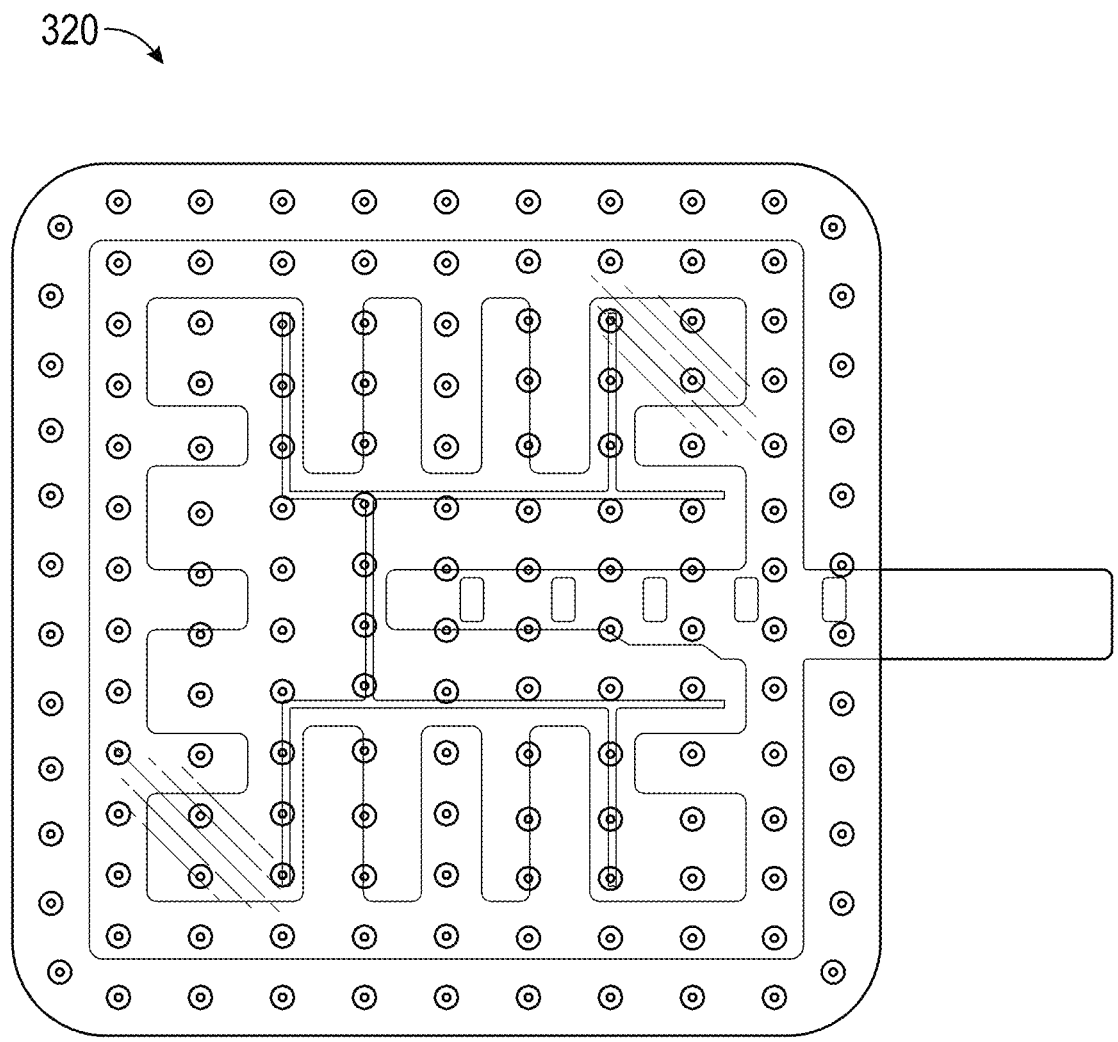
FIG. 4D illustrates a flexible sensor array incorporated into a perforated wound contact layer according to some embodiments.

FIG. 4C shows the sensor array portion 301B of the sensor array design of FIG. 4B in more detail. In any one or more of the embodiments of FIG. 3 or 4A-4D, the sensor array portion can include a plurality of portions that extend either around a perimeter of a wound dressing component such as a wound contact layer, or inward from an outer edge of the wound dressing component. For example, the illustrated embodiments include a plurality of linearly extending portions that may be parallel to edges of a wound dressing component, and in some embodiments, follow the entire perimeter of the wound dressing component. In some embodiments, the sensor array portion may comprise a first plurality of parallel linearly extending portions that are perpendicular to a second plurality of parallel linearly extending portions. These linearly extending portions may also have different lengths and may extend inward to different locations within an interior of a wound dressing component. The sensor array portion preferably does not cover the entire wound dressing component, so that gaps are formed between portions of the sensor array. As shown in FIG. 3, this allows some, and possibly a majority of the wound dressing component to be uncovered by the sensor array. For example, for a perforated wound contact layer as shown in FIGS. 3 and 4D, the sensor array portion 301 may not block a majority of the perforations in the wound contact layer. In some embodiments, the sensor array may also be perforated or shaped to match the perforations in the wound contact layer to minimize the blocking of perforations to fluid flow.

FIG. 4D illustrates a flexible sensor array incorporated into a perforated wound contact layer 320 according to some embodiments. As is illustrated, the sensor array can be sandwiched between two films or wound contact layers. The wound contact layers can have perforations formed as slits or holes as described herein that are small enough to help prevent tissue ingrowth into the wound dressing while allowing wound exudate to flow into the dressing. In some embodiments, the wound contact layers can have one or more slits that increase flexibility of the wound contact layer with integrated sensor array. In some embodiments, one of the wound contact layers can have extra cut outs to accommodate the sensors so that they can contact the skin directly.

Connectivity for the sensor array can vary depending on the various sensors and sensor array designs utilized. In some embodiments, for example as shown in FIG. 4B, a total of 79 connections can be used to connect the components of the sensor array. The sensor arrays can be terminated in two parallel 40-way 0.5 mm pitch Flat Flexible Cable (FFC) contact surfaces, with terminals on the top surface, designed to be connected to an FFC connector such as Molex 54104-4031.

In some embodiments, one or more of sensors, such as thermistors, conductivity sensors, SpO2 sensors, color sensors, or the like, can be used on the sensor array to provide information relating to conditions of the wound and/or periwound. Any of the sensor arrays and/or individual sensors disclosed herein can assist a clinician in monitoring the status of the wound, which can include healing of the wound or non-healing of the wound (such as, static, degrading, or the like). The one or more sensors can operate individually or in coordination with each other to provide data relating to the wound and wound healing characteristics.

Temperature sensors can use thermocouples or thermistors to measure temperature. The thermistors can be used to measure or track the temperature of the underlying wound or the thermal environment within the wound dressing. The thermometry sensors can be calibrated and the data obtained from the sensors can be processed to provide information about the wound environment. In some embodiments, an ambient sensor measuring ambient air temperature can also be used to assist in eliminating problems associated with environment temperature shifts.

Optical sensors can be used to measure wound appearance using an RGB sensor with an illumination source. In some embodiments, both the RGB sensor and the illumination source would be pressed up against the skin, such that light would penetrate into the tissue and take on the spectral features of the tissue itself.

Light propagation in tissue can be dominated by two major phenomena, scattering and attenuation. For attenuation, as light passes through tissue, its intensity may be lost due to absorption by various components of the tissue. Blue light tends to be attenuated heavily, whilst light at the red end of the spectrum tends to be attenuated least.

Scattering processes can be more complex, and can have various "regimes" which must be considered. The first aspect of scattering is based on the size of the scattering centre compared with the wavelength of incident light. If the scattering center is much smaller than the wavelength of light, then Rayleigh scattering can be assumed. If the scattering center is on the order of the wavelength of light, then a more detailed Mie scattering formulation must be considered. Another factor involved in scattering light is the distance between input and output of the scattering media. If the mean free path of the light (the distance between scattering events) is much larger than the distance travelled, then ballistic photon transport is assumed. In the case of tissue, scatting events are approximately 100 microns apart—so a 1 mm path distance would effectively randomise the photon direction and the system would enter a diffusive regime.

Ultra bright light emitting diodes (LEDs), an RGB sensor, and polyester optical filters can be used as components of the optical sensors to measure through tissue color differentiation. For example, because surface color can be measured from reflected light, a color can be measured from light which has passed through the tissue first for a given geometry. This can include color sensing from diffuse scattered light, from an LED in contact with the skin. In some embodiments, an LED can be used with an RGB sensor nearby to detect the light which has diffused through the tissue. The optical sensors can image with diffuse internal light or surface reflected light.

Additionally, the optical sensors can be used to measure autofluorescence. Autoflourescense is used because the tissue is absorbing light at one wavelength, and emitting at another. Additionally, dead tissue may not auto-fluoresce and so this could be a very strong indication as to if the tissue is healthy or not. Due to blue light (or even UV light) having such a short penetration depth, it may be very useful for example to have a UV light with a red sensitive photodiode nearby (or some other wavelength shifted band) to act as a binary test for healthy tissue, which would auto-fluoresce at a very particular wavelength.

Conductivity sensors can be used to determine the difference between living and dead tissue or to show a change in impedance due to a wound being opened up in morbid tissue. Conductivity sensors can include Ag/AgCl electrodes and an impedance analyser. The conductivity sensors can be used to measure the change of impedance of a region of wound growth by measuring the impedance of the surrounding tissue/area. In some embodiments, the sensor array can utilize conductivity sensors to measure the change in conductivity on perimeter electrodes due to a wound size or wound shape change. In some embodiments, the conductivity sensors can be used in the wound bed or on the perimeter of the wound.

In some embodiments, pH changing pads can be used as a pH sensor. A spectrometer and a broadband white light source can be used to measure the spectral response of the pH dye. The illumination and imaging can be provided on the surface of the wound dressing that is in contact with the wound and at the same side as the fluid application, the bottom surface. Alternatively, in some embodiments, the illumination and imaging source can be provided on the surface of the wound dressing opposite the bottom surface and away from fluid application or the top surface of the dressing.

In some embodiments, pulse oximetry SpO2 sensors can be used. To measure how oxygenated the blood is and the pulsatile blood flow can be observed. Pulse oximetry measurements work by taking a time resolved measurement of light absorption/transmission in tissue at two different optical wavelengths. When hemoglobin becomes oxygenated, its absorption spectrum changes with regards to non-oxygenated blood. By taking a measurement at two different wavelengths, one gains a ratio metric measure of how oxygenated the blood is.

The components in the sensor array can be connected through multiple connections. In some embodiments, the thermistors can be arranged in groups of five. Each thermistor is nominally 10 kΩ, and each group of five has a common ground. There are five groups of thermistors, giving a total of 30 connections. In some embodiments, there can be nine conductivity terminals. Each conductivity terminal requires one connection, giving a total of 9 connections. In some embodiments, there can be five SpO2 sensors. Each SpO2 sensor requires three connections, plus power and ground (these are covered separately), giving a total of 15 connections. In some embodiments, there can be 10 color sensors. Each color sensor comprises an RGB LED and an RGB photodiode. Each color sensor requires six connections, however five of these are common to every sensor, giving a total of 15 connections. Power and ground are considered separately. In some embodiments, there can be 5 pH sensors. The pH sensors can be a color-change discs, and can be sensed using the color sensors described above. Therefore, the pH sensors require no additional connections. There can be three power rails, and seven ground return signals, giving a total of 10 common connections. In some embodiments, the sensor array can include 25 thermistor (Murata NCP15WB473E03RC), 9 conductivity terminal, 5 SpO2 (ADPD144RI), 10 RGB LED (such as KPTF-1616RGBC-13), 10 RGB Color Sensor, 10 FET, a printed circuit board (PCB), and an assembly.

As described herein, a control module can be used to interface with the sensor array. Controller 24 can include one or more of the following features. In some embodiments, the control module can contain a power source, such as batteries, and electronics to drive the sensors. The control module can also log data at appropriate intervals and allow data transfer to an external computing device, such as a personal computer (PC) as shown in FIG. 1A. The control module can be customized to have various features depending on the sensors used in the sensor array and the data collected by the sensors. In some embodiments, the control module can be comfortable enough and small enough to be worn continuously for several weeks. In some embodiments, the control module can be positioned near the wound dressing or on the wound dressing. In some embodiments, the control module can be positioned in a remote location from the wound dressing and accompanying sensor array. The control module can communicate with the sensor array and wound dressing through electrical wires or through wireless communication whether positioned on the dressing, near the dressing, or remote from the wound dressing. In some embodiments, the control module can be adapted to be utilized with different sensor arrays and can enable easy replacement of the sensor array.

In some embodiments, the control module can include various requirements and combination of features including but not limited to the features listed in Table 1 below.

TABLE 1

Figure 4E:
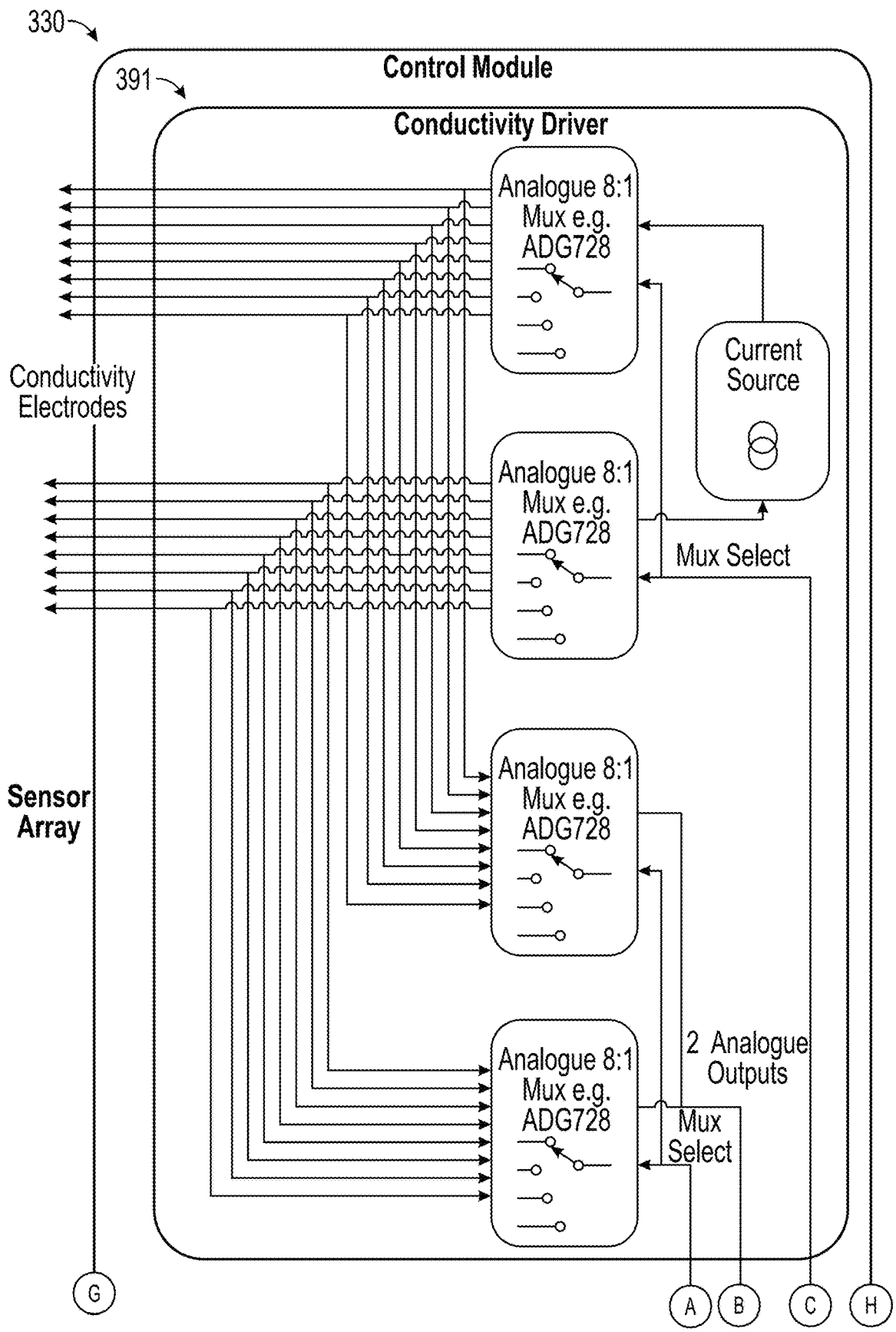
FIG. 4E illustrates a control module according to some embodiments.
Figure 4E:
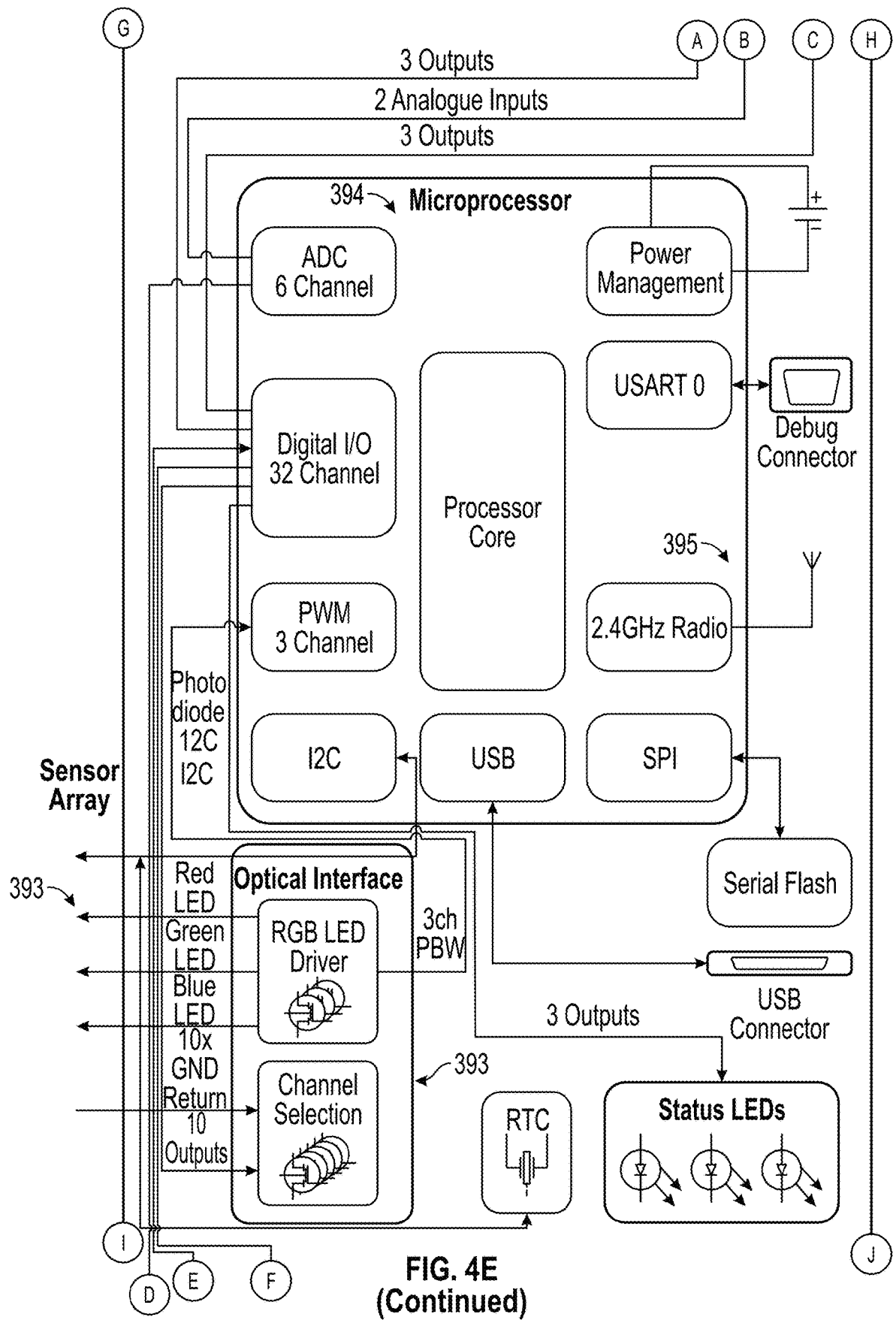
Figure 4E:
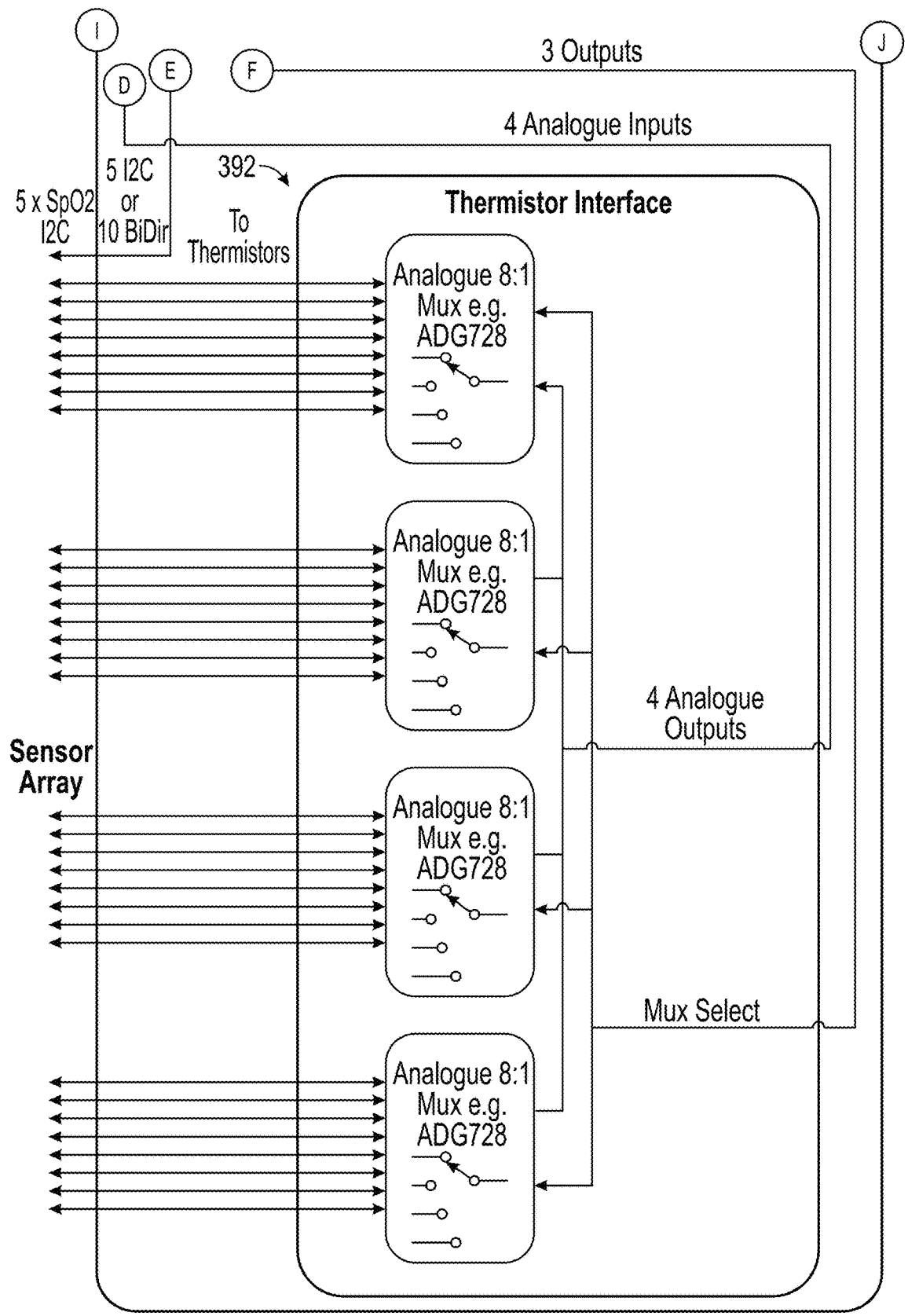

OPTIONAL FEATURES FOR CONTROL MODULE 7 day operation from a single set of batteries
28 day local, non-volatile, storage capacity
Easy to charge, or to replace battery
Wireless link to PC/tablet (such as Bluetooth)
Wired link to PC (optional, micro-USB)
Drive electronics for thermistors
Drive electronics for conductivity sensors
Drive electronics for optical sensors
Drive electronics for SpO2 sensors
Power management
Real Time Clock (RTC) to allow accurate data logging, and correlation with other measurands
Ability to change sample rates and intervals (useful for SpO2) for each sensor
Indication of status via LED, such as (Green: Awake; Flashing green: Charging; Blue: Wireless link established; Flashing blue: Wireless data transfer; Yellow: Wired link established; Flashing yellow: Wired data transfer; Red: Battery low; Flashing red: Battery very low FIG. 4E illustrates a block diagram 330 of a control module according to some embodiments. Controller 24 can include one or more of the illustrated and described features. The block diagram of the control module includes a conductivity driver box 391 displaying features of the conductivity driver. Box 392 shows the features of the thermistor interface and box 393 shows the features of the optical interface. The control module can include a controller or microprocessor with features similar to those shown in box 394. Real time clock (RTC), Status LEDs, USB connector, Serial Flash, and Debug Connector can be included as features of the control module as shown in FIG. 4E.

In some embodiments, the microprocessor can have one or more of the following features: 2.4 GHz or another suitable frequency radio 395 (either integrated, or external) with a suitable antenna or antennas; Supplied Bluetooth software stack; SPI interface; USB (or UART for external USB driver); I2C; 3 channel PWM; 32 GPIO; or 6-channel ADC. In some embodiments, the device can require at least 48 I/O pins or possibly more due to banking limitations. Bluetooth stack typically requires ~20 kB on-board Flash, so a minimum of 32 kB can be required. In some embodiment, 64 kB can be required if complex data processing is considered. The processor core can be ARM Cortex M4 or a similar processor core. In some embodiments, the parts can include ST's STM32L433LC or STM32F302R8, which would require an external radio, or NXP's Kinetis KW range including integrated radio.

In some embodiment, the control module can include a memory component where the amount of local storage depends on the sample rate and resolution of the sensors. For example, an estimated data requirement of 256 Mb (32 MB) can be met by using a serial Flash device from a number of manufacturers (Micron, Spansion).

The control module can utilize one or more analogue switches. In some embodiments, analogue switches with good on resistance and reasonable bandwidth can be used. For example, Analog Devices' ADG72 or NXP's NX3L4051 HR can be used. Based on the initial system architecture, 8 of these will be required. The control module can incorporate a power source, such as a battery. For example a 300 mWh/day battery can be used. For 7 days this is 2100 mWh. This could be provided by: a 10 days, non-rechargeable, ER14250 (14.5 mm diameter×25 mm) LiSOCl2 cell; or a 7 days, rechargeable, Li 14500 (14.5 mm diameter×500 mm) Li-Ion.

The control module can incorporate a real time clock (RTC). The RTC can be chosen from any RTC devices with crystal. The control module can also include miscellaneous resistors, capacitors, connectors, charge controllers, and other power supplies.

The PCB of the control module can be a 4-layer board, approximately 50 mm×20 mm, or 25 mm×40 mm. The type of PCB used can be largely driven by connection requirements to sensor array.

The enclosure of the control module can be a two part moulding, with clip features to allow easy access for changing sensor arrays or batteries.

The data collected through the sensor array can be passed through the control module and processed by host software. The software may be executed on a computing or processing device (see FIG. 1A.). The processing device can be a PC, tablet, smartphone, or other computer capable of running host software. The processing device executing the software can be in communication with the control module through electrical wires or through wireless communication. In some embodiments, the software may be configured to provide access to the data held on the control module, but not to perform big-data analysis. The host software can include an interface to the control module via Bluetooth or USB. In some embodiments, the host software can read the status of control module, download logged data from control module, upload sample rate control to control module, convert data from control module into format suitable for processing by big-data analysis engine, or upload data to cloud (see FIG. 1A) for processing by analysis engine.

The software may be developed for PC (Windows/Linux), tablet or smartphone (Android/iOS), or for multiple platforms.

Additional embodiments of wound dressing with sensors and other related systems are disclosed in International Application No. PCT/IB2017/000693, filed on May 12, 2017, titled SENSOR ENABLED WOUND MONITORING AND THERAPY APPARATUS, the disclosure of which is hereby incorporated by reference in its entirety.

In some embodiments, a source of negative pressure (such as a pump) and some or all other components of the topical negative pressure system, such as power source(s), sensor (s), connector(s), user interface component(s) (such as button(s), switch(es), speaker(s), screen(s), etc.) and the like, can be integral with the wound dressing. In some embodiments, the components can be integrated below, within, on top of, or adjacent to the backing layer. In some embodiments, the wound dressing can include a second cover layer or a second filter layer for positioning over the layers of the wound dressing and any of the integrated components. The second cover layer can be the upper most layer of the dressing or can be a separate envelope that enclosed the integrated components of the topical negative pressure system.

As used herein the upper layer, top layer, or layer above refers to a layer furthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound.

Component Positioning in Sensor Enabled Wound Dressing

In some embodiments, electrical or electronic components, such as sensors, connections, or the like, can be placed or positioned on or embedded in one or more wound dressing components, which can be placed in or on the wound, skin, or both the wound and the skin. For example, one or more electronic components can be positioned on a wound contact layer side that faces the wound, such as the lower surface 224 of the wound contact layer 222 in FIG. 2B. The wound contact layer can be flexible, elastic, or stretchable or substantially flexible, elastic, or stretchable in order to conform to or cover the wound. For example, the wound contact layer can be made from a stretchable or substantially stretchable material, such as one or more of polyurethane, thermoplastic polyurethane (TPU), silicone, polycarbonate, polyethylene, polyimide, polyamide, polyester, polyethelene tetraphthalate (PET), polybutalene tetreaphthalate (PBT), polyethylene naphthalate (PEN), polyetherimide (PEI), along with various fluropolymers (FEP) and copolymers, or another suitable material. In some instances, one or more electronic components can be alternatively or additionally placed or positioned on or embedded in any one or more of a transmission layer, absorbent layer, backing layer, or any other suitable layer of the wound dressing.

Stretchable or substantially stretchable material can be stretched to 5% or less or more, 10% or less or more, 20% or less or more, or more than 20% of its starting dimensions, such as length or width. In some cases, the stretchable or substantially stretchable material can return to within 5% or less or more of the starting dimensions (such as length or width) after being stretched.

In some implementations, while it may be desirable for the wound contact layer to be stretchable to better conform to or cover the wound, at least some of the electronic components may not be stretchable or flexible. In such instances, undesirable or excessive localized strain or stress may be exerted on the one or more electronic components, such as on the supporting area or mountings of an electronic component, when the wound is dressed with the wound dressing and the wound contact layer is positioned in or over the wound. For example, such stress can be due to patient movement, changes in the shape or size of the wound (such as, due to its healing), or the like. Such stress may cause movement, dislodgment, or malfunction of the one or more electronic components (for example, creation of an open circuit from a pin or another connector becoming disconnected). Alternatively or additionally, it may be desirable to maintain the position of one or more electronic components, such as one or more sensors, in the same or substantially same location or region on the wound contact layer with respect to the wound (such as, in contact with the wound) so that measurements collected by the one or more electronic components accurately capture changes over time in the same or substantially same location or region of the wound. While the surface of the stretchable wound contact layer may move when, for example, the patient moves, it may be desirable to have the one or more electronic components be located in the same location or region with respect to the wound.

As described herein, in some embodiments, one or more stiff, rigid, or non-stretchable or substantially stiff, rigid, or non-stretchable regions, such as one or more regions of non-stretchable or substantially non-stretchable material, can be mounted, positioned, or placed on the wound contact layer (or another suitable wound dressing component) for supporting one or more electronic components. Mounting, positioning, or placing one or more electronic components in the one or more non-stretchable or substantially non-stretchable regions can prevent formation of localized stress or assist with maintenance of the position of the one or more electronic components with respect to the wound. In some instances, one or more electronic components can be alternatively or additionally be flexible, such as mounted or printed on or supported by one or more flexible materials. For example, flexible plastic sheets or substrates, such as polyimide, polyether ether ketone (PEEK), polyester, silicone, or the like, can be used.

Figure 5A:
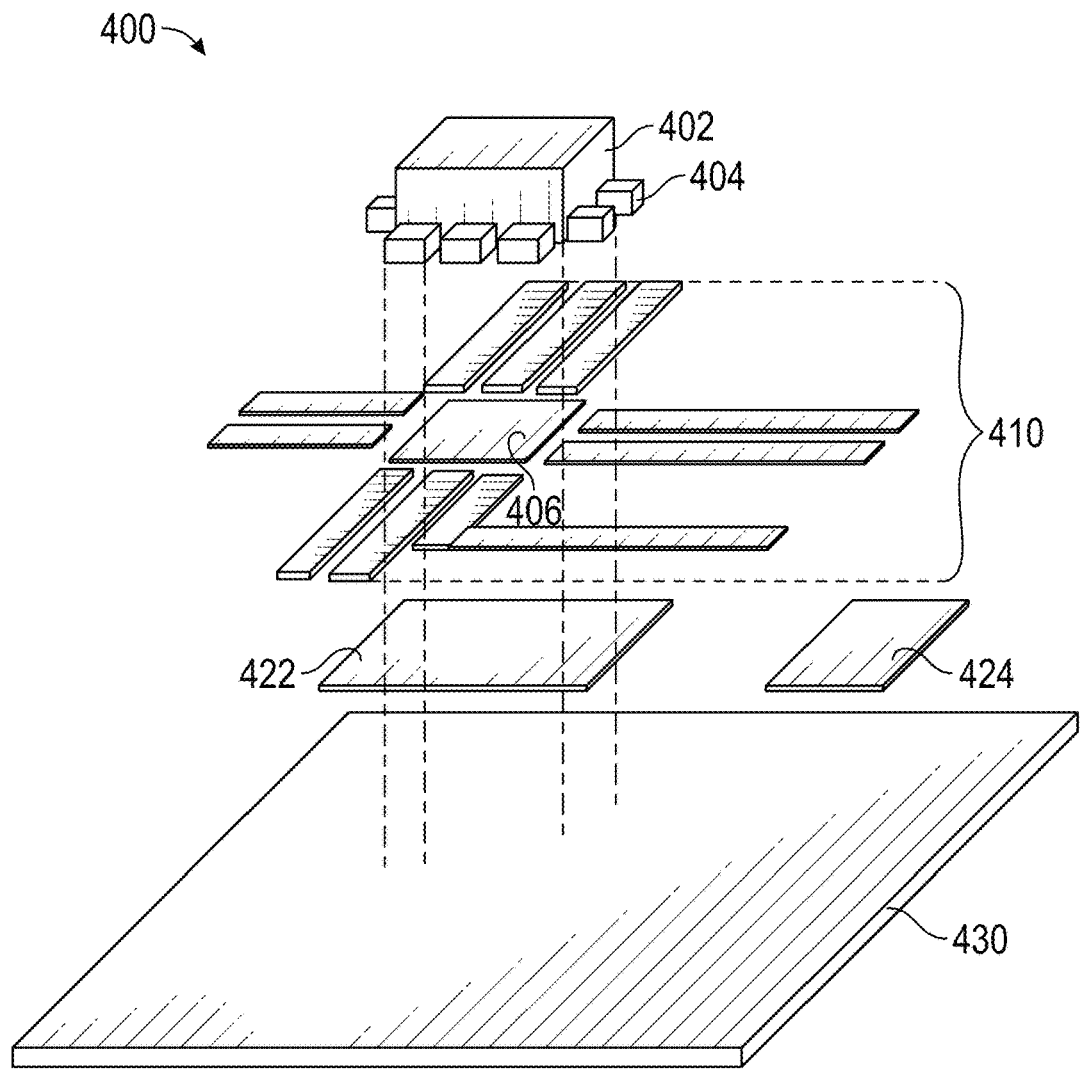
FIGS. 5A-5B illustrate a wound dressing with a plurality of electronic components according to some embodiments.
Figure 5B:
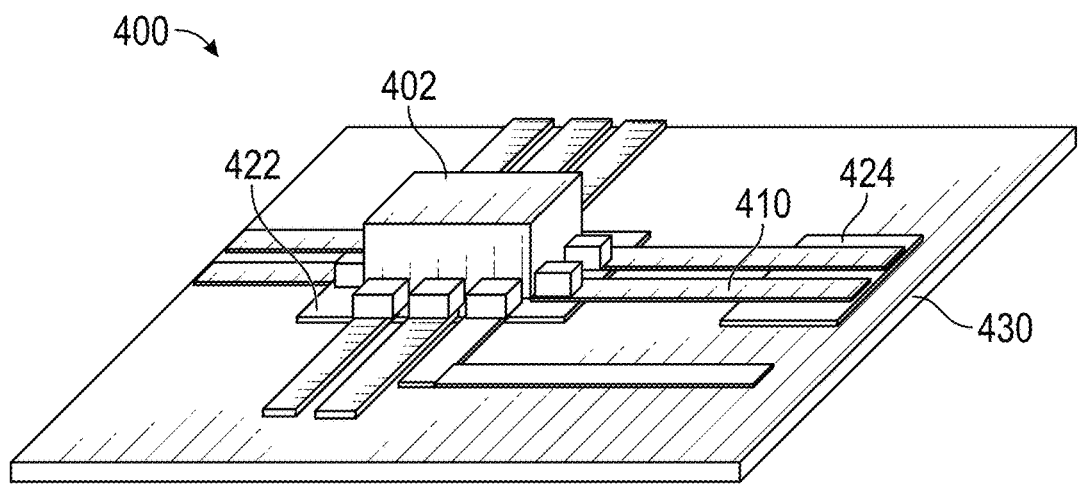

FIGS. 5A-5B illustrate a wound dressing 400 with a plurality of electronic components according to some embodiments. As is shown, a sheet or substrate 430 is configured to support one or more electronic components, including an electronic component or module 402 with a plurality of connectors 404 and a plurality of electronic connections 410, and non-stretchable or substantially non-stretchable regions 422 and 424. The substrate 430 can be a stretchable or substantially stretchable wound contact layer as described herein. The electronic module 402 can be any electronic component described herein, such as a sensor, light source (such as an LED, temperature sensor, optical sensor, etc.), controller or processor (such as a communication processor), or the like. Electronic connections 410 can be tracks printed on the substrate 430, such as using conductive copper, conductive ink (such as silver ink, silver/silver chloride ink, copper ink, graphite ink, carbon ink, dielectric ink, etc.), or the like. At least some of the electronic connections 410 can be flexible or stretchable or substantially flexible or stretchable. Connectors 404 can be configured to electronically connect the electronic module 402 to the electronic connection 410 (as illustrated in FIG. 4B), which in turn can be connected to other electronic modules (not shown) positioned on the substrate 430, on or in other components of the wound dressing, or external to the wound dressing. Connectors 404 can be pins, leads, bumps, or the like. Additionally or alternatively a socket can be used to support and electronically connect the electronic module 402. Regions 422 and 424 can include non-stretchable or substantially non-stretchable material, such as one or more of suitable adhesive, epoxy, polyester, polyimide, polyamide, PET, PBT, or another type of material with a high Young's modulus. One or more of the regions 422 and 424 can be printed on the substrate 430. As is used herein, printing material on a substrate can include one or more of laminating, adhering, or any other suitable technique.

FIG. 5B illustrates components positioned on the substrate 430. As shown, the electronic module 402 is mounted to or supported by the region 422. A portion or part of the electronic connections 410 is mounted to or supported by the region 424. Also illustrated are slits, holes, or perforations formed in the substrate 430 according to some embodiments. As described herein, the substrate 430 can be perforated using one or more of a cold pin perforation, hot pin perforation, laser ablation perforation, ultrasonic or ultrasound perforation, or the like to make the wound contact layer permeable to liquid and gas. In some implementations, one or more utilized perforation processes can generate either a flat or substantially substrate around the hole or an uneven surface (such as donut-shaped surface). Having a flat or substantially flat substrate can assist in generating a homogenous layer when conformal coating is applied (such as, via spray, brush, extrusion dye, or the like as described herein). Further, using a perforation process that leaves the surface of the substrate uneven or substantially uneven can introduce a greater risk of dislodging one or more components, such as the electronic connections 410 or the electronic module 402 when perforations are made around the components.

In certain implementations, perforations are made or patterned around one or more components placed on the substrate 430, such as the electronic connections 410, the electronic module 402, or the regions 422 or 424. Component indexing can be used to automatically locate position of the one or more components on the substrate 430 so that the one or more components are not damaged by perforations. In some embodiments, the substrate can be perforated before one or more components illustrated in FIG. 4A as placed on the substrate.

In some embodiments, in addition to or instead of the one of more regions 422 or 424, electronic components supported by the substrate 430 can be coated with non-stretchable or substantially non-stretchable coating (not shown), particularly if the substrate 430 is stretchable or substantially stretchable. As described herein, such coating can provide stress relief for the electronic components (which may include electronic modules or electronic connections). Coating can be applied on and around the electronic components. Coating can be one or more of biocompatible or hydrophobic.

Any non-stretchable or substantially non-stretchable coating described herein can be formed from acrylated or modified urethane material (such as, Henkel Loctite 3211). For example, coating can be one or more of Dymax 1901-M, Dymax 9001-E, Dymax 20351, Dymax 20558, Henkel Loctite 3211, or another suitable material.

In some embodiments, conformal coating (not shown) configured to encapsulate or coat one or more of the substrate 430 or components supported by the substrate, such as the electronic connections 410 or the electronic module 402 can be applied. Such coating can provide biocompatibility, shield or protect the electronics from coming into contact with fluids, or the like. Coating can include one or more suitable polymers, adhesives, such as 1072-M adhesive (for example Dymax 1072-M), 1165-M adhesive (such as, NovaChem Optimax 8002-LV, Dymax 1165-M, or the like), 10901-M adhesive (for instance, Dymax 1901-M or 9001-E Dymax), parylene (such as, Parylene C), silicones, epoxies, urethanes, acrylated urethanes, acrylated urethane alternatives (such as, Henkel Loctite 3381), or other suitable biocompatible and substantially stretchable materials. Conformal coating can be applied to the other side of the substrate 430 (such as, the side that does not support components) to encapsulate the substrate 430 in conformal coating.

Additional details regarding one or more of the wound dressing 400, non-stretchable or substantially non-stretchable coating, or conformal coating are described in one or more of International Patent Application No. PCT/EP2018/059333, filed on 11 Apr. 2018, or International Patent Application No. PCT/EP2018/069883, filed on 23 Jul. 2018, each of which is incorporated by reference in its entirety.

In some embodiments, one or more sensors can be positioned in or on a layer or layers of a wound dressing or another structure that is not in direct contact with a wound. In such cases, the sensors can measure one or more of impedance, temperature, color, pressure, or the like associated with the wound and/or periwound. For example, one or more sensors can be positioned above a dressing layer that transports or absorbs wound exudate. In this example, the one or more sensors can measure one or more of impedance, temperature, color, or the like of the wound exudate. These measurements can be used to determine status of the wound, which (as described herein) can include healing of the wound or non-healing of the wound.

Other Variations

In some embodiments, a wound monitoring and/or therapy system includes a wound dressing comprising one or more sensors configured to obtain measurement data of at least one of a wound or periwound. The system can also include one or more of the following: a controller configured to be connected to the wound dressing and further configured to receive measurement data from the wound dressing, a communication device configured to be connected to the controller and further configured to periodically receive data from the controller, a skin perfusion measurement device configured to measure skin perfusion pressure in a target area of the patient, a computing device configured to be connected to the communication device and the perfusion measurement device, the computing device further configured to receive data from the communication device and the perfusion measurement device, and a remote computing device configured to receive and aggregate data from the computing device.

The system of preceding paragraph can include one or more of the following features. The system can include a computing device configured to take one or more images of at least one of the wound or periwound and communicate image data to the remote computing device. The wound dressing can include a substantially flexible wound contact layer supporting the one or more sensors. The wound dressing can also include an antenna configured to communicate measurement data to at least one of the controller or communication device.

In some embodiments, a wound monitoring apparatus includes a wound dressing configured to be positioned in contact with a wound, the wound dressing including at least one substantially flexible substrate supporting one or more sensors.

The system and/or apparatus of one or more preceding paragraphs can include one or more of the following features. The at least one substantially flexible substrate can include a substantially flexible printed circuit. The substantially flexible printed circuit can include a flexible polymer. The at least one substantially flexible substrate can include a substantially flexible non-conducting mesh. The mesh can include a plurality of perforations. The one or more sensors can include a plurality of sensors electrically connected with each other, the plurality of sensors further configured to be electrically connected with a controller and a power source. The one or more sensors can include one or more temperature sensors, conductivity sensors, multispectral optical measurements sensors, pH sensors, pressure sensors, colorimetric sensors, optical sensors, ultraviolet (UV) sensors, or infrared (IR) sensors. The system and/or apparatus can include a controller in electrical communication with the one or more sensors, the controller configured to receive data from the one or more sensors and communicate the data to a processing device configured to process the data collected by the one or more sensors to determine one or more conditions associated with the wound.

The system and/or apparatus of one or more preceding paragraphs can include one or more of the following features. The at least one of the controller or the processing device can be configured to indicate, based on the one or more conditions associated with the wound, that the wound is healing or not healing. The controller can be configured to wirelessly communicate with at least one of the one or more sensors or the processing device. The controller can be configured to be in electrical communication with at least one of the one or more sensors or the processing device through one or more conductive tracks. The processing device can include a personal computer (PC), a tablet format computing device, a smartphone, or a custom computing device. Data collected by the one or more sensors can be configured to be communicated to a cloud computing device.

The system and/or apparatus of one or more preceding paragraphs can include one or more of the following features. The wound dressing can include a wound contact layer and the substrate can be positioned on or in the wound contact layer. The wound contact layer can include a first wound contact layer and a second wound contact layer, wherein the substrate is sandwiched between the first and second wound contact layers. At least one of the one or more sensors can be configured to be in direct contact with the wound and the at least one of the one or more sensors can be encapsulated between the first wound contact layer and the second wound contact layer. One or more sensors can include at least a first sensor configured to the in direct contact with the wound and at least a second sensor configured to not contact the wound.

The system and/or apparatus of one or more preceding paragraphs can include one or more of the following features. The system and/or apparatus can include an absorbent layer positioned over the wound contact layer and a backing layer positioned over the wound contact layer and the wound contact layer can be sealed to the backing layer. The system and/or apparatus can include a port on the backing layer, the port configured to connect the wound dressing to a source of negative pressure. The wound dressing can be included in a multi-layer wound dressing configured to treat the wound without the use of negative pressure. The system and/or apparatus can include a wound packing layer and a drape that are configured to be positioned over the wound separately from the wound dressing. The system and/or apparatus can include a negative pressure source configured to be in fluid communication with the wound dressing and further configured to apply negative pressure to the wound.

In some embodiments, a wound monitoring apparatus includes a wound dressing configured to be positioned in contact with a wound, the wound dressing comprising one or more sensors configured to obtain measurement data of at least one of the wound or periwound and a controller configured to receive measurement data obtained by the one or more sensors, and transmit measurement data to a remote computing device according to a security protocol.

The apparatus of the preceding paragraph can include one or more of the following features. The wound dressing can include a substantially flexible wound contact layer supporting the one or more sensors. The security protocol can include encrypting the measurement data. The security protocol can comprise not including in the transmission patient identification information or real time clock information associated with the measurement data. The controller can be further configured to maintain non-real time clock, and wherein the security protocol can comprise inclusion of non-real time clock data associated with the measurement data in the transmission. Transmission of measurement data with the associated non-real time clock data can causes the remote computing device to utilize the non-real time clock data to correlate the measurement data with real time clock data.

Although some of the disclosed embodiments illustrate arrangement of electronic components, such as sensors, in or on a wound dressing, disclosed component arrangements are not so limited. In some implementations, the components can be arranged on another dressing, structure, or substrate or could be provided separately for being positioned over any wound, as broadly defined herein. Component arrangements can be used for one or more of preventing or treating a wound.

In some embodiments, one or more electronic components can be positioned on the side of a wound contact layer opposite the side that faces the wound. Systems and methods described herein are equally applicable to such arrangements of components. Any wound dressing embodiment described herein can include features of any of the other described wound dressing embodiments. Similarly, any controller described herein can include features of any of the other described wound dressing embodiments. Further, any device, component, or module described in a certain embodiment can include features of any of the other described embodiments of the device, component, or module.

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value. Moreover, although blocks of the various processes may be described in terms of determining whether a value meets or does not meet a particular threshold, the blocks can be similarly understood, for example, in terms of a value (i) being below or above a threshold or (ii) satisfying or not satisfying a threshold.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as controllers, processors, ASICs, FPGAs, and the like, can include logic circuitry. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A wound monitoring and/or therapy apparatus comprising:
   a communication circuitry; and
   an electronic control circuitry configured to:
     maintain a device clock indicative of a non-real time clock by counting from a random number or a unique hardware identification number of the electronic control circuitry;
     receive a measurement data obtained by one or more sensors of a wound dressing configured to be positioned in contact with a wound of a patient, the one or more sensors configured to obtain a measurement data of at least one of the wound or a periwound; and
     cause the communication circuitry to transmit the measurement data to a remote computing device along with the device clock associated with the measurement data.

2. The apparatus of claim 1, wherein the electronic control circuitry is configured to cause the communication circuitry to transmit the measurement data to the remote computing device without a real time clock.

3. The apparatus of claim 1, wherein the electronic control circuitry is configured to cause the communication circuitry to transmit the measurement data to the remote computing device without a patient identification information.

4. The apparatus of claim 1, wherein the electronic control circuitry is configured to cause the communication circuitry to transmit the measurement data to the remote computing device without a patient identification information and without a real time clock.

5. The apparatus of claim 1, wherein transmission of the measurement data is encrypted.

6. The apparatus of claim 1, wherein transmission of the measurement data with the device clock associated with the measurement data causes the remote computing device to utilize the device clock to correlate the measurement data with a real time clock.

7. The apparatus of claim 1, wherein:
   the electronic control circuitry is further configured to cause the communication circuitry to transmit an initial device clock to the remote computing device during initialization; and
   transmission of the measurement data with the device clock associated with the measurement data causes the remote computing device to determine an elapsed time between the initial device clock and the device clock associated with the measurement data and correlate the measurement data with a real time clock based on the elapsed time.

8. The apparatus of claim 1, wherein the electronic control circuitry is configured to maintain the device clock in response to power being supplied to the electronic control circuitry.

9. The apparatus of claim 8, wherein, in response to a power interruption, the electronic control circuitry is further configured to reestablish the device clock from a previous device clock value before the power interruption.

10. A method of operating a wound monitoring and/or therapy apparatus, the method comprising:
    by an electronic control circuitry:

generating a device clock indicative of a non-real time clock by counting from a random number or a unique hardware identification number of the electronic control circuitry;

receiving measurement data obtained by one or more sensors of a wound dressing configured to be positioned in contact with a wound, the one or more sensors configured to obtain measurement data of at least one of the wound or periwound; and causing transmission of the measurement data to a remote computing device along with the device clock associated with the measurement data.

11. The method of claim 10, wherein transmission of the measurement data to the remote computing device excludes transmission of a patient identification information.

12. The method of claim 10, wherein transmission of the measurement data to the remote computing device excludes transmission of a real time clock.

13. The method of claim 10, wherein transmission of the measurement data to the remote computing device excludes transmission of a patient identification information and a real time clock.

14. The method of claim 10, wherein transmission of the measurement data is encrypted.

15. The method of claim 10, wherein transmission of the measurement data with the device clock associated with the measurement data causes the remote computing device to utilize the device clock to correlate the measurement data with a real time clock.

16. The method of claim 10, further comprising:

causing transmission of an initial device clock to the remote computing device during initialization, wherein transmission of the measurement data with the device clock associated with the measurement data causes the remote computing device to determine an elapsed time between the initial device clock and the device clock associated with the measurement data and correlate the measurement data with a real time clock based on the elapsed time.

17. The method of claim 10, further comprising maintaining the device clock in response to power being supplied to the electronic control circuitry.

18. The method of claim 17, further comprising, in response to a power interruption, reestablishing the device clock from a previous device clock value before the power interruption.

* * * * *